United States Patent
Burley et al.

(10) Patent No.: US 10,022,131 B1
(45) Date of Patent: Jul. 17, 2018

(54) FLEXIBLE DRILL BIT AND ANGLED DRILL GUIDE FOR USE WITH THE SAME

(71) Applicant: Pivot Medical, Inc., Sunnyvale, CA (US)

(72) Inventors: J. Brook Burley, Mountain View, CA (US); Jeremy Graul, Elk Grove, CA (US)

(73) Assignee: Pivot Medical, Inc., San Jose, CA (US)

( * ) Notice: Subject to any disclaimer, the term of this patent is extended or adjusted under 35 U.S.C. 154(b) by 0 days.

(21) Appl. No.: 15/231,180

(22) Filed: Aug. 8, 2016

Related U.S. Application Data

(63) Continuation-in-part of application No. 13/735,806, filed on Jan. 7, 2013, and a continuation-in-part of application No. 13/764,565, filed on Feb. 11, 2013.

(60) Provisional application No. 61/583,265, filed on Jan. 5, 2012, provisional application No. 61/596,993, filed on Feb. 9, 2012, provisional application No. 62/201,677, filed on Aug. 6, 2015.

(51) Int. Cl.
| | | |
|---|---|---|
| *A61B 17/16* | (2006.01) | |
| *A61B 17/17* | (2006.01) | |
| *A61B 17/00* | (2006.01) | |

(52) U.S. Cl.
CPC ...... *A61B 17/1631* (2013.01); *A61B 17/1615* (2013.01); *A61B 17/17* (2013.01); *A61B 2017/00526* (2013.01); *A61B 2017/00867* (2013.01); *A61B 2017/00946* (2013.01)

(58) Field of Classification Search
CPC ...... A61B 17/17; A61B 17/16; A61B 17/1615
See application file for complete search history.

(56) References Cited

U.S. PATENT DOCUMENTS

| | | | |
|---|---|---|---|
| 4,541,423 A | 9/1985 | Barber | |
| 5,387,218 A | 2/1995 | Meswania | |
| 5,601,550 A | 2/1997 | Esser | |
| 5,733,290 A | 3/1998 | McCue et al. | |
| 6,309,396 B1 | 10/2001 | Ritland | |
| 6,422,010 B1 * | 7/2002 | Julien | F01D 25/005 60/527 |

(Continued)

FOREIGN PATENT DOCUMENTS

| | | |
|---|---|---|
| EP | 1584299 | 10/2005 |
| WO | WO 2011/161676 | 12/2011 |
| WO | WO 2014/107729 | 7/2014 |

*Primary Examiner* — Christopher Beccia
(74) *Attorney, Agent, or Firm* — Pandiscio & Pandiscio

(57) ABSTRACT

A flexible drill bit comprising: a proximal shaft portion for connecting to a source of turning; a distal cutting tip portion for boring into a material; and an intermediate shaft portion extending between the proximal shaft portion and the distal cutting tip portion, the intermediate shaft portion being characterized by (i) sufficient longitudinal flexibility so as to permit the flexible drill bit to be passed along a curve, and (ii) sufficient torsional strength to permit the flexible drill bit to bore into the material. Apparatus for drilling a hole in material, the apparatus comprising: an angled drill guide comprising a curved distal section, a less-curved proximal section, and a lumen extending therebetween, wherein the less-curved proximal section comprises a flat extending therealong for reducing the effective diameter of the less-curved proximal section so as to minimize interference between the angled drill guide and the side wall of an access cannula.

26 Claims, 49 Drawing Sheets

(56) References Cited

U.S. PATENT DOCUMENTS

| | | |
|---|---|---|
| 6,423,080 B1 | 7/2002 | Gellman et al. |
| 2005/0054953 A1* | 3/2005 | Ryan .................... A61M 25/09 600/585 |
| 2005/0059975 A1 | 3/2005 | Fenger et al. |
| 2007/0264093 A1 | 11/2007 | White et al. |
| 2009/0012526 A1* | 1/2009 | Fletcher ............. A61B 17/1615 606/96 |
| 2009/0149890 A1 | 6/2009 | Martin |
| 2009/0204121 A1 | 8/2009 | Cavallazzi et al. |
| 2010/0191248 A1 | 7/2010 | Mehta et al. |
| 2010/0286694 A1 | 11/2010 | Rio et al. |
| 2010/0292722 A1 | 11/2010 | Klaue |
| 2011/0015674 A1 | 1/2011 | Howard et al. |
| 2011/0071545 A1 | 3/2011 | Pamichev et al. |
| 2011/0208194 A1* | 8/2011 | Steiner ............... A61B 17/1631 606/80 |
| 2011/0251621 A1 | 10/2011 | Sluss et al. |
| 2012/0123417 A1 | 5/2012 | Smith |
| 2013/0158596 A1 | 6/2013 | Miller et al. |
| 2014/0107657 A1 | 4/2014 | Norton et al. |

* cited by examiner

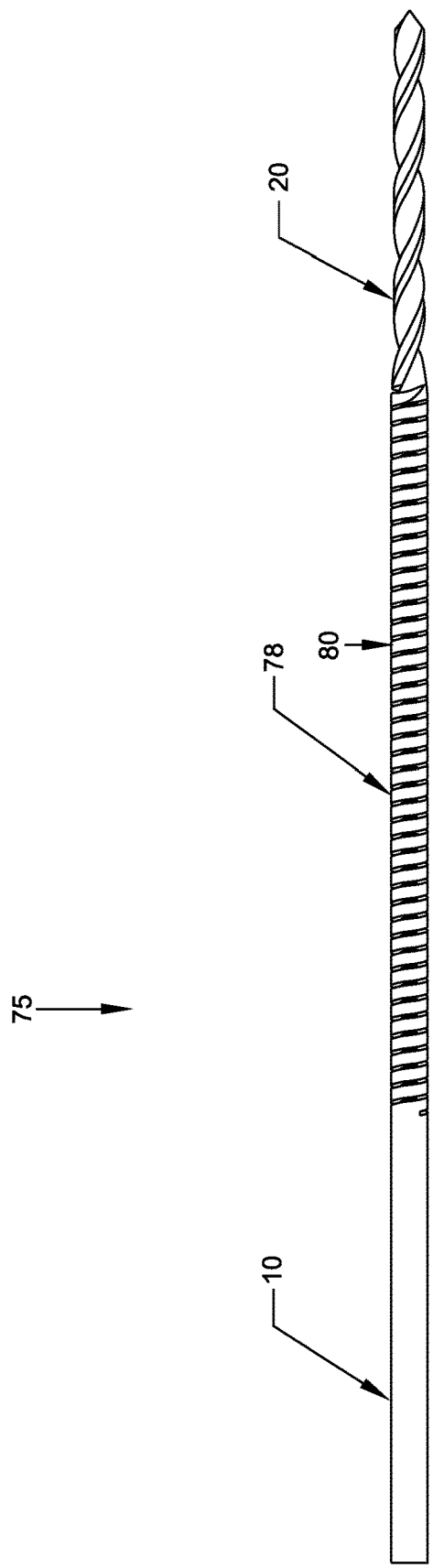

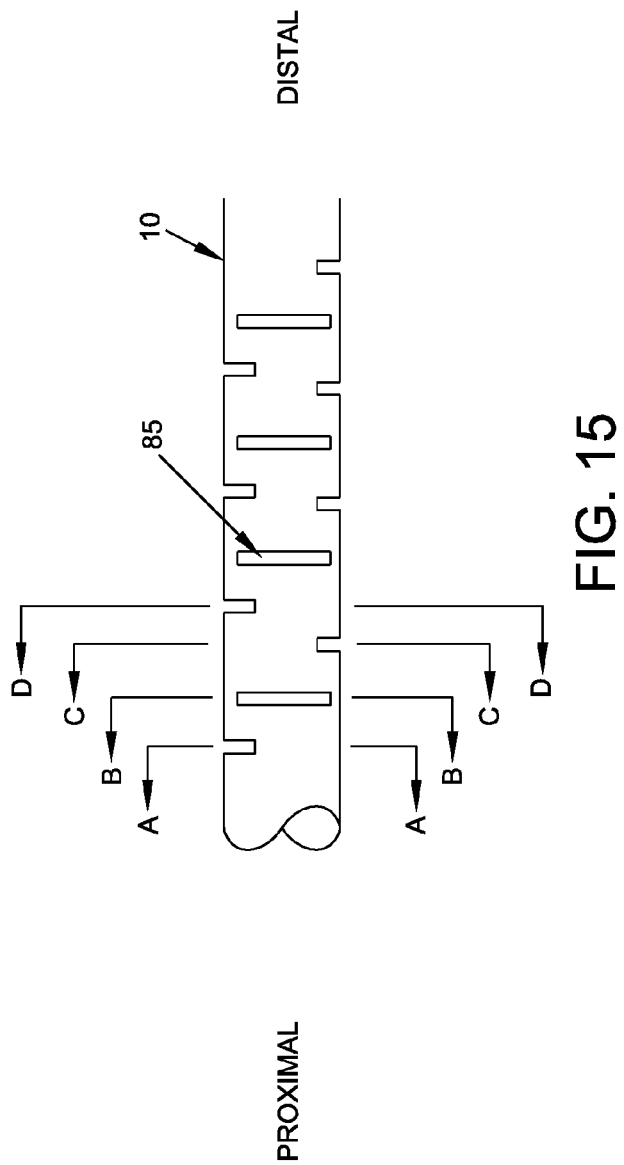

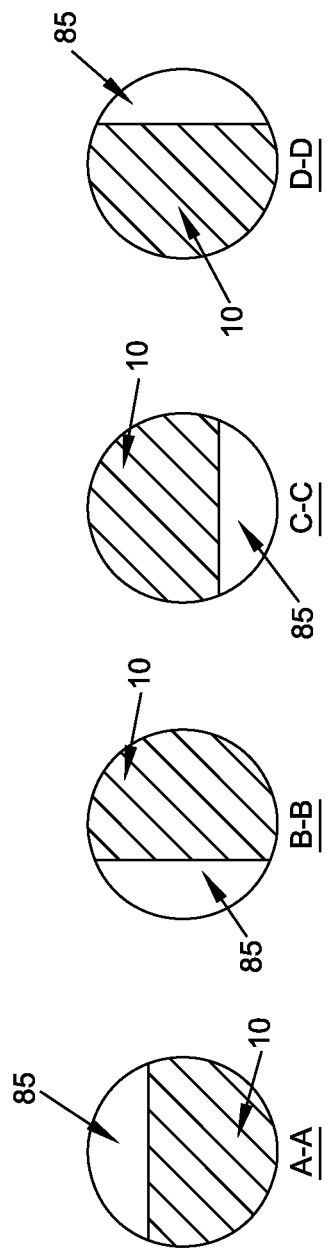

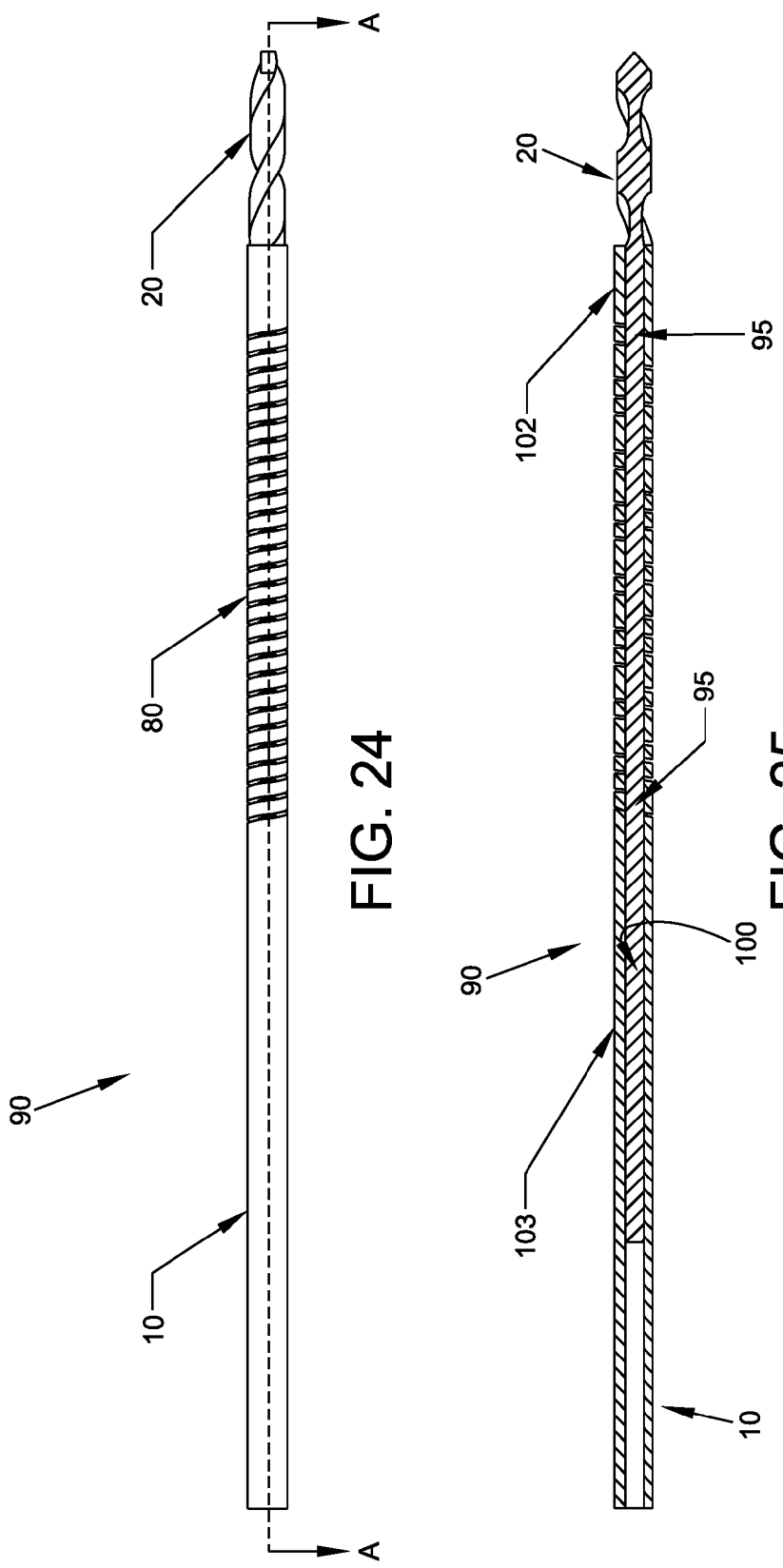

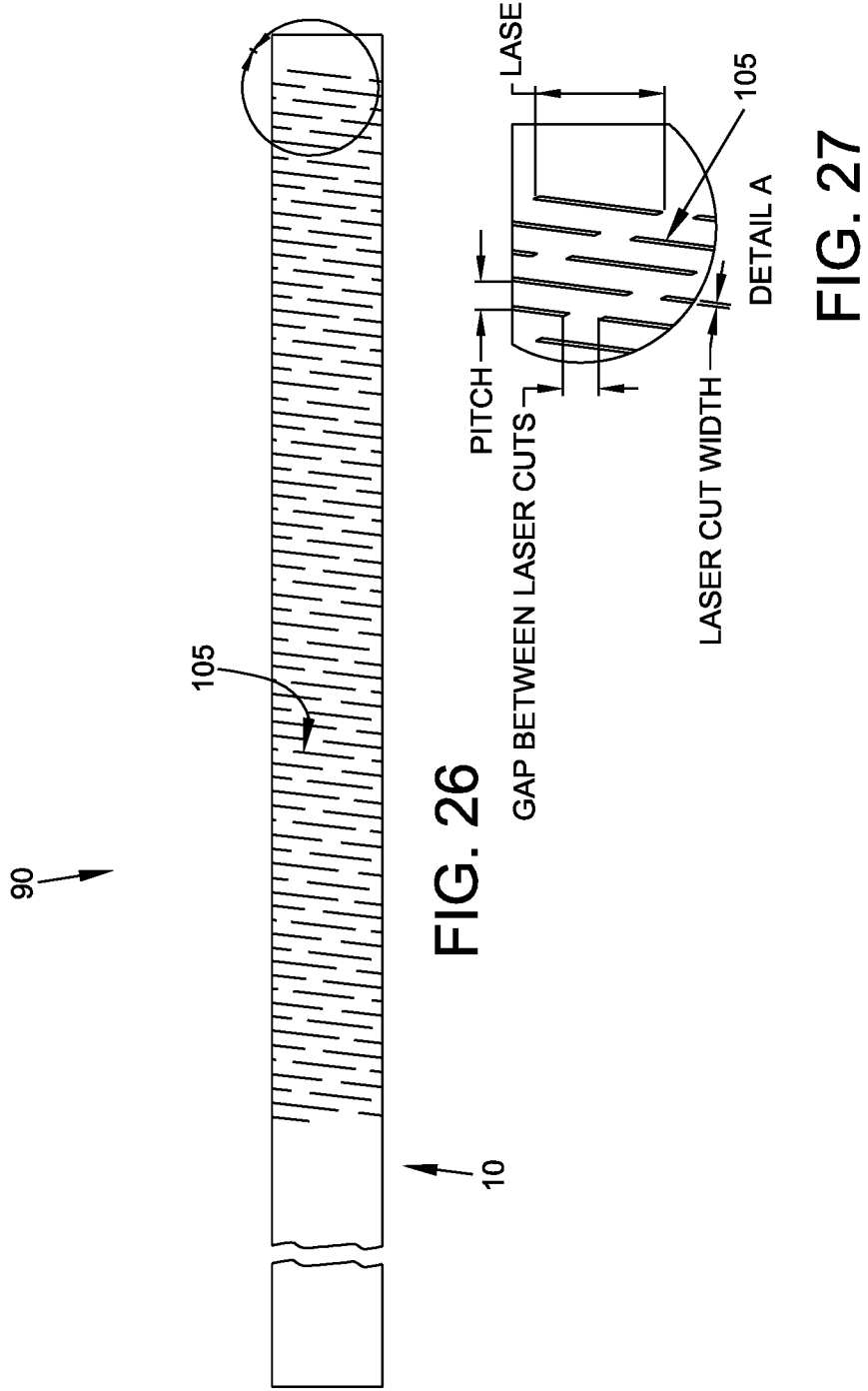

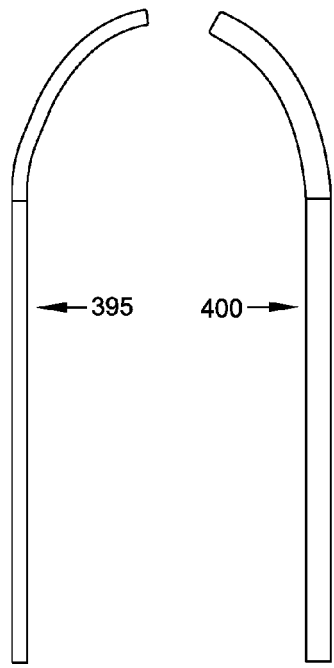
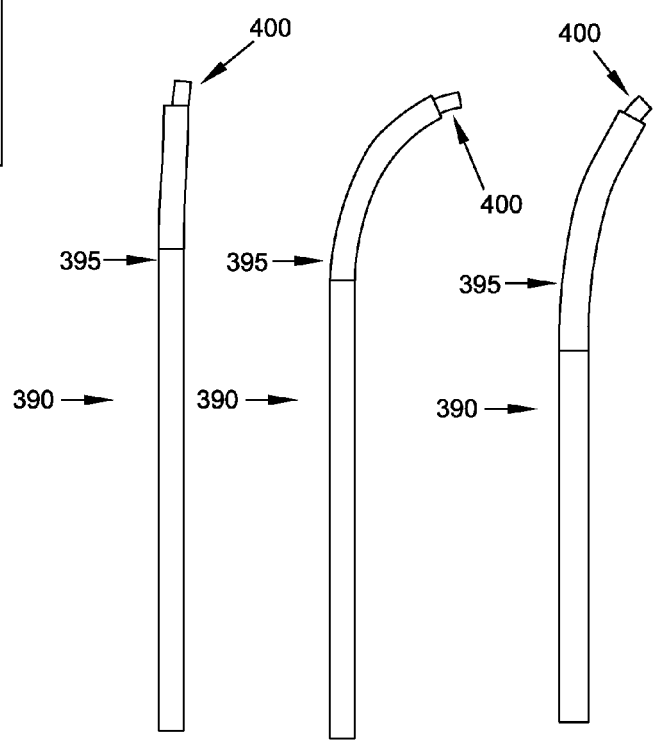
FIG. 47  FIG. 48  FIG. 49  FIG. 49A

DETAIL A

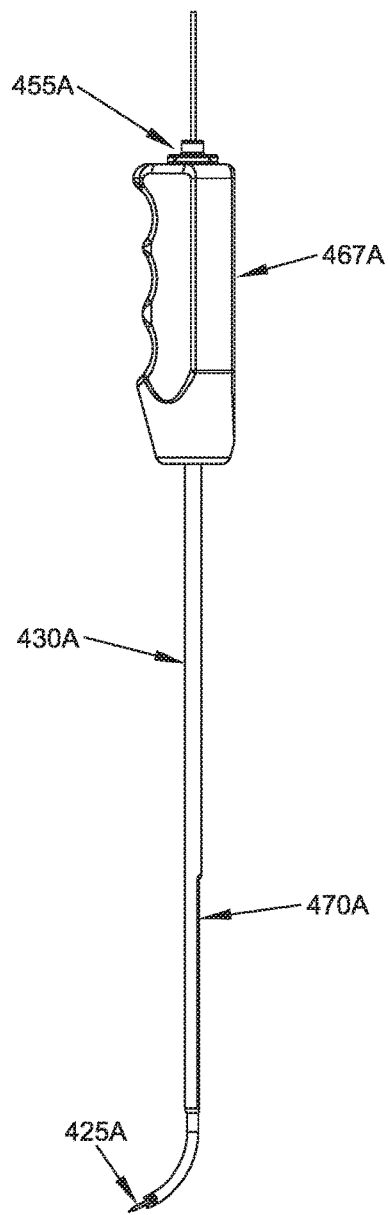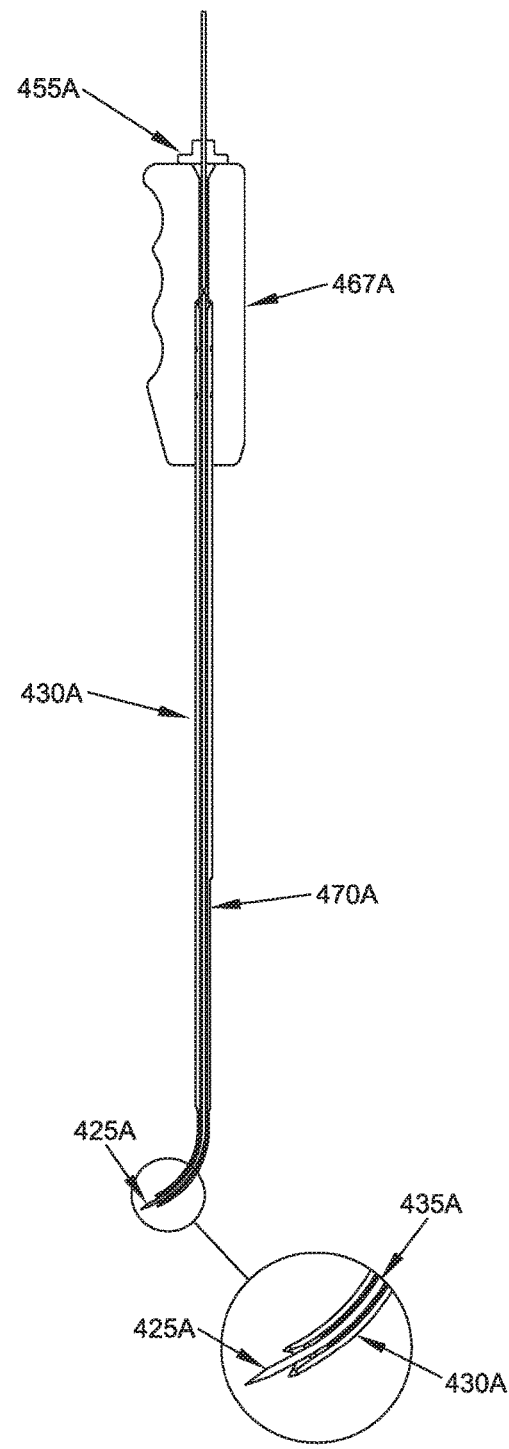
FIG. 60A
FIG. 60B

FLEXIBLE DRILL BIT AND ANGLED DRILL GUIDE FOR USE WITH THE SAME

REFERENCE TO PENDING PRIOR PATENT APPLICATIONS

This patent application:

(i) is a continuation-in-part of pending prior U.S. patent application Ser. No. 13/735,806, filed Jan. 7, 2013 by Pivot Medical, Inc. and J. Brook Burley et al. for FLEXIBLE DRILL BIT, which patent application claims benefit of prior U.S. Provisional Patent Application Ser. No. 61/583,265, filed Jan. 5, 2012 by J. Brook Burley et al. for FLEXIBLE DRILL BIT;

(ii) is a continuation-in-part of pending prior U.S. patent application Ser. No. 13/764,565, filed Feb. 11, 2013 by Pivot Medical, Inc. and J. Brook Burley et al. for FLEXIBLE DRILL BIT AND ANGLED DRILL GUIDE FOR USE WITH THE SAME, which patent application claims benefit of prior U.S. Provisional Patent Application Ser. No. 61/596,993, filed Feb. 9, 2012 by J. Brook Burley et al. for ANGLED DRILL GUIDE; and (iii) claims benefit of prior U.S. Provisional Patent Application Ser. No. 62/201,677, filed Aug. 6, 2015 by Pivot Medical, Inc. and J. Brook Burley et al. for FLEXIBLE DRILL BIT AND ANGLED DRILL GUIDE FOR USE WITH THE SAME.

The five (5) above-identified patent applications are hereby incorporated herein by reference.

FIELD OF THE INVENTION

This invention relates to surgical methods and apparatus in general, and more particularly to methods and apparatus for drilling a hole in bone.

BACKGROUND OF THE INVENTION

The General Trend Toward Treating Joint Pathologies Using Minimally-Invasive, and Earlier, Interventions The current trend in orthopedic surgery is to treat joint pathologies using minimally-invasive techniques. Such minimally-invasive, "keyhole" surgeries generally offer numerous advantages over traditional, "open" surgeries, including reduced trauma to tissue, less pain for the patient, faster recuperation times, etc.

By way of example but not limitation, it is common to re-attach ligaments in the shoulder joint using minimally-invasive, "keyhole" techniques which do not require laying open the capsule of the shoulder joint. By way of further example but not limitation, it is also common to repair torn meniscal cartilage in the knee joint, and/or to replace ruptured ACL ligaments in the knee joint, using minimally-invasive, keyhole techniques.

While such minimally-invasive approaches can require additional training on the part of the surgeon, such procedures generally offer substantial advantages for the patient and have now become standard procedures for treating many shoulder joint and knee joint pathologies.

In addition to the foregoing, in view of the inherent advantages and widespread availability of minimally-invasive approaches for treating pathologies of the shoulder joint and the knee joint, the current trend is to provide such treatment much earlier in the lifecycle of the pathology, so as to address patient pain and so as to reduce the likelihood of exacerbating the pathology itself. This is in marked contrast to traditional surgical practices, which generally dictated postponing surgical procedures for as long as possible so as to spare the patient from the substantial trauma generally associated with invasive surgery.

Treatment for Pathologies of the Hip Joint

Unfortunately, minimally-invasive treatments for pathologies of the hip joint have lagged far behind minimally-invasive treatments for pathologies of the shoulder joint and the knee joint. This is generally due to (i) the complex geometry of the hip joint itself, and (ii) the nature and location of the pathologies which are typically encountered in the hip joint.

More particularly, the hip joint is generally considered to be a "tight" joint, in the sense that there is relatively little room to maneuver within the confines of the joint itself. This is in marked contrast to the shoulder joint and the knee joint, which are generally considered to be relatively "spacious" joints (at least when compared to the hip joint). As a result, it is generally relatively difficult for surgeons to perform minimally-invasive procedures on the hip joint.

Furthermore, the pathways and approaches for entering the interior of the hip joint (i.e., the natural pathways which exist between adjacent bones and/or delicate neurovascular structures) are generally much more limited for the hip joint than for the shoulder joint or the knee joint. This limited access further complicates a surgeon's ability to effectively perform minimally-invasive procedures on the hip joint.

In addition to the foregoing, the nature and location of the pathologies of the hip joint also complicate a surgeon's ability to perform minimally-invasive procedures on the hip joint. By way of example but not limitation, consider a typical labrum tear or detachment in the hip joint. In this situation, instruments must generally be introduced into the joint space at an angle of approach which is offset from the angle at which the instrument addresses the joint anatomy. This makes drilling into bone, for example, a significantly more complicated procedure than in a case where the angle of approach is effectively aligned with the angle at which the instrument addresses the joint anatomy, such as is frequently the case in the shoulder joint. Furthermore, since the working space within the hip joint is typically extremely limited, it is even more difficult to properly adjust the alignment of surgical instruments (e.g., a drill) where the angle of approach is not aligned with the optimal angle for the instrument to address the joint anatomy.

As a result of the foregoing, minimally-invasive hip joint procedures are still relatively difficult to perform and hence less common in practice. Consequently, patients are typically forced to manage and endure their hip pain for as long as possible, until a resurfacing procedure or a partial or total hip replacement procedure can no longer be avoided. These resurfacing or replacement procedures are generally then performed as a highly-invasive, open procedure, replete with all of the disadvantages associated with highly-invasive, open procedures.

As a result, there is, in general, a pressing need for improved methods and apparatus for treating pathologies of the hip joint.

More particularly, there is a pressing need for improved methods and apparatus for introducing instruments into the joint space where the instruments will address the joint anatomy at an angle which is offset from the angle of approach. By way of example but not limitation, in some cases it may be desirable to drill into bone at an angle which is offset from the angle at which the drill is inserted into the joint space, in order to create a hole in the bone at an optimum location, e.g., at an optimum location to receive a suture anchor for use in effecting a labral repair.

SUMMARY OF THE PRESENT INVENTION

These and other objects of the present invention are addressed by the provision and use of a new flexible drill bit and a new angled drill guide (i.e., a curved drill guide) for use with the same, which may be used for drilling a hole in bone (or another material) where the flexible drill bit will enter the bone at an angle which is offset from the angle of approach.

The flexible drill bit and angled drill guide are particularly advantageous in situations where it is desirable to pass the drill bit into a joint in a curved configuration, such as where the drill bit is to be inserted into the joint through a curved guide or cannula.

In accordance with the present invention, the flexible drill bit is constructed so that it is flexible enough to bend into a curved state, yet strong enough to transmit the torsional forces required for drilling into bone (or another material).

And the angled drill guide is constructed so that it is able to support the flexible drill bit while the flexible drill bit is in its curved state and drilling into a target material (e.g., bone).

In one preferred form of the present invention, there is provided a flexible drill bit comprising:
  a proximal shaft portion for connecting to a source of turning;
  a distal cutting tip portion for boring into a material; and
  an intermediate shaft portion extending between the proximal shaft portion and the distal cutting tip portion, the intermediate shaft portion being characterized by (i) sufficient longitudinal flexibility so as to permit the flexible drill bit to be passed along a curve, and (ii) sufficient torsional strength to permit the flexible drill bit to bore into the material.

In another preferred form of the present invention, there is provided a method for forming a hole in a material, the method comprising:
  providing a flexible drill bit comprising:
    a proximal shaft portion for connecting to a source of turning;
    a distal cutting tip portion for boring into a material; and
    an intermediate shaft portion extending between the proximal shaft portion and the distal cutting tip portion, the intermediate shaft portion being characterized by (i) sufficient longitudinal flexibility so as to permit the flexible drill bit to be passed along a curve, and (ii) sufficient torsional strength to permit the flexible drill bit to bore into the material;
  advancing the flexible drill bit to the material along a first angle of approach;
  contacting the material at a second angle of approach; and
  turning the flexible drill bit so as to form a hole in the material.

In another preferred form of the present invention, there is provided apparatus for drilling a hole in material, the apparatus comprising:
  an angled drill guide comprising a curved distal section, a less-curved proximal section, and a lumen extending therebetween, wherein the less-curved proximal section comprises a flat extending therealong for reducing the effective diameter of the less-curved proximal section so as to minimize interference between the angled drill guide and the side wall of an access cannula.

In another preferred form of the present invention, there is provided apparatus for drilling a hole in material, the apparatus comprising:
  an angled drill guide comprising a curved distal section, a less-curved proximal section, and a lumen extending therebetween, wherein the curved distal section comprises first and second teeth extending distally therefrom, wherein the first tooth is set at the outer perimeter of the curve of the curved distal section, and wherein the second tooth is set at the inner perimeter of the curve of the curved distal section.

In another preferred form of the present invention, there is provided apparatus for drilling a hole in material, the apparatus comprising:
  an angled drill guide comprising a curved distal section, a less-curved proximal section, and a lumen extending therebetween, wherein the curved distal section comprises at least one window extending through the side wall thereof, and at least one side cut communicating with the at least one window and extending therefrom, so as to allow a user to view a flexible drill bit disposed within the lumen of the angled drill guide.

In another preferred form of the present invention, there is provided apparatus for drilling a hole in material, the apparatus comprising:
  an angled drill guide comprising a curved distal section, a less-curved proximal section, and a lumen extending therebetween, wherein the curved distal section comprises a dimple for effectively narrowing the lumen of the angled drill guide opposite to the curve of the angled drill guide, whereby to angularly re-align a flexible drill bit exiting the distal section of the angled drill guide.

In another preferred form of the present invention, there is provided apparatus for drilling a hole in material, the apparatus comprising:
  an angled drill guide comprising a curved distal section, a less-curved proximal section, and a lumen extending therebetween, wherein the lumen tapers inwardly in the curved distal section so as to re-center a flexible drill bit exiting the distal section of the angled drill guide.

In another preferred form of the present invention, there is provided apparatus for drilling a hole in material, the apparatus comprising:
  an angled drill guide comprising a curved distal section, a less-curved proximal section, and a lumen extending therebetween, wherein the curved distal section comprises compound curves so as to re-align a flexible drill bit exiting the distal section of the angled drill guide.

In another preferred form of the present invention, there is provided apparatus for drilling a hole in material, the apparatus comprising:
  an angled drill guide comprising a curved distal section, a less-curved proximal section, and a lumen extending therebetween; and
  a handle mounted to the angled drill guide so that the handle is offset from the longitudinal axis of the less-curved proximal section of the angled drill guide and aligned with the curved distal section of the angled drill guide, whereby to allow the user to push the distal end of the angled drill guide directly against the outer surface of the material which is to be drilled.

In another preferred form of the present invention, there is provided apparatus for drilling a hole in material, the apparatus comprising:

an articulating angled drill guide comprising a curved inner sheath and a less-curved outer sheath, wherein the curved inner sheath is telescopically received within the less-curved outer sheath.

In another preferred form of the present invention, there is provided apparatus for drilling a hole in material, the apparatus comprising:

an articulating angled drill guide comprising a curved inner sheath and a curved outer sheath, wherein the curved inner sheath is slidably received within the curved outer sheath.

In another preferred form of the present invention, there is provided a friction-reducing flexible drill bit comprising a flexible drill bit having a low-friction coating formed thereon.

In another preferred form of the present invention, there is provided a method for drilling a hole in material, the method comprising:

providing an angled drill guide comprising a curved distal section, a less-curved proximal section, and a lumen extending therebetween, wherein the less-curved proximal section comprises a flat extending therealong for reducing the effective diameter of the less-curved proximal section so as to minimize interference between the angled drill guide and the side wall of an access cannula;

positioning the angled drill guide against the material to be drilled; and advancing a flexible drill bit through the angled drill guide and drilling into the material.

In another preferred form of the present invention, there is provided a method for drilling a hole in material, the method comprising:

providing an angled drill guide comprising a curved distal section, a less-curved proximal section, and a lumen extending therebetween, wherein the curved distal section comprises first and second teeth extending distally therefrom, wherein the first tooth is set at the outer perimeter of the curve of the curved distal section, and wherein the second tooth is set at the inner perimeter of the curve of the curved distal section;

positioning the angled drill guide against the material to be drilled; and advancing a flexible drill bit through the angled drill guide and drilling into the material.

In another preferred form of the present invention, there is provided a method for drilling a hole in material, the method comprising:

providing an angled drill guide comprising a curved distal section, a less-curved proximal section, and a lumen extending therebetween, wherein the curved distal section comprises at least one window extending through the side wall thereof, and at least one side cut communicating with the at least one window and extending therefrom, so as to allow a user to view a flexible drill bit disposed within the lumen of the angled drill guide;

positioning the angled drill guide against the material to be drilled; and advancing a flexible drill bit through the angled drill guide and drilling into the material.

In another preferred form of the present invention, there is provided a method for drilling a hole in material, the method comprising:

providing an angled drill guide comprising a curved distal section, a less-curved proximal section, and a lumen extending therebetween, wherein the curved distal section comprises a dimple for effectively narrowing the lumen of the angled drill guide opposite to the curve of the angled drill guide, whereby to angularly re-align a flexible drill bit exiting the distal section of the angled drill guide;

positioning the angled drill guide against the material to be drilled; and advancing a flexible drill bit through the angled drill guide and drilling into the material.

In another preferred form of the present invention, there is provided a method for drilling a hole in material, the method comprising:

providing an angled drill guide comprising a curved distal section, a less-curved proximal section, and a lumen extending therebetween; and a handle mounted to the angled drill guide so that the handle is offset from the longitudinal axis of the less-curved proximal section of the angled drill guide and aligned with the curved distal section of the angled drill guide, whereby to allow the user to push the distal end of the angled drill guide directly against the outer surface of the material which is to be drilled;

positioning the angled drill guide against the material to be drilled; and advancing a flexible drill bit through the angled drill guide and drilling into the material.

In another preferred form of the present invention, there is provided a method for drilling a hole in material, the method comprising:

providing an articulating angled drill guide comprising a curved inner sheath and a less-curved outer sheath, wherein the curved inner sheath is telescopically received within the less-curved outer sheath;

positioning the angled drill guide against the material to be drilled; and advancing a flexible drill bit through the angled drill guide and drilling into the material.

In another preferred form of the present invention, there is provided a method for drilling a hole in material, the method comprising:

providing an articulating angled drill guide comprising a curved inner sheath and a curved outer sheath, wherein the curved inner sheath is slidably received within the curved outer sheath;

positioning the angled drill guide against the material to be drilled; and advancing a flexible drill bit through the angled drill guide and drilling into the material.

In another preferred form of the present invention, there is provided a method for forming a hole in a material, the method comprising:

providing a friction-reducing flexible drill bit comprising a flexible drill bit having a low-friction coating formed thereon; and turning the flexible drill bit so as to form a hole in the material.

In another preferred form of the present invention, there is provided apparatus for drilling a hole in material, the apparatus comprising:

an angled drill guide comprising a curved distal section, a less-curved proximal section, and a lumen extending therebetween, wherein the lumen narrows at a first location along the curved distal section;

a flexible drill bit disposed within the lumen of the angled drill guide, wherein the flexible drill bit comprises a diametrical enlargement at a second location proximal to the first location.

In another preferred form of the present invention, there is provided a method for drilling a hole in material, the method comprising:

providing apparatus comprising:

an angled drill guide comprising a curved distal section, a less-curved proximal section, and a lumen extending therebetween, wherein the lumen narrows at a first location along the curved distal section;

a flexible drill bit disposed within the lumen of the angled drill guide, wherein the flexible drill bit comprises a diametrical enlargement at a second location proximal to the first location;

positioning the angled drill guide against the material to be drilled; and advancing the flexible drill bit through the angled drill guide and drilling into the material.

In another preferred form of the present invention, there is provided apparatus for drilling a hole in material, the apparatus comprising:

an angled drill guide comprising a curved distal section, a less-curved proximal section, and a lumen extending therebetween, wherein the less-curved proximal section is mounted to a handle;

a flexible drill bit disposed within the lumen of the angled drill guide; and a stop secured to the flexible drill bit and selectively engaging the handle so as to limit longitudinal movement of the flexible drill bit relative to the handle.

In another preferred form of the present invention, there is provided a method for drilling a hole in material, the method comprising:

providing apparatus comprising:

an angled drill guide comprising a curved distal section, a less-curved proximal section, and a lumen extending therebetween, wherein the less-curved proximal section is mounted to a handle;

a flexible drill bit disposed within the lumen of the angled drill guide; and a stop secured to the flexible drill bit and selectively engaging the handle so as to limit longitudinal movement of the flexible drill bit relative to the handle;

positioning the angled drill guide against the material to be drilled; and advancing the flexible drill bit through the angled drill guide and drilling into the material.

In another preferred form of the present invention, there is provided apparatus for drilling a hole in material, the apparatus comprising:

an angled drill guide comprising:

an inner component comprising a curved distal section, a less-curved proximal section, an intermediate flexible section extending between the curved distal section and the less-curved proximal section, and a lumen extending through the curved distal section, the intermediate flexible section and the less-curved proximal section; and an outer component comprising a distal end, a proximal end and a lumen extending therebetween;

the inner component being receivable within the lumen of the outer component and the inner component and outer component being selectively movable such that (i) the intermediate flexible section of the inner component is received within the lumen of the outer component, and (ii) the intermediate flexible section of the inner component is disposed distal to the outer component.

In another preferred form of the present invention, there is provided a method for drilling a hole in material, the method comprising:

providing apparatus comprising:

an angled drill guide comprising:

an inner component comprising a curved distal section, a less-curved proximal section, an intermediate flexible section extending between the curved distal section and the less-curved proximal section, and a lumen extending through the curved distal section, the intermediate flexible section and the less-curved proximal section; and an outer component comprising a distal end, a proximal end and a lumen extending therebetween;

the inner component being receivable within the lumen of the outer component and the inner component and outer component being selectively movable such that (i) the intermediate flexible section of the inner component is received within the lumen of the outer component, and (ii) the intermediate flexible section of the inner component is disposed distal to the outer component; and a flexible drill bit disposed within the lumen of the inner component;

positioning the angled drill guide against the material to be drilled; and advancing the flexible drill bit through the angled drill guide and drilling into the material.

In another preferred form of the present invention, there is provided apparatus for forming a hole in bone, the apparatus comprising:

a flexible drill bit comprising Nitinol having an Af temperature which is greater than the highest temperature that the flexible drill bit will reach during drilling.

In another preferred form of the present invention, there is provided a method for forming a hole in a material, the method comprising:

providing a flexible drill bit comprising Nitinol having an Af temperature which is greater than the highest temperature that the flexible drill bit will reach during drilling;

advancing the flexible drill bit to the material along a first angle of approach;

contacting the material at a second angle of approach; and turning the flexible drill bit so as to form a hole in the material.

In another preferred form of the present invention, there is provided a method for forming a Nitinol flexible drill bit, the method comprising:

providing a Nitinol wire workpiece having an initial Af range of approximately 5-18 degrees C.;

machining the Nitinol wire workpiece to form a Nitinol flexible drill bit; and heat treating the Nitinol flexible drill bit so as to raise its Af range to an elevated Af range of approximately 42-54 degrees C.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIG. 14 is a schematic view showing another form of flexible drill bit formed in accordance with the present invention;

FIG. 15 is a schematic view showing still another form of flexible drill bit formed in accordance with the present invention;

FIGS. 16-19 are schematic cross-sectional views taken along lines A-A, B-B, C-C and D-D, respectively, of FIG. 15 in one form of the invention;

FIGS. 20-23 are schematic cross-sectional views taken along lines A-A, B-B, C-C and D-D, respectively, of FIG. 15 in another form of the invention;

FIG. 24 is a schematic view showing another form of flexible drill bit formed in accordance with the present invention;

FIG. 25 is a schematic cross-sectional view taken along line A-A of FIG. 24;

FIG. 26 is a schematic view showing still another form of flexible drill bit formed in accordance with the present invention;

FIG. 27 is an enlarged schematic view showing selected portions of the flexible drill bit of FIG. 26;

FIGS. 47-49 and 49A are schematic views showing still another novel articulating angled drill guide formed in accordance with the present invention;

FIGS. 60A-60E are schematic views showing a novel flexible drill bit formed in accordance with the present invention, and a novel angled drill guide formed in accordance with the present invention;

DETAILED DESCRIPTION OF THE PREFERRED EMBODIMENTS

Flexible Drill Bit Having a "Unibody" Construction

Figure 1:
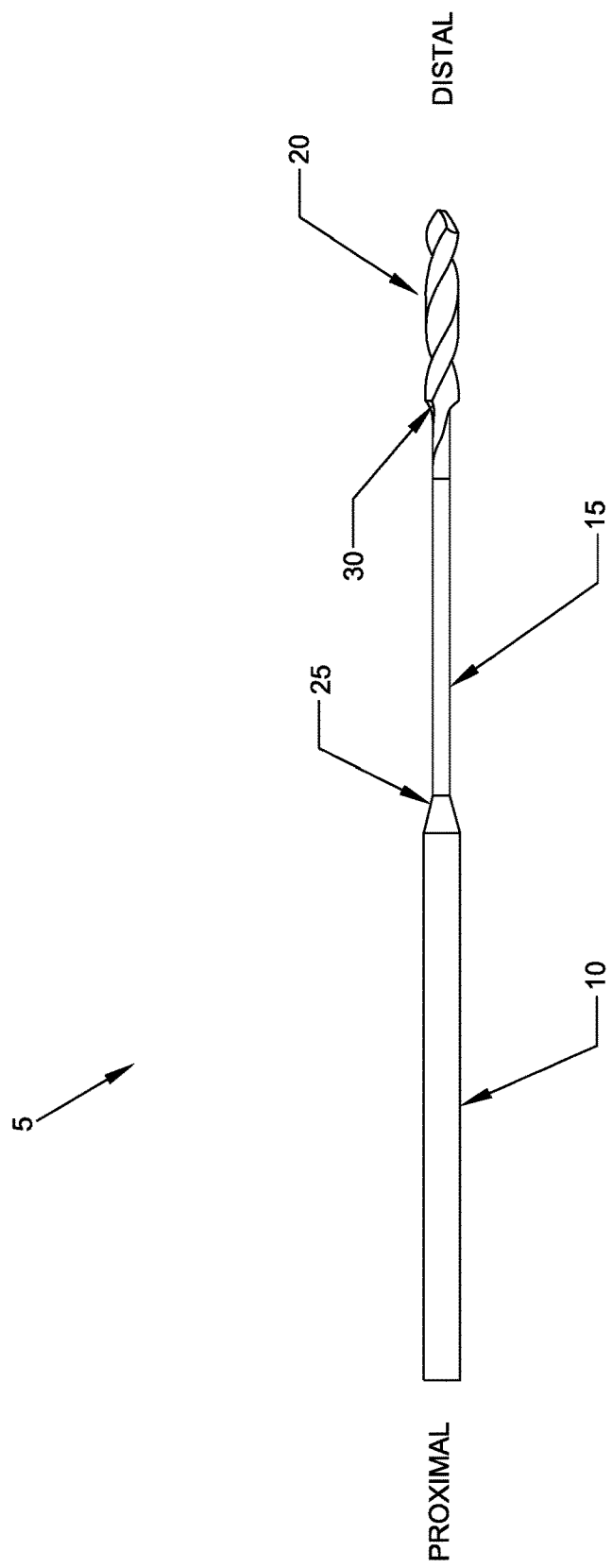
FIG. 1 is a schematic view showing a flexible drill bit formed in accordance with the present invention.
Figure 2:
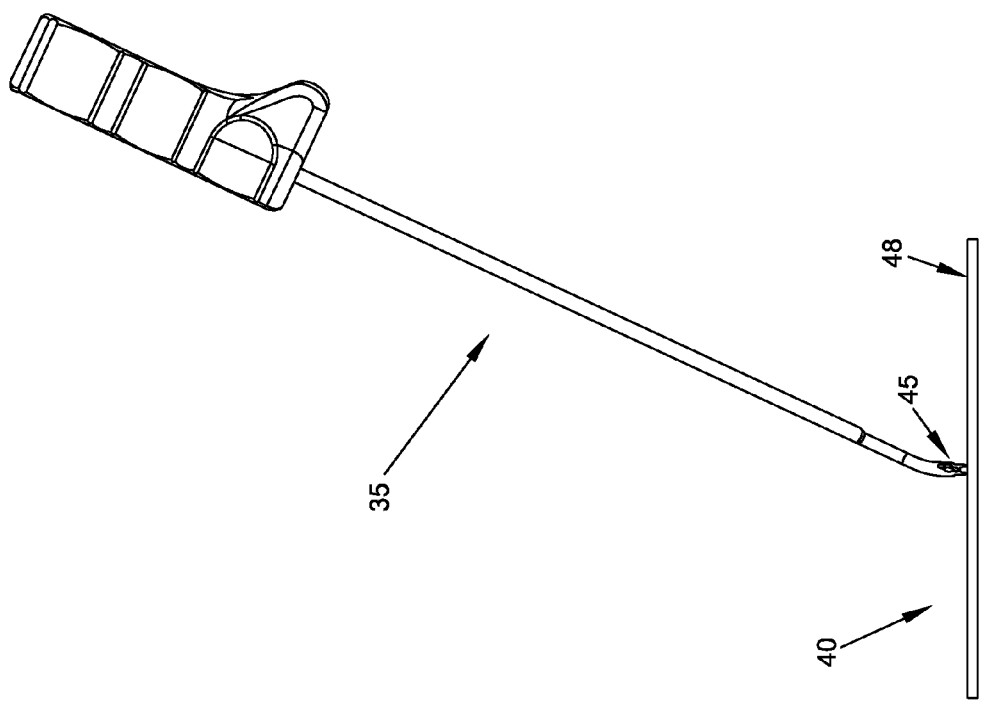
FIGS. 2-5 are schematic views showing the flexible drill bit of FIG. 1 being used in conjunction with a curved drill guide to form a hole in bone.
Figure 3:
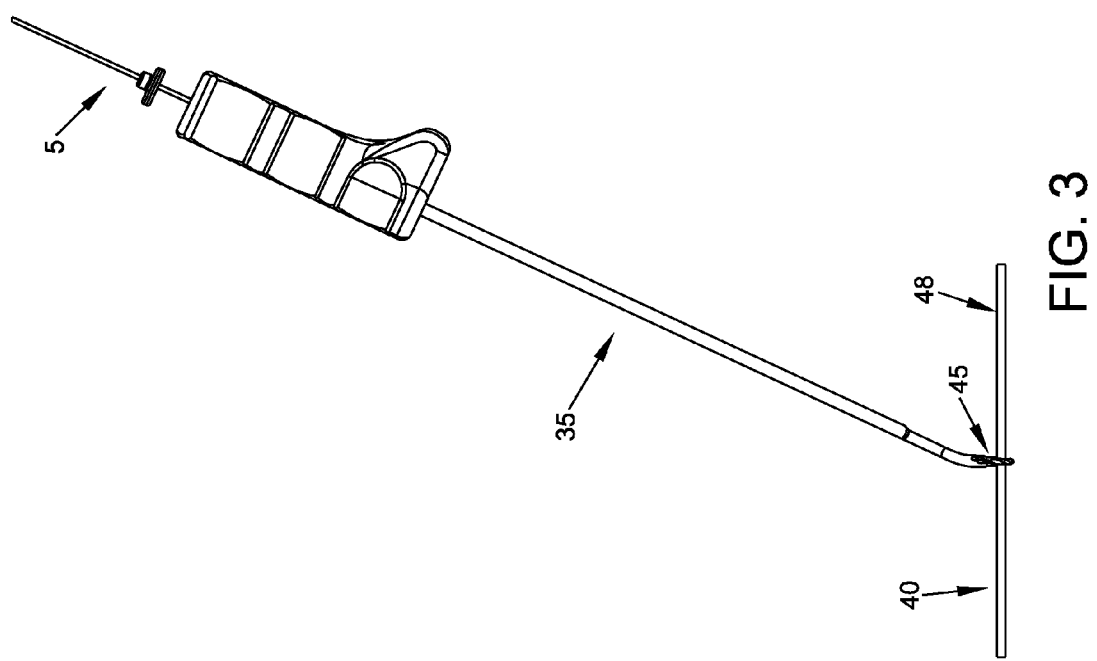
Figure 4:
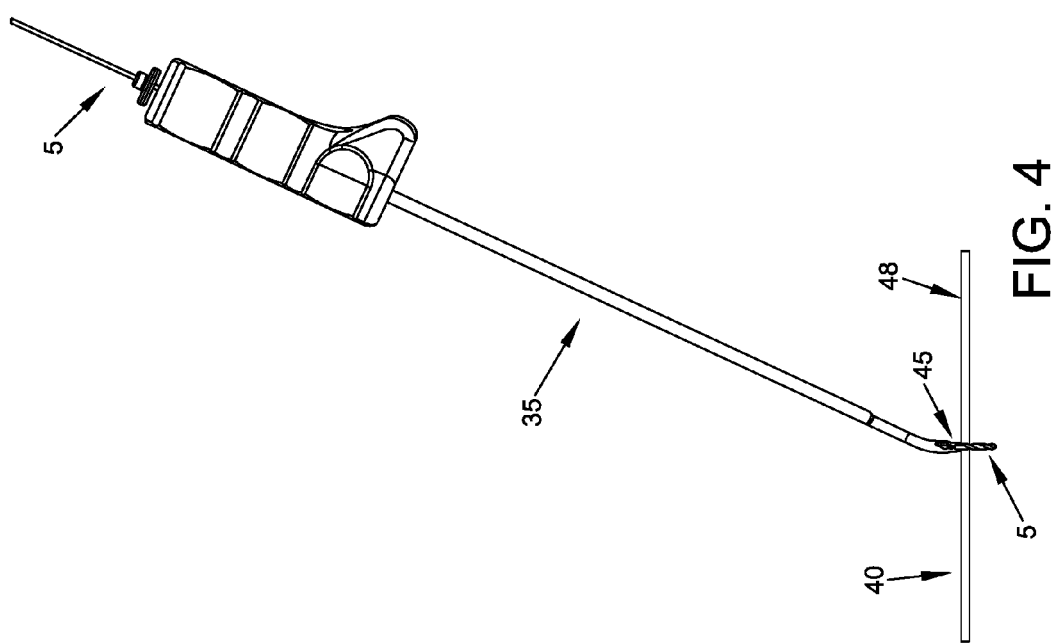

Looking first at FIG. 1, there is a shown a flexible drill bit 5 formed in accordance with the present invention. Flexible drill bit 5 comprises three sections, i.e., a full diameter shaft portion 10, a reduced diameter shaft portion 15, and a fluted cutting tip portion 20. Full diameter shaft portion 10, reduced diameter shaft portion 15, and fluted cutting tip portion 20 are all formed integral with one another so as to create a flexible drill bit having a "unibody" construction. If desired, a transition area 25 may be formed between full diameter shaft portion 10 and reduced diameter shaft portion 15, and/or a transition area 30 may be formed between reduced diameter shaft portion 15 and fluted cutting tip portion 20.

The "unibody" construction eliminates the need for a mechanical joint connecting the cutting tip of the flexible drill bit (e.g., fluted cutting tip portion 20) to the flexible portion of the flexible drill bit (e.g., reduced diameter shaft portion 15), thereby eliminating a possible point of failure. Such a failure of a mechanical joint can be particularly problematic if the mechanical joint were to fail below the surface of the bone (i.e., subchondral); in this scenario, it would be unlikely that the portion of the drill bit left in the bone could be recovered. Thus, the possible failure of such a mechanical joint creates a serious clinical concern. In addition, the "unibody" construction eliminates the need for a mechanical joint connecting the flexible portion of the flexible drill bit (e.g., reduced diameter shaft portion 15) to the full diameter shaft portion (e.g., full diameter shaft portion 10) of the flexible drill bit, thus eliminating another possible point of failure.

The flexible drill bit may comprise a material such as Nitinol, stainless steel, titanium, or other appropriate material, but is preferably Nitinol.

The reduced diameter shaft portion 15 of flexible drill bit 5 provides flexibility in that portion of the drill bit while still providing the torsional strength needed to drill into bone. The diameter of the reduced diameter shaft portion 15 is preferably approximately 20-40% smaller than the diameter of the full diameter shaft portion 10, and more preferably approximately 25% smaller than the diameter of the full diameter shaft portion 10. In an alternative embodiment, the diameter of the reduced diameter shaft portion 15 is preferably approximately 5-25% smaller than the diameter of the fluted cutting tip portion 20, and more preferably approximately 15% smaller than the diameter of the fluted cutting tip portion 20.

The transition area 30 located between fluted cutting tip portion 20 and the reduced diameter shaft portion 15, and/or the transition area 25 located between the reduced diameter shaft portion 15 and the full diameter shaft portion 10, are preferably formed so as to distribute stress, whereby to minimize the possibility of mechanical failure at the transition areas.

Full diameter shaft portion 10 provides a region, preferably at its proximal end, in which flexible drill bit 5 can be attached to a drill.

Fluted cutting tip portion 20 is preferably sufficiently rigid to form a straight hole in the target bone. To that end, the length of fluted cutting tip portion 20 must be short enough so that the fluted cutting tip portion 20 may pass through the curve of a curved drill guide or curved cannula. In one preferred embodiment, fluted cutting tip portion 20 has a length which is approximately 6 times greater than its diameter.

FIGS. 2-5 show flexible drill bit 5 being used in conjunction with a curved drill guide 35 to form a hole in a bone 40. More particularly, as seen in the figures, the distal tip 45 of curved drill guide 35 is placed against the outer surface 48 of bone 40, and then flexible drill bit 5 is passed through the lumen 50 of curved drill guide 35 and directed into bone 40 so as to make the hole in the bone at the desired location and with the desired angle.

Figure 5:
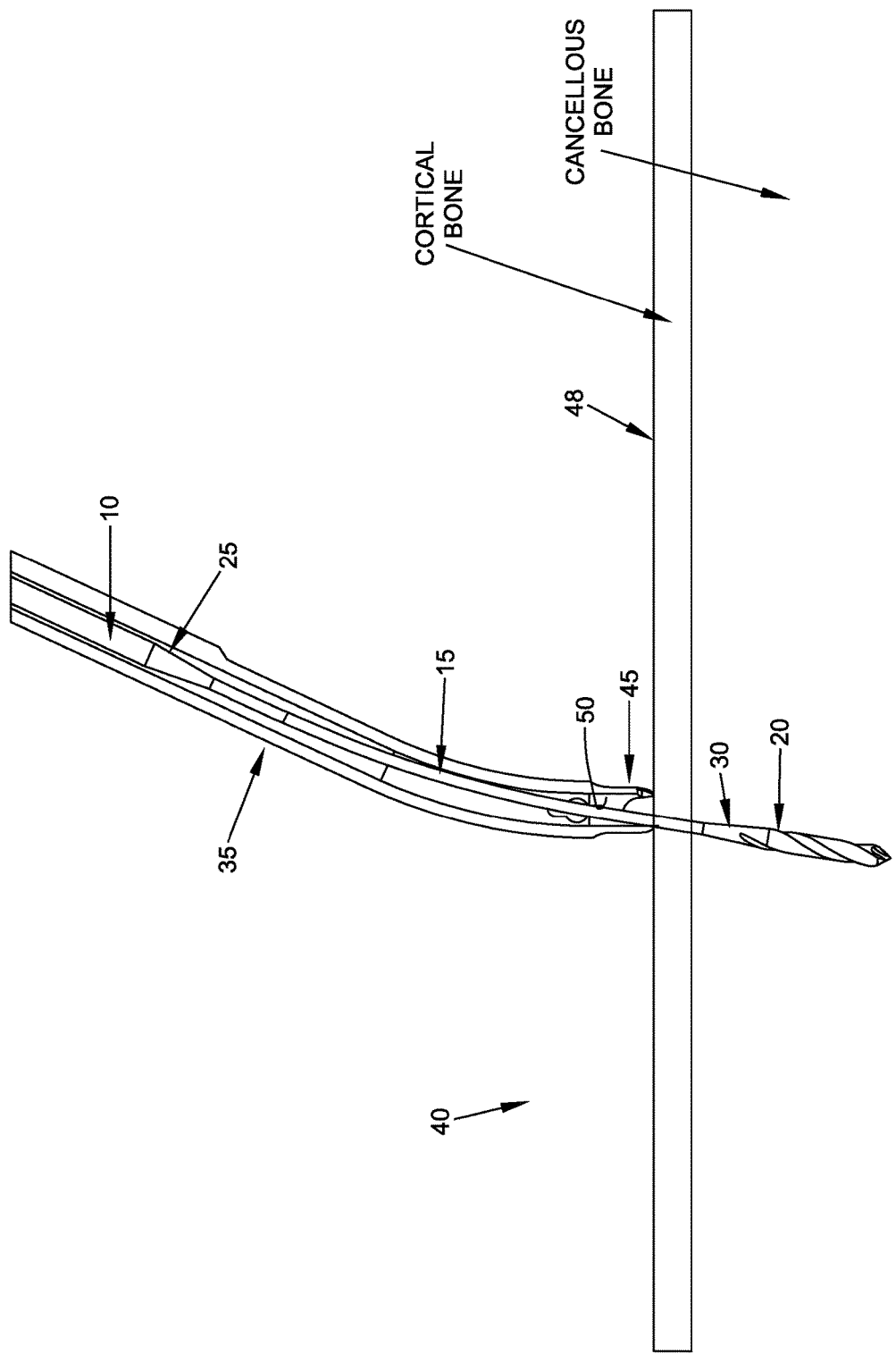

Note in FIG. 5 how the curvature of curved drill guide 35 can combine with the differences in the diameters of the reduced diameter shaft portion 15 and lumen 50 so as to result in a non-perpendicular entry of flexible drill bit 5 into the bone, even where distal tip 45 of curved drill guide 35 is disposed substantially perpendicular to outer surface 48 of the bone. In other words, the curvature of curved drill guide 35 can combine with the differences in the diameters of reduced diameter shaft portion 15 and lumen 50 so that fluted cutting tip portion 20 is not perfectly coaxial with lumen 50 as fluted cutting tip portion 20 emerges from the distal end of curved drill guide 35. It will be apparent to one skilled in the art that, depending on the bone surface contour and/or the angle of approach of curved drill guide 35, the curved drill guide 35 may not always be disposed perpendicular to outer surface 48 of the bone. In this scenario, it is typically still desirable to have the fluted cutting tip portion 20 centered and aligned with the end of the curved drill guide 35.

Figure 6:
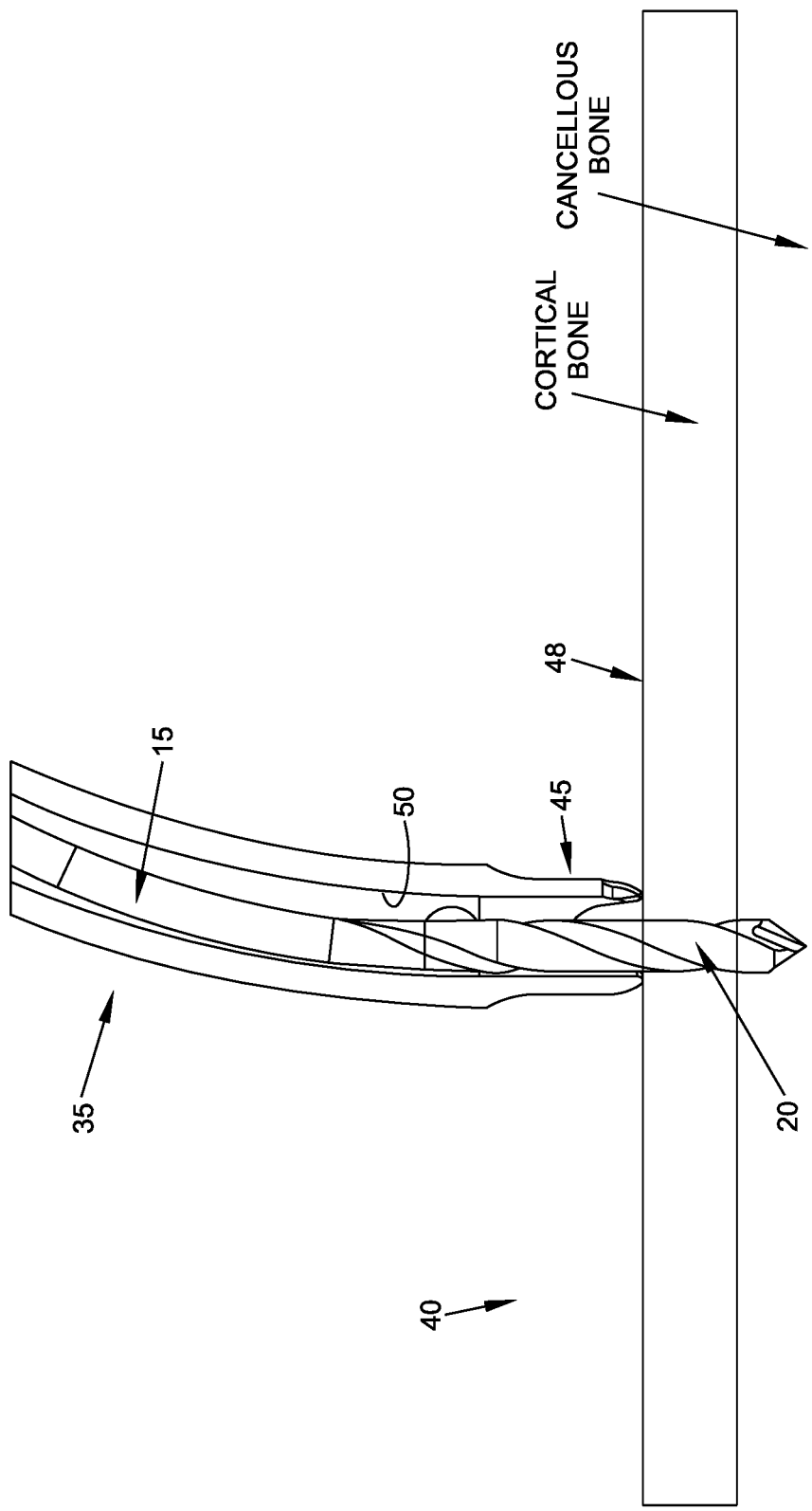
FIGS. 6 and 7 are schematic views showing another flexible drill bit formed in accordance with the present invention and being used in conjunction with a curved drill guide to form a hole in bone.
Figure 7:
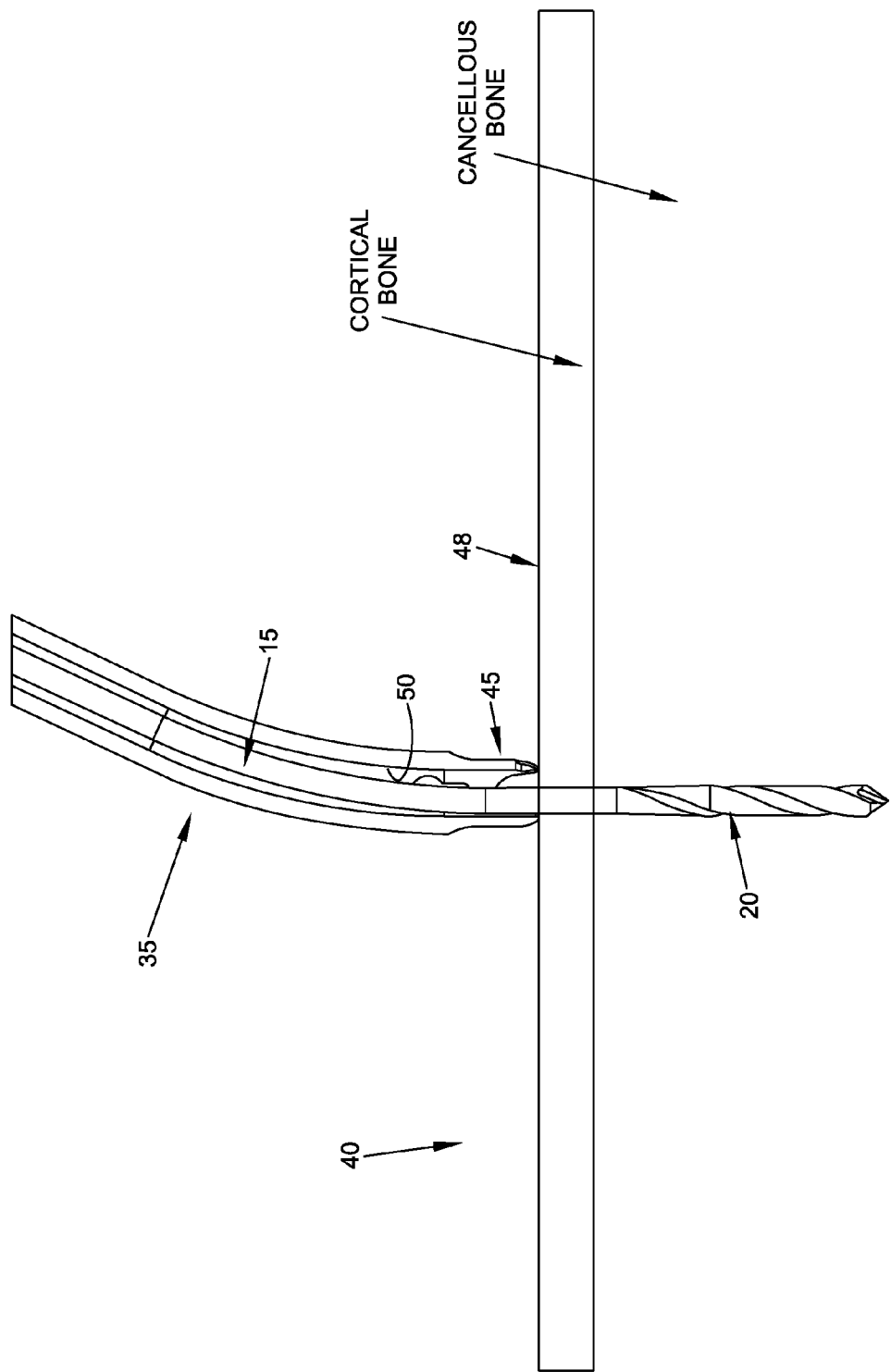

FIGS. 6 and 7 show another form of the invention where the diameter of reduced diameter shaft portion 15 is sized so as to be closer to the diameter of fluted cutting tip portion 20 and so as to be somewhat closer to the diameter of lumen 50 of curved drill guide 35. In this form of the invention, flexible drill bit 5 will tend to enter the bone closer to perpendicular. In other words, in this form of the invention, fluted cutting tip portion 20 will tend to remain more coaxial with lumen 50 as fluted cutting tip portion 20 emerges from the distal end of curved drill guide 35.

In one preferred form of the invention, full diameter shaft portion 10 has a length of approximately 12 inches and a diameter of approximately 0.063 inch; reduced diameter shaft portion 15 has a length of approximately 1.5 inches and a diameter of approximately 0.047 inch; fluted cutting tip portion 20 has a total fluted length of approximately 0.5 inch, of which approximately 0.325 inch is of constant outer diameter (OD) of approximately 0.055 inch and the remaining length of 0.175 inch tapers on the proximal end of the flutes; and curved drill guide 35 has a radius of curvature of approximately 1.25 inches, a curve of approximately 25 degrees, and a lumen 50 diameter of approximately 0.071 inch. In this preferred form of the invention, flexible drill bit 5 is capable of transmitting at least approximately 2 in-lbs (inch-pounds) of torque without failure, and more preferably approximately 3 in-lbs (inch-pounds) of torque without failure. In this configuration, fluted cutting tip portion 20 can pass through lumen 50 of curved drill guide 35. Specifically, fluted cutting tip portion 20 is substantially rigid due to its larger diameter (i.e., as compared to reduced diameter shaft portion 15); however, there is sufficient clearance between the outer diameter of fluted cutting tip portion 20 and lumen 50 so that fluted cutting tip portion 20 passes through lumen 50 without significant interference. The length of the fluted cutting tip portion 20 is preferably less than the depth of the hole which it will be used to drill. In other words, when the flexible drill bit 5 is used to form a bone hole, the entire length of the fluted cutting tip portion 20 will pass into the bone along with a portion of the reduced diameter shaft portion 15.

Figure 8:
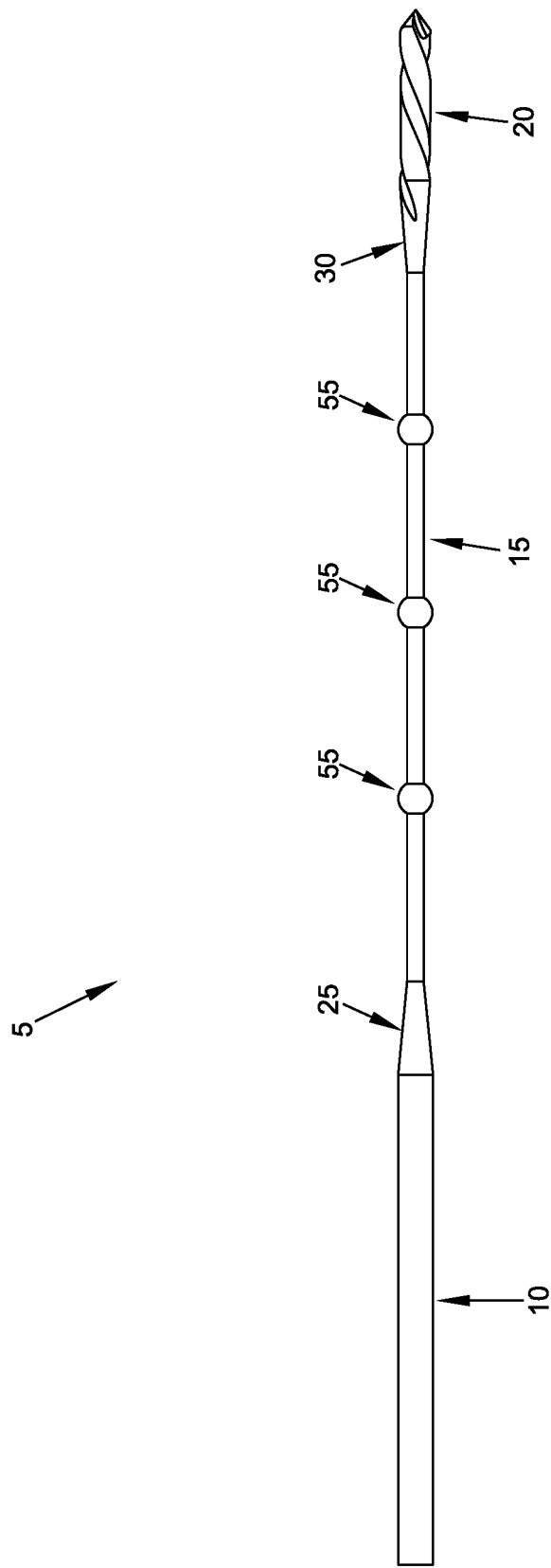
FIG. 8 is a schematic view showing still another flexible drill bit formed in accordance with the present invention.
Figure 9:
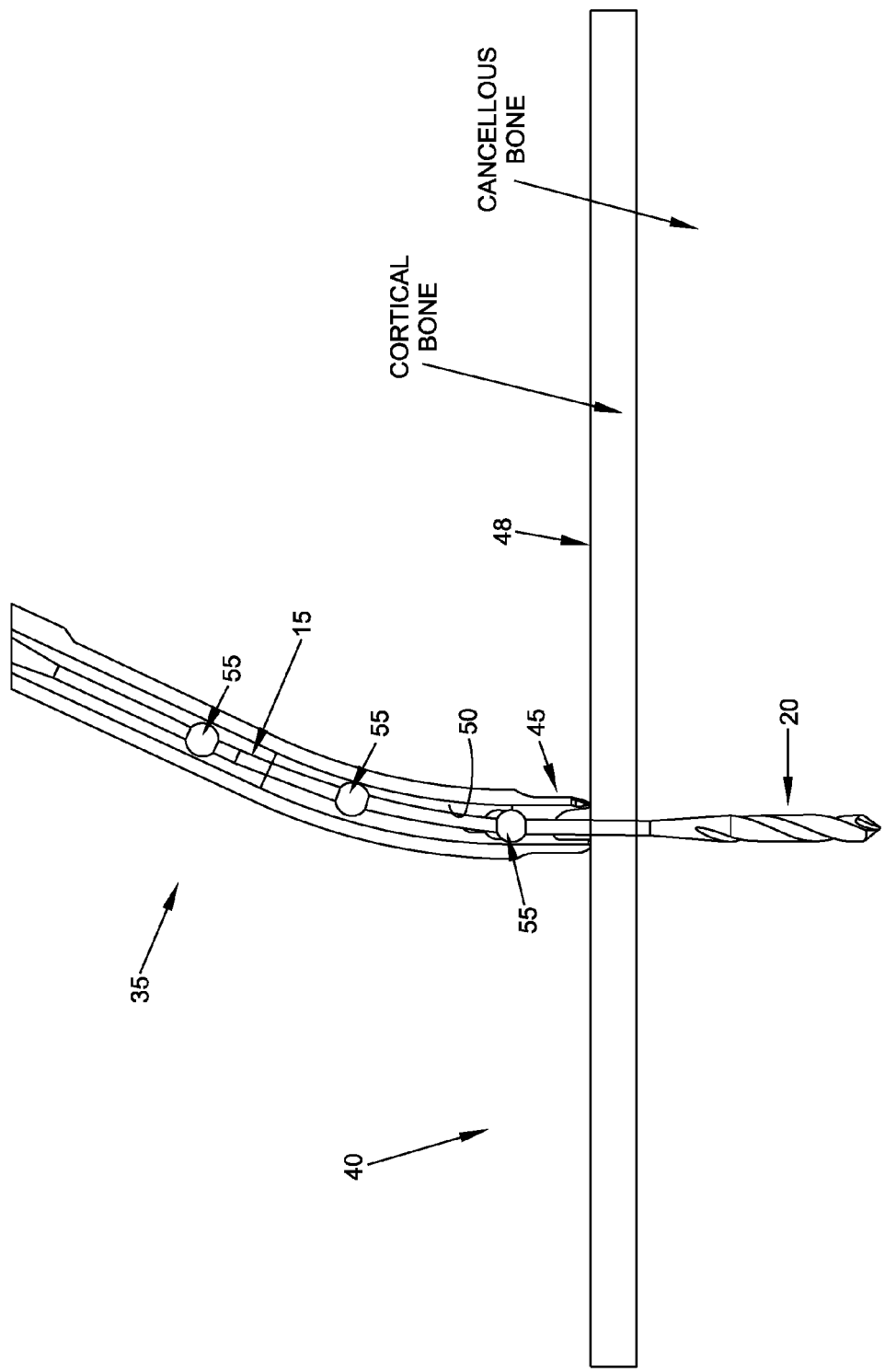
FIG. 9 is a schematic view showing the flexible drill bit of FIG. 8 being used in conjunction with a curved drill guide to form a hole in bone.

In another form of the invention, and looking now at FIGS. 8 and 9, one or more enlargements 55 may be formed on the reduced diameter shaft portion 15 of flexible drill bit 5. Enlargements 55 preferably have an outer diameter similar to the outer diameter of full diameter shaft portion 10 and thus serve to keep flexible drill bit 5 centered in lumen 50 of curved drill guide 35 even where reduced diameter shaft portion 15 has a diameter which is significantly less than the diameter of lumen 50 of curved drill guide 35. In this form of the invention, enlargements 55 will also keep flexible drill bit 5 closer to perpendicular as it enters bone 40. In other words, in this form of the invention, fluted cutting tip portion 20 will tend to remain more coaxial with lumen 50 as fluted cutting tip portion 20 emerges from the distal end of curved drill guide 35. In another embodiment, enlargements 55 have an outer diameter similar to the outer diameter of fluted cutting tip portion 20.

Figure 10:
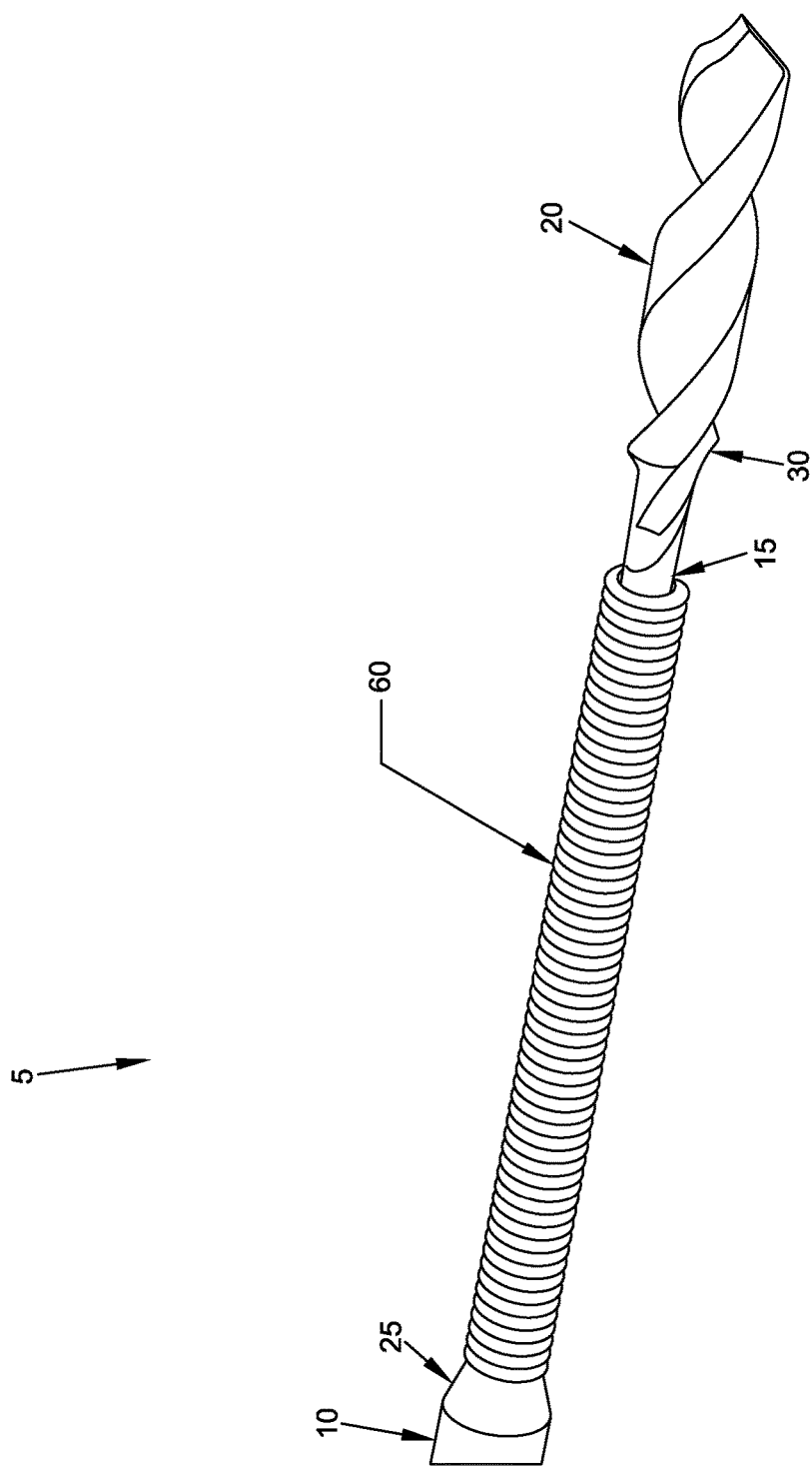
FIG. 10 is a schematic view showing the flexible drill bit of FIG. 1 with a helical coil disposed over a portion of the flexible drill bit.

In another embodiment, and looking now at FIG. 10, a helical coil 60 may be positioned over reduced diameter shaft portion 15 of flexible drill bit 5 so as to supplement the torque needed to drill into bone while still providing the flexibility needed to maneuver around a curve in a curved drill guide (e.g., curved drill guide 35) or curved cannula. Helical coil 60 also helps to keep flexible drill bit 5 centered in a curved drill guide (e.g., curved drill guide 35) and reduce the "mismatch" angle between flexible drill bit 5 and the end of curved drill guide 35.

More particularly, helical coil 60 provides additional torsional strength and increased diameter to the reduced diameter shaft portion 15 of flexible drill bit 5 without significantly reducing the flexibility of the drill bit. The increased diameter of reduced diameter shaft portion 15 of flexible drill bit 5 (due to the presence of helical coil 60) creates a close fit within the curved drill guide or curved cannula, thereby ensuring that the drill bit remains coaxial with the curved drill guide or curved cannula as the flexible drill bit emerges from the distal end of the curved drill guide or curved cannula and engages the bone (or other material) which is being drilled.

Helical coil 60 may form a close fit around reduced diameter shaft portion 15 and be sized so that it rests between transition area 25 and transition area 30. Helical coil 60 may be resilient and may be stretched slightly (in its diameter) from its unbiased condition so as to allow the helical coil to be positioned onto reduced diameter shaft portion 15; in other words, in a free condition, the helical coil 60 has an inner diameter which is smaller than the outer diameter of the reduced diameter shaft portion 15. Helical coil 60 may simply sit on reduced diameter shaft portion 15, or it may be secured to reduced diameter shaft portion 15 (e.g., at one end of helical coil 60, at both ends of helical coil 60, and/or intermediate helical coil 60, etc.). In one preferred embodiment, helical coil 60 is secured at both its ends to reduced diameter shaft portion 15 and forms a close fit with reduced diameter shaft portion 15 or is stretched slightly diametrically from its unbiased condition and then set onto reduced diameter shaft portion 15. Helical coil 60 may be secured to reduced diameter shaft portion 15 by soldering, adhesive, welding, mechanical interlock, or other appropriate attachment means. Helical coil 60 is preferably formed and positioned so that when the flexible drill bit is used to drill into bone, the helical coil will tighten onto reduced diameter shaft portion 15 during drilling. For example, if a flexible drill bit 5 rotates in a clockwise direction (when viewed from proximal to distal), the helical coil should have a counter-clockwise winding direction (again, when viewed from proximal to distal). This arrangement provides a preferred transfer of torque between reduced diameter shaft portion 15 and helical coil 60; in other words, reduced diameter shaft portion 15 and helical coil 60 share torque transmission between full diameter shaft portion 10 and fluted cutting tip portion 20.

Helical coil 60 may comprise a material such as stainless steel, Nitinol or other suitable material. Helical coil 60 may comprise a wire of round or rectangular cross-section. Although FIG. 10 depicts a closely wound helical coil (i.e., with substantially no space between the coils), an alternative embodiment comprises spacing between the coils.

Figure 11:
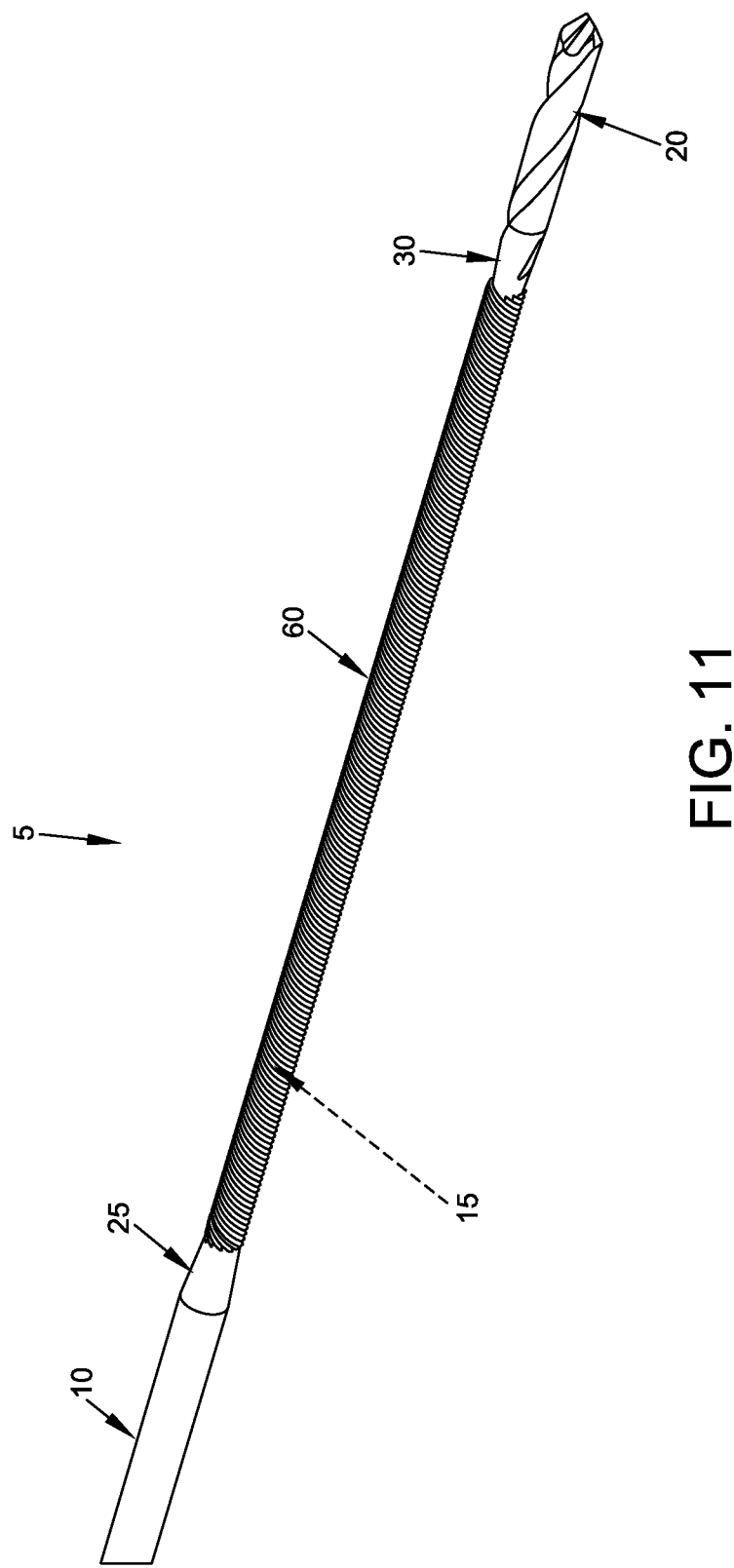
FIG. 11 is a schematic view showing the flexible drill bit of FIG. 1 with another form of helical coil disposed over a portion of the flexible drill bit.

FIG. 11 shows a construction similar to that of FIG. 10, except that helical coil 60 comprises a multi-strand coil (i.e., multiple strands are coiled together). In this embodiment, adjacent multiple strands follow the same coil pitch. However, even with coils touching each other, the pitch can be greater than a single strand arrangement (e.g., as shown in FIG. 10). This construction (i.e., larger pitch with coils touching) can be beneficial to reduce "play" in the coil; that is, as the flexible drill bit 5 starts drilling into bone, the helical coil 60 will more quickly respond in carrying a portion of the torque.

Figure 12:
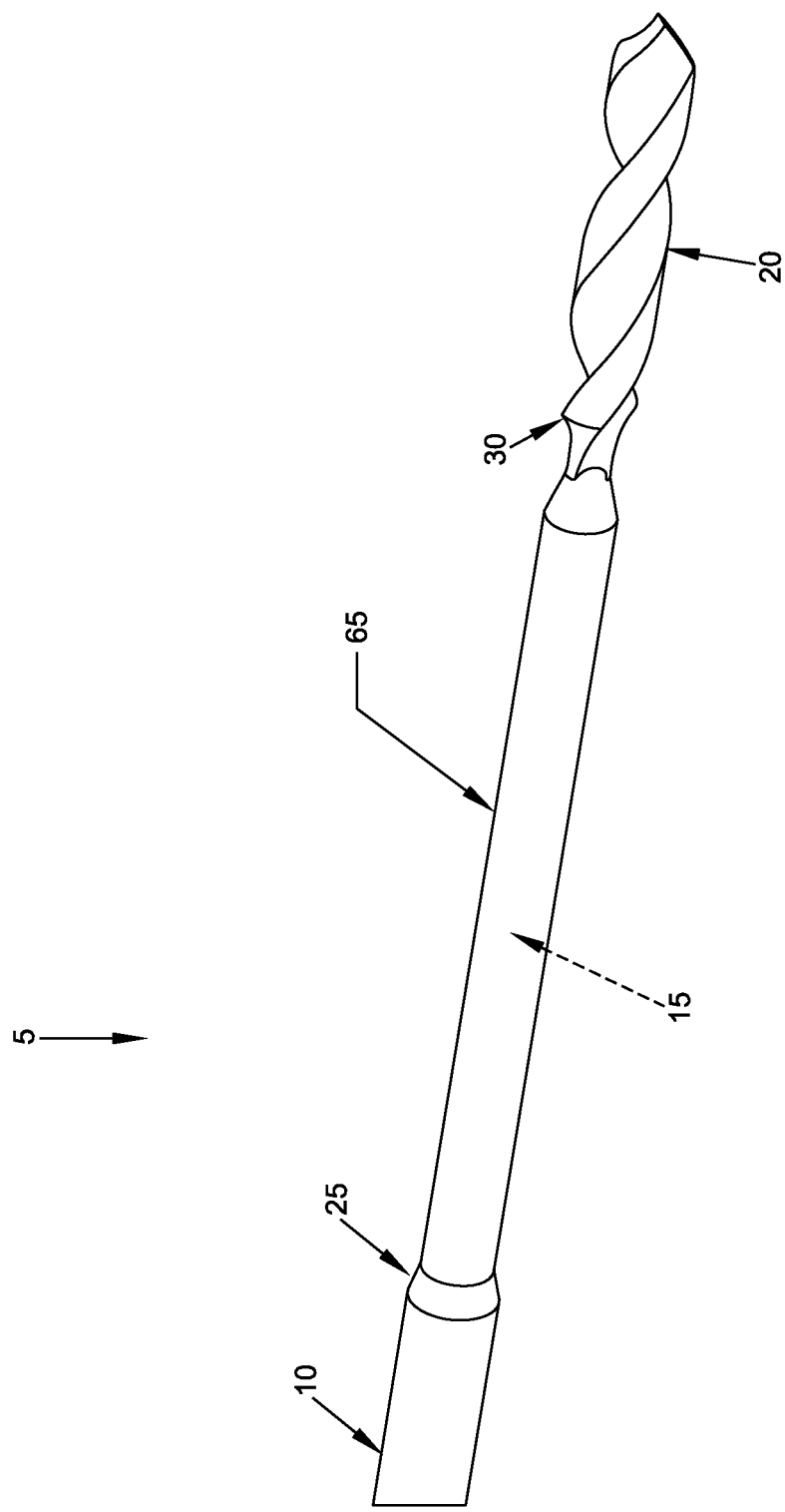
FIG. 12 is a schematic view showing the flexible drill bit of FIG. 1 with an over-molded sheath disposed over a portion of the flexible drill bit.

In another embodiment, and looking now at FIG. 12, an over-molded sheath 65 may be positioned over reduced diameter shaft portion 15 of flexible drill bit 5. Over-molded sheath 65 provides reduced friction (e.g., with curved drill guide 35 and/or bone 40) and increased diameter to reduced diameter shaft portion 15 of flexible drill bit 5, while still enabling bending of the reduced diameter shaft portion 15 of flexible drill bit 5. Over-molded sheath 65 may comprise a low-friction polymer such as Nylon or polytetrafluoroethylene (PTFE). Over-molded sheath 65 may be over-molded onto reduced diameter shaft portion 15 by injection molding or by diameter reduction (e.g., by shrinking or melting over-molded sheath 65 onto reduced diameter shaft portion 15).

Figure 13:
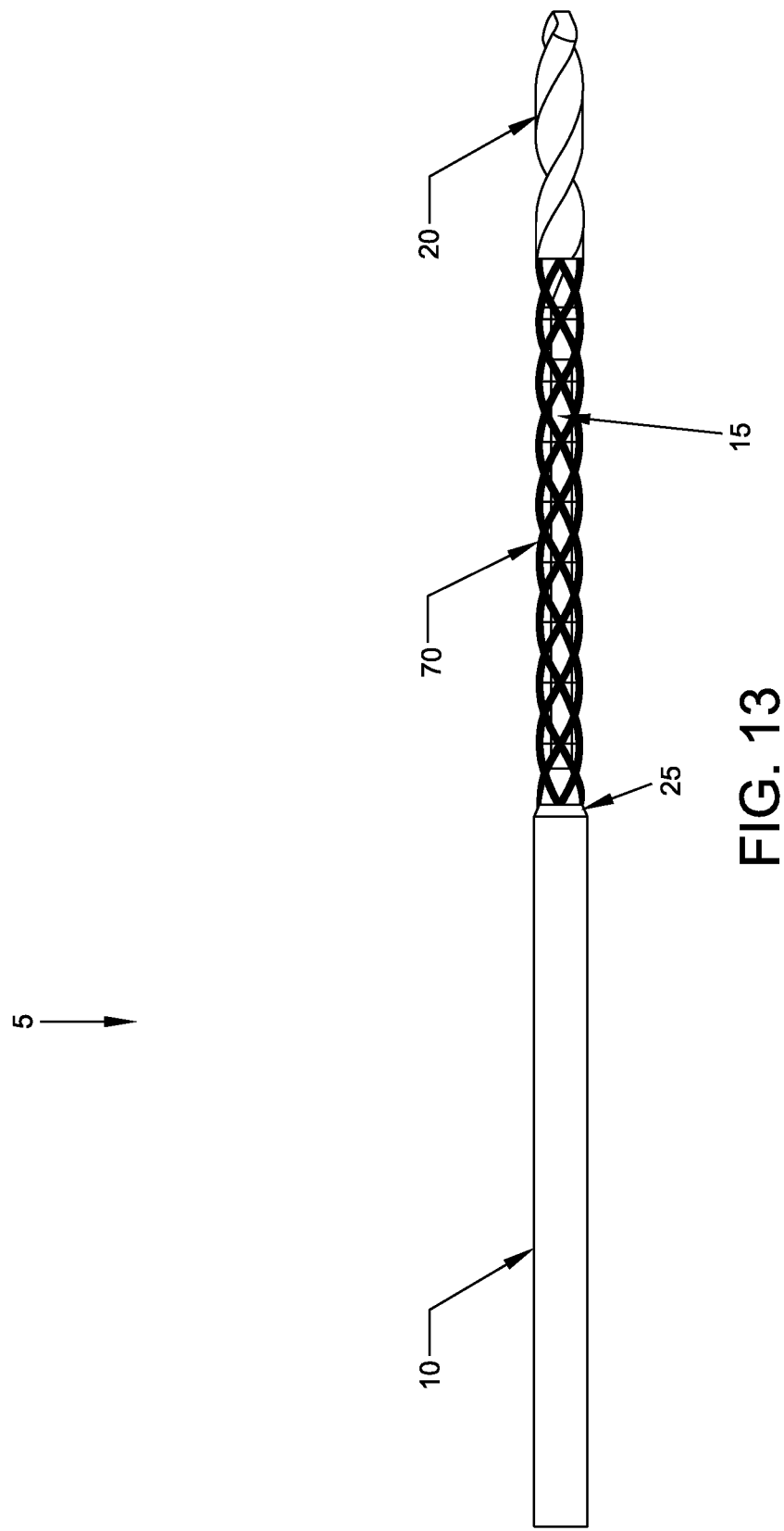
FIG. 13 is a schematic view showing the flexible drill bit of FIG. 1 with a metal braid or mesh disposed over a portion of the flexible drill bit.
Figure 29:
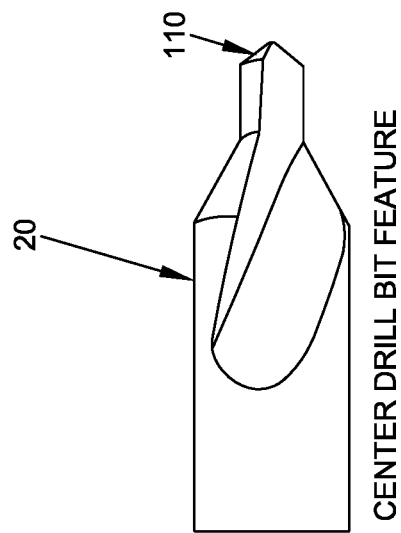
FIGS. 28-32 are schematic views showing various forms of cutting tips which may be used with the flexible drill bit of the present invention.
Figure 28:
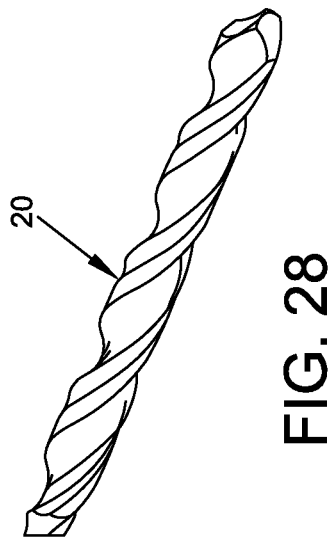
Figure 30:
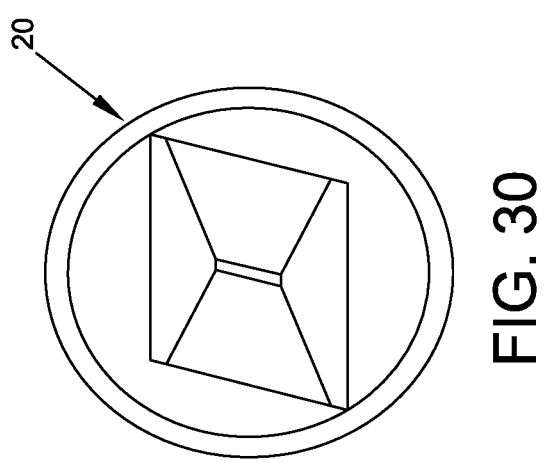
Figure 31:
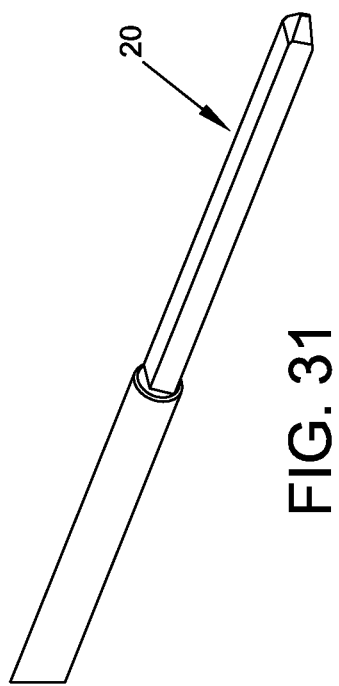

In another embodiment, and looking now at FIG. 13, a braid or mesh 70 (preferably but not necessarily formed out of metal) may be positioned over reduced diameter shaft portion 15 of flexible drill bit 5. Metal braid or mesh 70 provides torsional strength and increased diameter to reduced diameter shaft portion 15 of flexible drill bit 5, while still enabling bending/flexing of reduced diameter shaft portion 15 of flexible drill bit 5. Metal braid or mesh 70 may comprise a material such as stainless steel or Nitinol. It may comprise wire having a rectangular cross-section. Metal braid or mesh 70 may be attached to reduced diameter shaft portion 15 of flexible drill bit 5 by attaching one or both of its ends to the reduced diameter shaft portion, or by attaching an intermediate portion of metal braid or mesh 70 to reduced diameter shaft portion 15, or both (e.g., by welding, adhesive, etc.). Alternatively, or additionally, a polymer (e.g., Pebax) may be heated and melted into the metal braid or mesh 70 so as to create a solid structure atop reduced diameter shaft portion 15. This polymer can provide a lower friction surface than the metal braid or mesh 70 alone, and can provide some torque transmission as well.

Looking next at FIG. 14, there is shown a flexible drill bit 75 which is similar to the flexible drill bit 5 shown in FIG. 1, however, instead of providing a reduced diameter shaft portion (e.g., the aforementioned reduced diameter shaft portion 15) between the full diameter shaft portion (e.g., the aforementioned full diameter shaft portion 10) and the fluted cutting tip portion (e.g., the aforementioned fluted cutting tip portion 20) in order to create the desired flexibility in the drill bit, the full diameter shaft portion extends all the way to the fluted cutting tip portion and portions of material are removed from the full diameter shaft portion so as to create the desired flexibility in the drill bit while providing greater torque-carrying strength as compared to simply a reduced-diameter shaft portion 15.

More particularly, in this embodiment, and looking now at FIG. 14, flexible drill bit 75 comprises a full diameter shaft portion 10 and a fluted cutting tip portion 20, with full diameter shaft portion 10 and fluted cutting tip portion 20 being formed integral with one another (i.e., a "unibody" design). In order to render the distal end 78 of full diameter shaft portion 10 flexible, material is removed from the outer surface of the full diameter shaft portion, but penetrating only a portion of the way through the full diameter shaft portion so as to leave an intact inner core, whereby to create a flexible portion along the full diameter shaft portion of the drill bit. In other words, the material is removed from the exterior of the full diameter shaft portion, but for only a portion of the radius of the full diameter shaft portion, so as to leave an intact inner core along this portion of the flexible drill bit. The material is removed in a pattern which enhances shaft flexibility but minimizes the reduction of torque transmission. In one preferred form of the invention, the material is removed in a spiral pattern as shown at 80 in FIG. 14 and may be accomplished by laser cutting, electrical discharge machining (i.e., EDM), machining, grinding or other means. For a clockwise rotating flexible drill bit 5, spiral cuts 80 are preferably formed in a clockwise pattern (when viewed from proximal to distal direction), but may also be formed in a counter-clockwise pattern.

Material may also be removed from full diameter shaft portion 10 in other patterns so as to create a flexible, yet high torque transmitting, portion along the shaft of the drill bit. By way of example but not limitation, and looking now at FIG. 15, a series of transverse slots 85 (instead of the spiral cuts 80 shown in FIG. 14) may be cut into the shaft, with the slots preferably following a spiral or other geometric pattern.

Transverse slots 85 may be formed with various configurations. FIGS. 16-19 show one way of configuring transverse slots 85. FIGS. 20-23 show another way of configuring transverse slots 85. Still other ways of configuring transverse slots 85 will be apparent to those skilled in the art in view of the present disclosure.

In this embodiment of the invention, flexible drill bit 75 may comprise a material such as stainless steel or Nitinol.

Flexible Drill Bit Having a Multi-Body Construction

In another embodiment of the present invention, portions of the flexible drill bit (e.g., the cutting tip) may comprise separate components which are connected to the remaining portions of the flexible drill bit (e.g., the solid shaft) in order to provide a flexible drill bit having a multi-body construction.

More particularly, and looking now at FIGS. 24 and 25, there is a shown a flexible drill bit 90 comprising two components (i.e., full diameter shaft portion 10 and fluted cutting tip portion 20) which are connected together so as to form a flexible drill bit having three sections, i.e., a distal cutting tip, a proximal shaft and an intermediate flexible region. In this embodiment of the invention, fluted cutting tip portion 20 comprises an elongated solid shaft 95 which is received within a lumen 100 formed in full diameter shaft portion 10 and then secured therein (e.g., by welding, adhesive bond, swaging, etc. or a combination thereof or other means well known in the art). Full diameter shaft portion 10 is preferably secured to fluted cutting tip portion 20 at the distal end of full diameter shaft portion 10, e.g., at 102. Flexible drill bit 90 may comprise additional points of securement between full diameter shaft portion 10 and fluted cutting tip portion 20 (e.g., proximal of the intermediate flexible region, such as at 103). The drill bit is rendered flexible by removing material from full diameter shaft portion 10, e.g., such as by forming spiral cuts 80 in full diameter shaft portion 10. Although spiral cuts 80 are shown in FIGS. 24 and 25 as being formed in a clockwise pattern (when viewed from proximal to distal direction), they preferably would be formed in a counter-clockwise pattern when used with a clockwise-rotating drill (when viewed from proximal to distal) so that the spiral cuts would tend to tighten down on the elongated solid shaft 95 during drilling. Alternatively, and looking now at FIGS. 26 and 27, the material may be removed as an interrupted spiral cut 105 so as to provide the desired flexibility to the drill bit. In one preferred form of this embodiment, the cuts are interrupted segment lengths of less than 120 degrees around the perimeter, have a opening—or width—which is less than the pitch distance (i.e., longitudinal distance between adjacent cuts), and have a gap between laser cuts which is approximately equal to the pitch distance. In one preferred form of this embodiment, the cuts have a slight angle relative to perpendicular to the longitudinal axis of the flexible drill bit 90.

Depending on the location(s) of securement between full diameter shaft portion 10 and fluted cutting tip portion 20 (e.g., at securement point 102, securement point 103, etc.), the torque may be transmitted through the intermediate flexible region by: (i) the full diameter shaft portion 10 (distal securement only); or (ii) through solid shaft 95 of fluted cutting tip portion 20 (proximal securement only); or (iii) shared between the two (both the proximal and distal securements).

Cutting Tip Constructions

Figure 32:
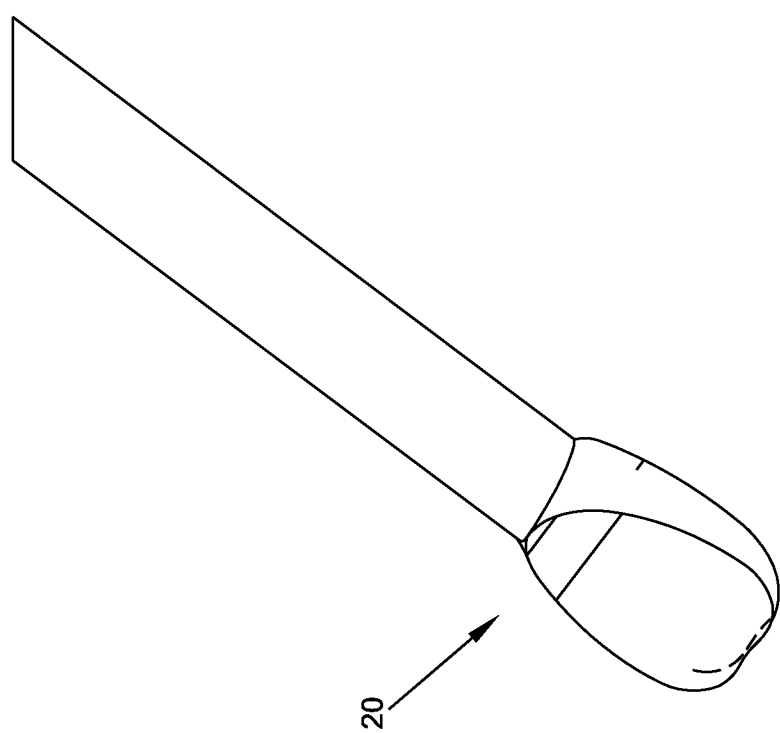

Looking now at FIGS. 28-32, there are shown various shapes and designs of cutting tips which may be used in accordance with the present invention, e.g., a fluted cutting tip (FIG. 28), a fluted cutting tip with a centering feature 110 similar to a center drill bit (FIG. 29), a diamond shape (FIGS. 30 and 31) or a forged or flattened tip (FIG. 32). Other cutting tip shapes and designs known in the art may also be used in accordance with the present invention (e.g., a bevel cut tip). In the cutting tip embodiment of a fluted cutting tip (e.g., FIG. 28), the inclusive angle at the tip may be approximately 30-120 degrees, is more preferably approximately 60-90 degrees, and is most preferably approximately 70 degrees.

Helical Structures

In the foregoing disclosure, various constructions are provided in which the flexible drill bit comprises a helical structure. By way of example but not limitation, a helical coil 60 is mounted over reduced diameter shaft portion 15 (FIGS. 10 and 11), a helical groove is formed in full diameter shaft portion 10 (FIGS. 14 and 24-27), etc. These constructions are provided in order to maximize the flexibility of the drill bit while minimizing reduction of torque transmission capability through the drill bit. In this respect it will be appreciated that the configuration of the helical structure (i.e., the direction of the spiral) is preferably related to the direction of the applied torque, in order to maintain maximum torque transmission strength through the drill bit. However, the relationship of these may vary depending on the specific construction of the drill bit.

In the embodiment of a helical coil mounted over a reduced diameter shaft portion (FIGS. 10 and 11), where the torque is intended to be applied in a clockwise direction (when viewed from the proximal end of the drill bit), it is preferred that the helix rotate counter-clockwise as it advances down the drill bit, and where the torque is intended to be applied in a counter-clockwise direction (when viewed from the proximal end of the drill bit), it is preferred that the helix rotate clockwise as it advances down the drill bit. Such an inverse relationship between the direction of the applied torque and the direction of the spiral will ensure that any deformation of the helical coil from the applied torque will cause the helical coil to tighten, whereby to preserve torque transmission through the helical coil.

In the embodiment of a helical groove formed in a full diameter shaft portion (FIGS. 14 and 24-27), where the torque is intended to be applied in a clockwise direction (when viewed from the proximal end of the drill bit), it is preferred that the helix rotate counter-clockwise as it advances down the drill bit, and where the torque is intended to be applied in a counter-clockwise direction (when viewed from the proximal end of the drill bit), it is preferred that the helix rotate clockwise as it advances down the drill bit. The appropriate relationship between the direction of the applied torque and the direction of the spiral will maximize torque transmission while maintaining drill bit flexibility.

General Construction

The flexible drill bit may comprise Nitinol or stainless steel or any other material which is flexible enough to bend into a curved state, and strong enough to transmit the torsional forces required for drilling into bone.

The entire shaft or portions of the shaft can be coated (e.g., with a biocompatible lubricant and/or a low-friction biocompatible outer sleeve such as a low-friction polymer, etc.) so as to reduce friction (e.g., with curved drill guide 35 and/or bone 40).

Angled Drill Guide for Use with Flexible Drill Bit

In the preceding description, a flexible drill bit is disclosed for use in drilling a hole in material (e.g., bone) where the angle of approach is offset from the angle at which the drill is to enter the material.

In accordance with the present invention, there is now also provided a novel angled drill guide (i.e., a curved drill guide) which may be used to guide entry of the flexible drill bit into the target material (e.g., bone) while the flexible drill bit is in its curved configuration.

Figure 33:
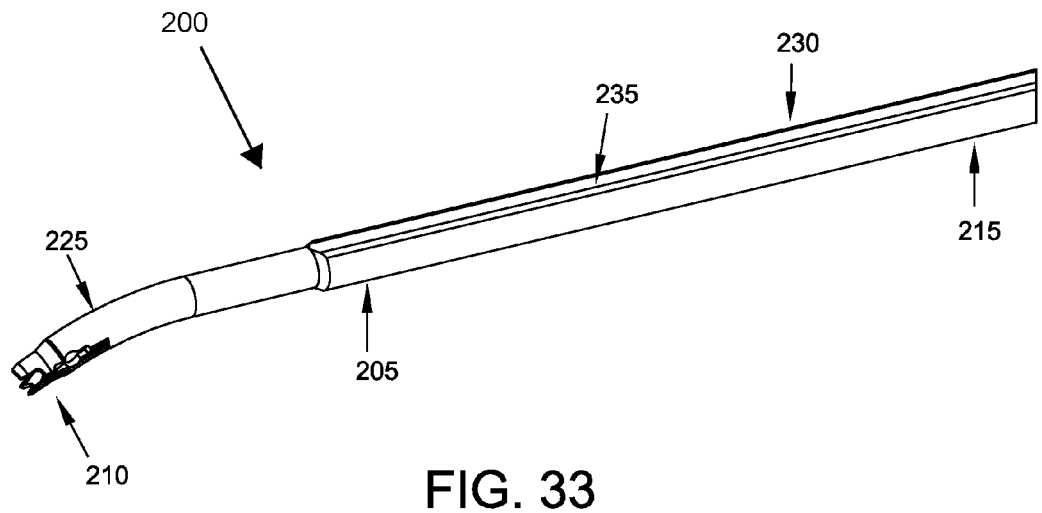
FIGS. 33-36 are schematic views showing a novel angled drill guide formed in accordance with the present invention.
Figure 34:
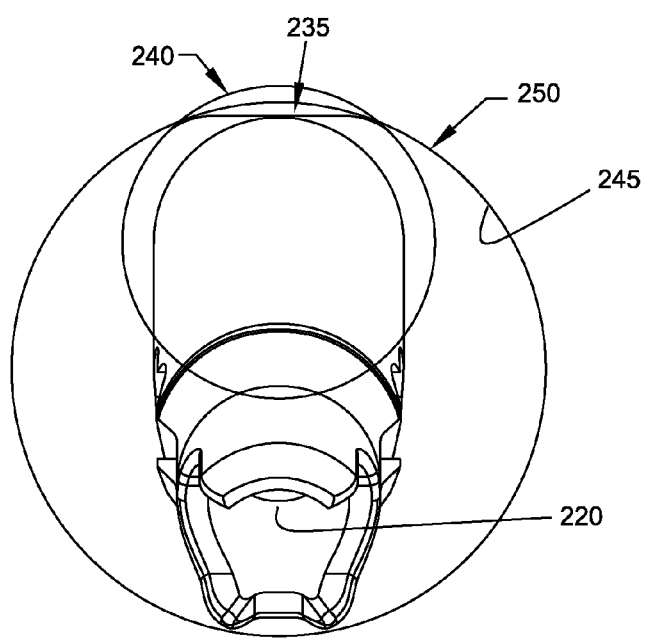

More particularly, and looking now at FIGS. 33 and 34, in one preferred form of the invention, there is provided a novel angled drill guide 200 for use in guiding a flexible drill bit (e.g., such as a flexible drill bit discussed above) into target material (e.g., bone). Novel angled drill guide 200 generally comprises an elongated shaft 205 having a distal end 210, a proximal end 215 and a lumen 220 extending therebetween. Preferably elongated shaft 205 has a curved distal portion 225 and a straight proximal portion 230.

In order to allow angled drill guide 200 to be formed with a greater degree of curvature and still pass through the interior lumen of a straight access cannula, at least a portion of straight proximal portion 230 (and, optionally, a portion of curved distal portion 225) is formed with a flat 235 extending therealong, with flat 235 being formed on the same side as the outside of the curve. Flat 235 reduces the effective diameter of elongated shaft 205 so as to minimize interference between the angled drill guide and the side wall of the straight access cannula, thereby allowing angled drill guide 200 to be formed with a greater degree of curvature while still fitting through the straight access cannula with a preferred diameter (e.g., 8 mm inner diameter). See, for example, FIG. 34, which shows how flat 235 on elongated shaft 205 eliminates the area of interference 240 created between angled drill guide 200 and the side wall 245 of a straight access cannula 250.

It will be appreciated that the provision of the flat 235 on elongated shaft 205 can also be used with a curved access cannula so as to eliminate an area of interference between an angled drill guide and the curved access cannula, e.g., where the angled drill guide has an angle of curvature which is greater than the angle of curvature of the curved access cannula.

Figure 35:
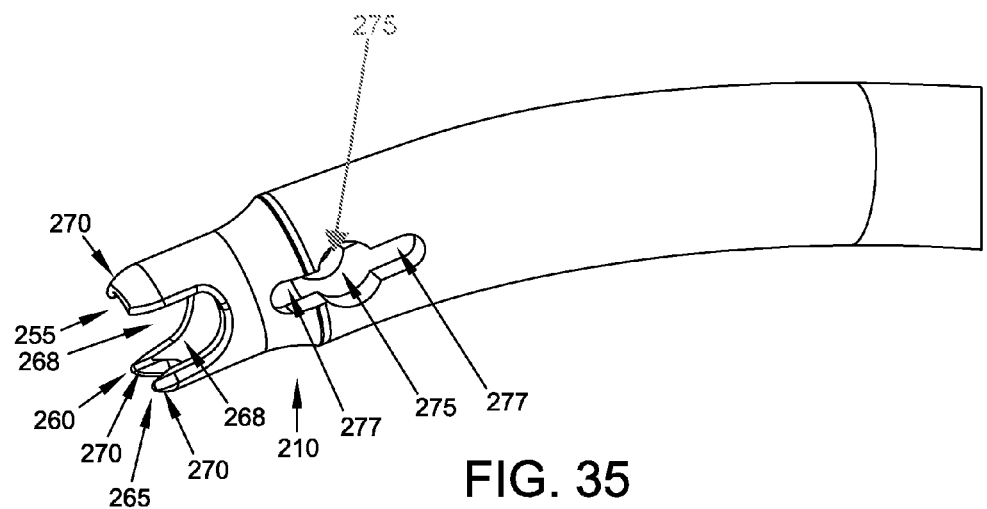
Figure 36:
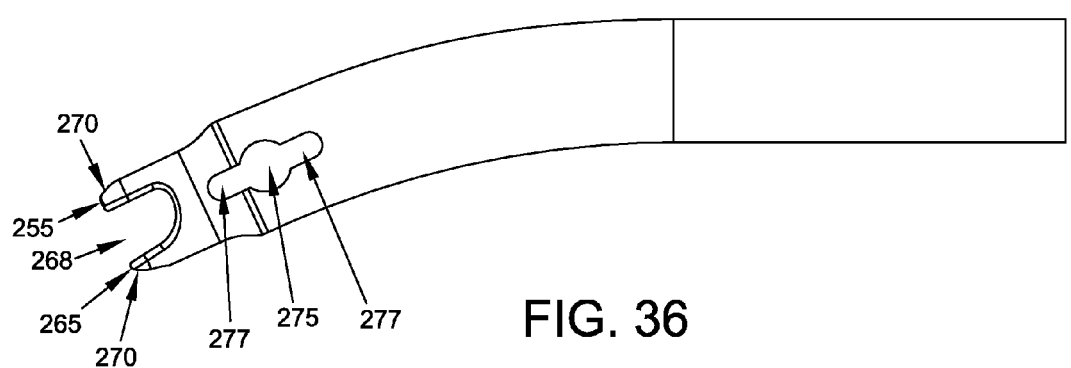

Looking now at FIGS. 35 and 36, it will be seen that the distal end 210 of elongated shaft 205 may be formed with three teeth 255, 260, 265 for engaging the surface of the material (e.g., bone) which is to be drilled. Tooth 255 serves to provide a stable support against the material (e.g., bone) which is to be drilled. To this end, tooth 255 is relatively large and is set at the outer perimeter of the curve of angled drill guide 200, thus providing a smooth, continuous surface for a flexible drill bit to ride against as the flexible drill bit passes out the distal end of angled drill guide 200. Specifically, the flexible drill bit may have a tendency to follow the outer perimeter of the curve of angled drill guide 200 when the flexible drill bit is in a flexed state. The cutting edges of the flexible drill bit may catch and/or bear against any irregularities in the surface of angled drill guide 200; therefore, it is preferable to maintain a smooth, uninterrupted surface for the flexible drill bit to bear against. In one preferred form of the invention, tooth 255 extends along approximately 90-180 degrees of the perimeter of the angled drill guide, and preferably along approximately 115 degrees of the perimeter of the angled drill guide. Teeth 260, 265 serve to grip into the material (e.g., bone) which is to be drilled. This is especially significant with an angled drill guide 200, as there are forces imparted on the angled drill guide 200 while drilling into bone (and/or when thereafter implanting an anchor into bone using the angled drill guide) which can tend to make the distal end of the angled drill guide 200 skid along the material (e.g., bone). To this end, teeth 260, 265 are relatively thin and are set at the inner perimeter of the curve of angled drill guide 200. Slots 268 allow the user to view a flexible drill bit exiting the angled drill guide 200. Preferably teeth 255, 260, 265 are radiused at their distal ends (e.g., as shown at 270) so as to facilitate passage of angled drill guide 200 through an access cannula (which may be either straight or curved).

In one preferred form of the invention, angled drill guide 200 also comprises side windows 275 disposed proximal to teeth 255, 260, 265. Preferably side windows 275 have side cuts 277 extending proximally and distally from side windows 275, with side cuts 277 being aligned with the longitudinal axis of angled drill guide 200. Windows 275 allow the user to view a flexible drill bit extending though angled drill guide 200; by providing appropriate markings (not shown) along the shaft of the flexible drill bit, the user can (by aligning those drill bit markings with windows 275) tell the depth to which the flexible drill bit is drilling into the material (e.g., bone), and/or tell the depth to which a bone anchor (being inserted through angled drill guide 200) is inserted into the material (e.g., bone).

Figure 37:
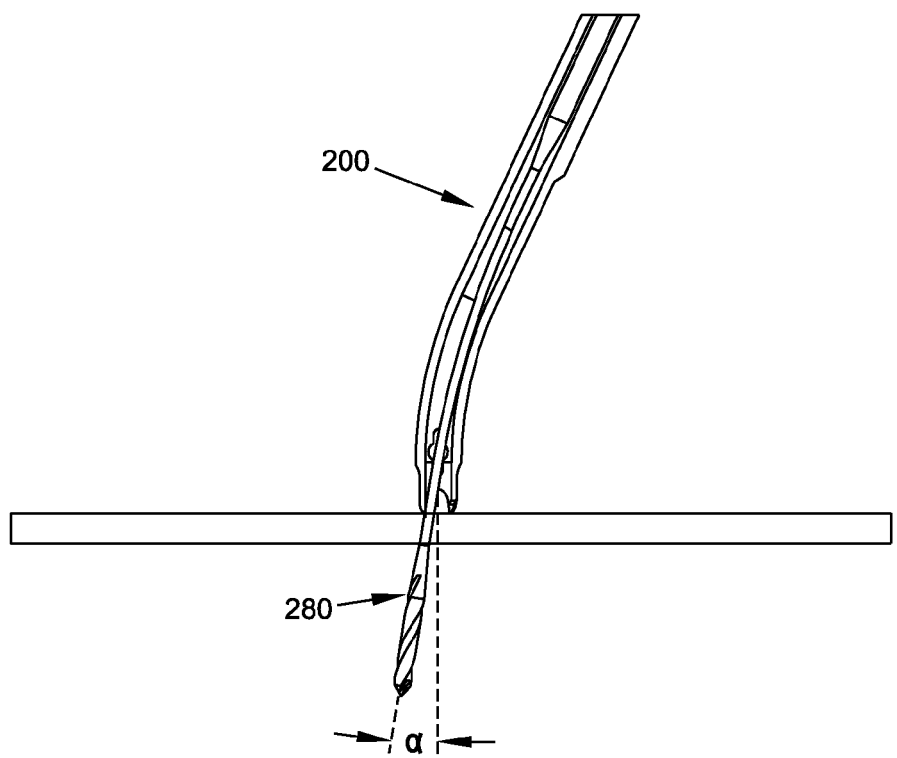
FIG. 37 is a schematic view showing how a flexible drill bit exiting the distal end of an angled drill guide will tend to exit the angled drill guide with an off-centered disposition.

Significantly, where a flexible drill bit passes through an angled drill guide having a curve, the flexible drill bit will tend to bear against the outside of the curve. As a result, when the flexible drill bit exits the distal end of an angled drill guide, the flexible drill bit will tend to exit the distal end of the angled drill guide 200 with an off-angle disposition. See FIG. 37, where a flexible drill bit 280 is shown exiting angled drill guide 200 with offset angle α.

Figure 38:
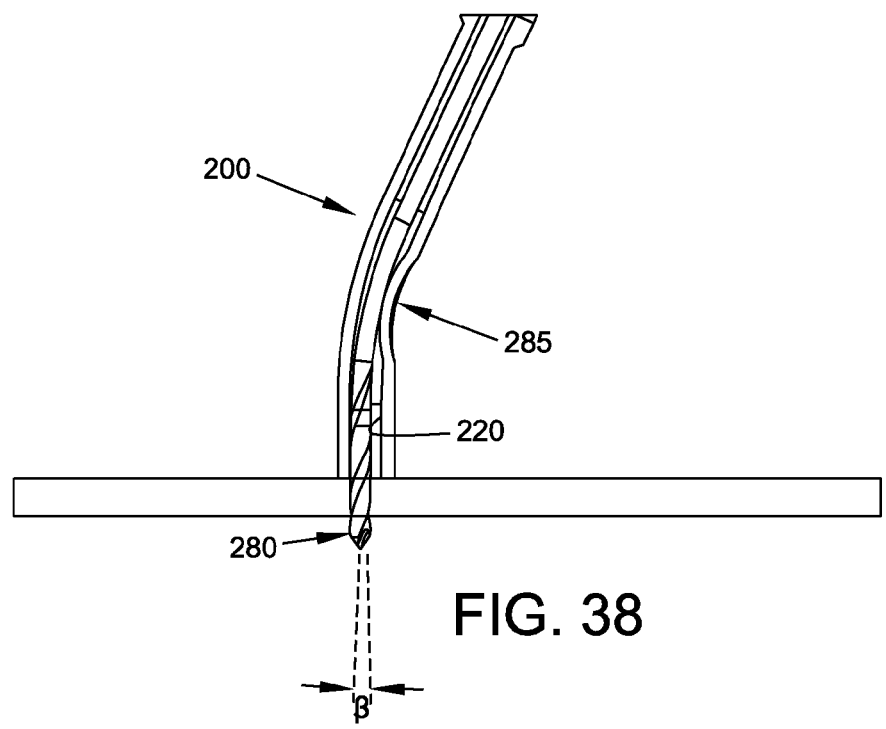
FIG. 38 is a schematic view showing how an angled drill guide may be provided with a dimple so as to re-center the flexible drill bit as it exits the distal end of the angled drill guide.

To counteract this effect, and looking now at FIG. 38, angled drill guide 200 may be provided with a dimple 285 in the side wall of the angled drill guide. Dimple 285 is diametrically-opposed to the outside of the curve of angled drill guide 200, and effectively narrows lumen 220. As a result of this construction, when a flexible drill bit is disposed in lumen 220 of the angled drill guide, dimple 285 forces the flexible drill bit into a smaller bend radius that more closely matches the bend radius of the angled drill guide, whereby to re-align the flexible drill bit as it exits the distal end of the angled drill guide 200 and create offset angle θ (offset angle θ is less than the aforementioned offset angle α). This can be particularly beneficial if the flexible drill bit has a reduced diameter along the length which passes through the curved portion of the angled drill guide 200 (e.g., proximal to the cutting portion as discussed above).

Figure 39:
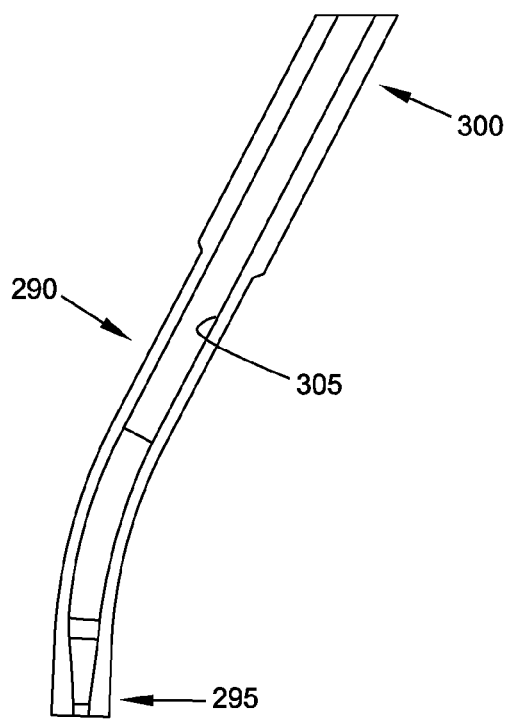
FIGS. 39 and 40 are schematic views showing how an angled drill guide may be provided with a tapered inner lumen so as to re-center the flexible drill bit as it exits the distal end of the angled drill guide.

FIG. 39 shows another approach for centering and aligning the flexible drill bit as it exits the distal end of the angled drill guide 290. More particularly, FIG. 39 shows an angled drill guide 290 having a distal end 295, a proximal end 300 and a lumen 305 extending therebetween. In this form of the invention, lumen 305 tapers inwardly (i.e., narrows) at the distal end of angled drill guide 290, whereby to constrain the orientation of a flexible drill bit to a re-centered and re-aligned disposition as it exits the distal end of the angled drill guide. In one preferred form of the invention, lumen 305 narrows so as to provide a bearing structure having a relatively close sliding fit with a flexible drill bit disposed in the angled drill guide, whereby to provide good support for the flexible drill bit as it emerges from the distal end of the angled drill guide. Thus, the flexible drill bit will be more centered with the center axis of the angled drill guide, and will be more angularly aligned with the curvature at the distal end of the angled drill guide.

Figure 40:
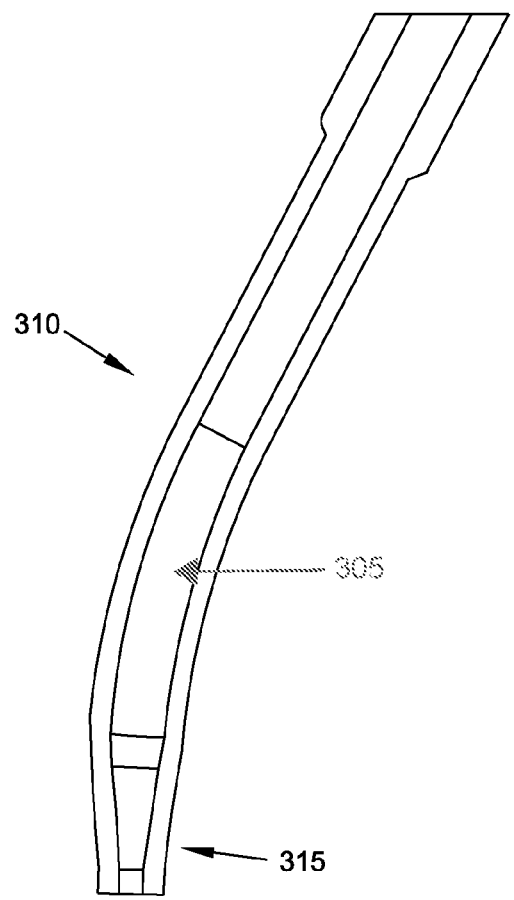

FIG. 40 shows another angled drill guide 310. Angled drill guide 310 is substantially identical to the angled drill guide 290 shown in FIG. 39, except that with the angled drill guide 310 shown in FIG. 40, distal end 315 of angled drill guide 310 has a tapered outer diameter (as well as a tapered inner diameter) so as to facilitate disposition of the angled drill guide about a drilling site.

Figure 41:
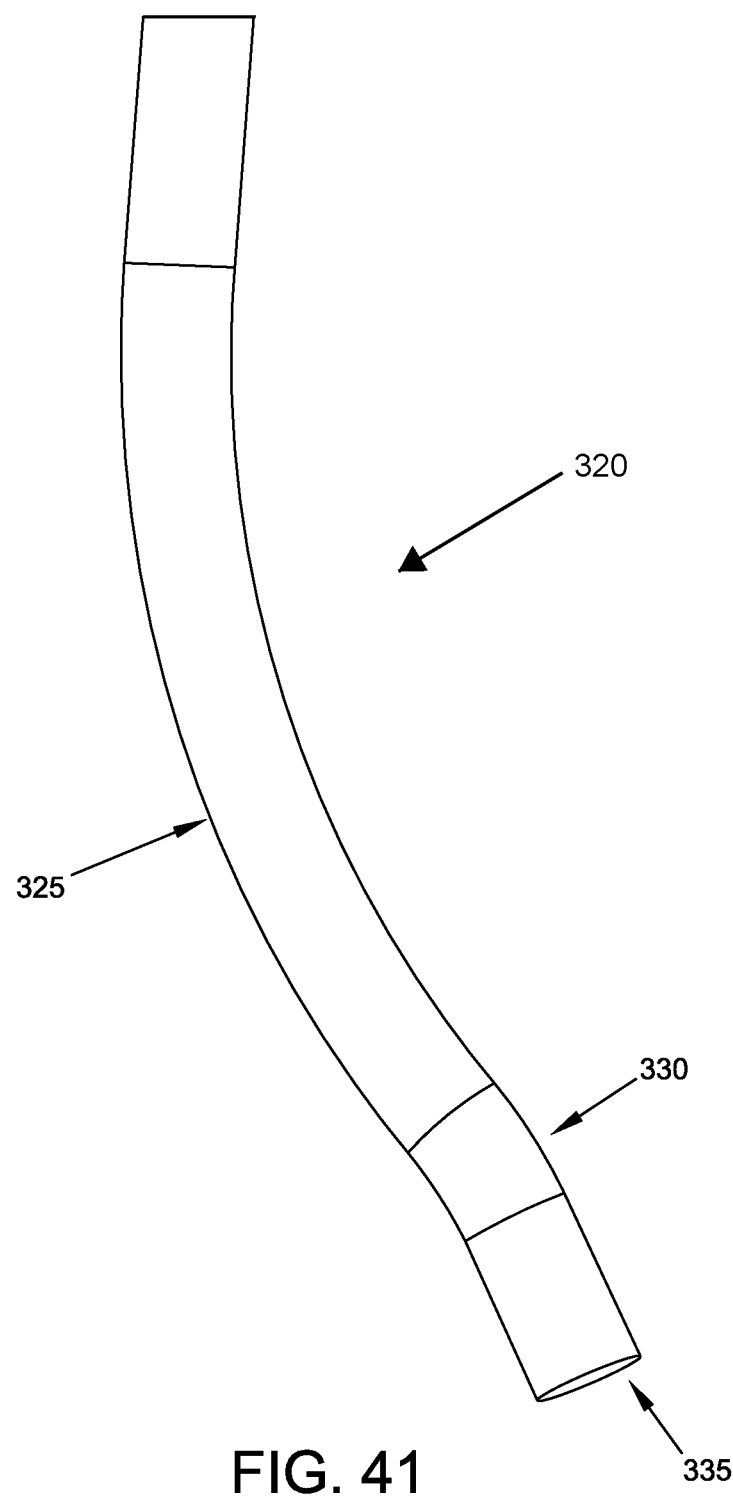
FIG. 41 is a schematic view showing how an angled drill guide may be provided with compound curves so as to re-center the flexible drill bit as it exits the distal end of the angled drill guide.

In another form of the present invention, and looking now at FIG. 41, there is shown an angled drill guide 320 which uses the combination of two curves 325, 330 to help center and align the flexible drill bit as it emerges from the distal end 335 of the angled drill guide. More particularly, as noted above, where a flexible drill bit passes through an angled drill guide having a curve, the flexible drill bit will tend to follow the outside of the curve. As a result, when the flexible drill bit exits the distal end of an angled drill guide, the flexible drill bit will tend to exit the distal end of the angled drill guide with an off-centered and mis-aligned disposition. To counteract this effect, the angled drill guide 320 shown in FIG. 41 is formed with two curves 325, 330—the curve 325 is the primary curve of the angled drill guide, providing the curvature needed for the flexible drill bit to access the drilling site, and the curve 330 is the secondary curve of the angled drill guide, providing the "remedial" curvature used to re-center and re-align the flexible drill bit as it exits the distal end 335 of angled drill guide 320.

Figure 42:
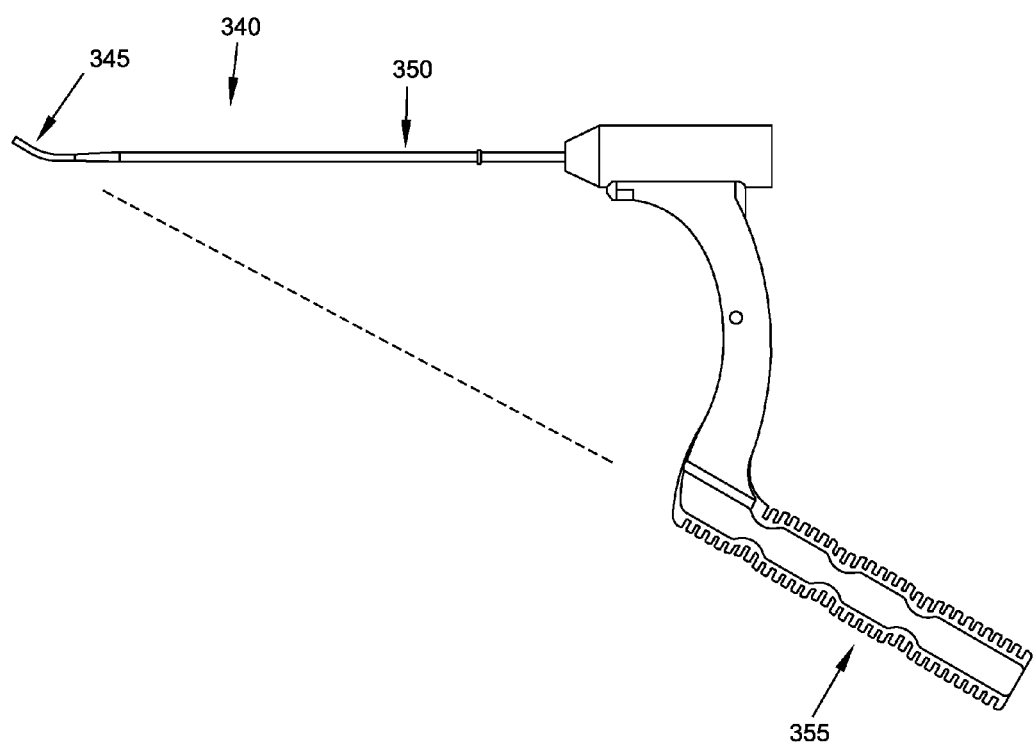
FIG. 42 is a schematic view showing how an angled drill guide may be provided with a novel handle so as to facilitate pushing the distal end of the angled drill guide directly against the outer surface of the material (e.g., bone) which is to be drilled, whereby to provide more stable drilling.

In another form of the present invention, and looking now at FIG. 42, an angled drill guide 340 having a curved distal section 345 and a straight proximal section 350 may be provided with a handle 355 which is offset from the longitudinal axis of the proximal section 350 of the angled drill guide, but which is aligned with the distal section 345 of the angled drill guide, so as to allow the user to better hold the angled drill guide against the material (e.g., bone) which is to be drilled. In essence, by aligning the longitudinal axis of handle 355 with the longitudinal axis of the distal section 345 of the angled drill guide, the user can push the distal end of the angled drill guide directly against the surface of the material (e.g., bone) which is to be drilled, thereby providing more stability during drilling. In other words, the tip of the angled drill guide will be better engaged with the bone and hence less likely to skid along the bone while the hole is being drilled with the angled drill guide and/or an anchor is being placed into the bone hole through the angled drill guide. This is significant, since the forces created during drilling and/or anchor placement through an angled drill guide have a tendency to move the distal end of the angled drill guide relative to the material (e.g., bone) which is being drilled.

The angled drill guide can have a curve of fixed geometry or it is also possible to make an articulating angled drill guide.

Figures 43, 44:
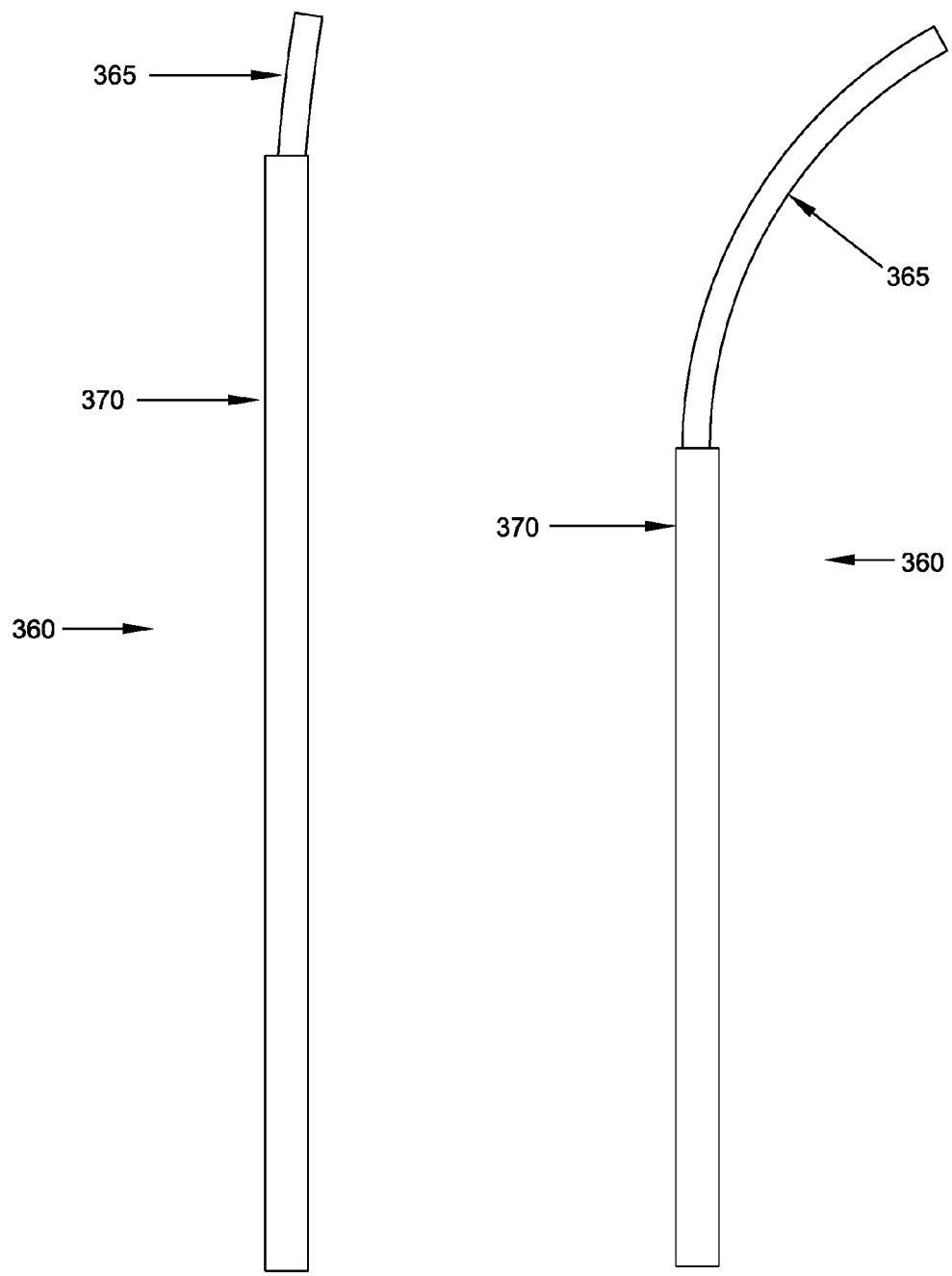
FIGS. 43 and 44 are schematic views showing a novel articulating angled drill guide formed in accordance with the present invention.

In an example of an articulating angled drill guide, and looking now at FIGS. 43 and 44, an angled drill guide 360 may comprise a curved inner sheath 365 for receiving a flexible drill bit (not shown), and a straight outer sheath 370 for overlying some or all of curved inner sheath 365. In this form of the invention, curved inner sheath 365 is in telescoping relation to straight outer sheath 370: retracting curved inner sheath 365 into straight outer sheath 370 causes the curved inner sheath 365 to straighten, while extending curved inner sheath 365 out of straight outer sheath 370 allows the curved inner sheath 365 to curve. Thus, by controlling the disposition of curved inner sheath 365 vis-à-vis straight outer sheath 370, the degree of curvature of the curved inner sheath 365 (and hence the degree of curvature of the angled drill guide as a whole) can be controlled. Curved inner sheath 365 and straight outer sheath 370 are preferably constructed of biocompatible metals; more preferably, curved inner sheath 365 is constructed of superelastic Nitinol and straight outer sheath 370 is constructed of stainless steel.

Figure 45:
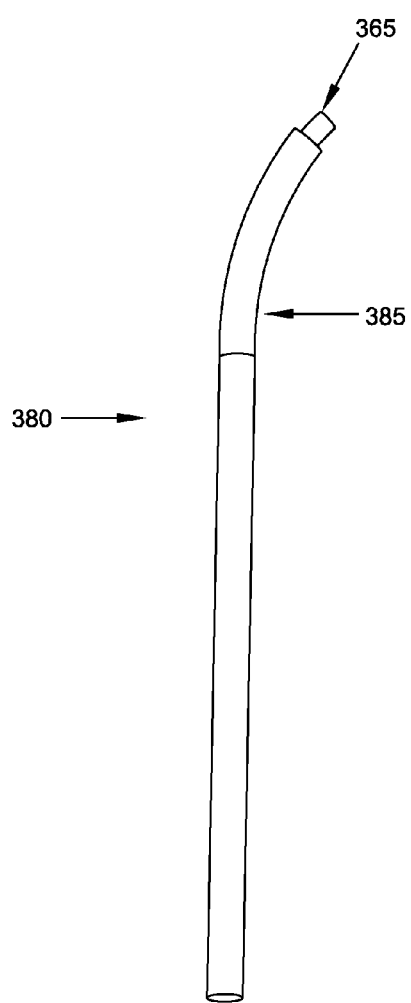
FIGS. 45 and 46 are schematic views showing another novel articulating angled drill guide formed in accordance with the present invention.
Figure 46:
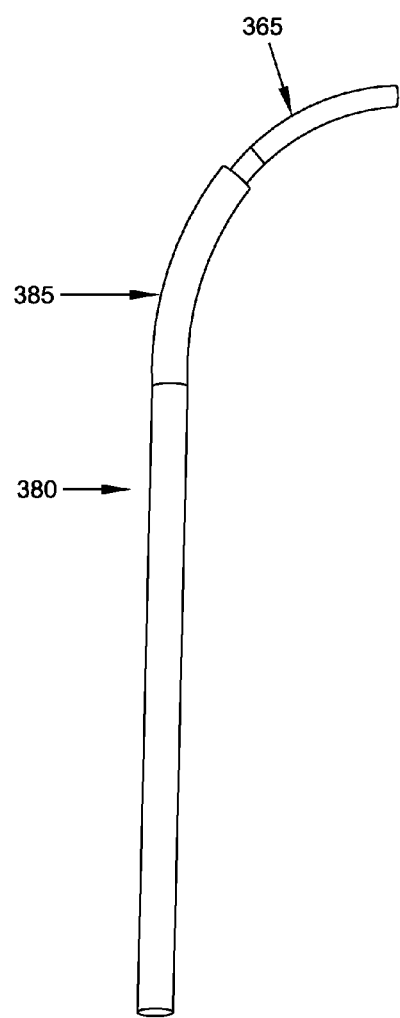

FIGS. 45 and 46 show another articulating drill guide 380. More particularly, articulating drill guide 380 is identical to the articulating drill guide 360 shown in FIGS. 43 and 44, except that curved inner sheath 365 is slidably disposed in a curved outer sheath 385, wherein curved outer sheath 385 has a lesser degree of curvature than curved inner sheath 365. Again, by controlling the disposition of curved inner sheath 365 vis-à-vis curved outer sheath 370, the degree of curvature of the curved inner sheath 365 (and hence the degree of curvature of the angled drill guide as a whole) can be controlled. Curved inner sheath 365 and curved outer sheath 385 are preferably constructed of biocompatible metal; more preferably, curved inner sheath 365 is constructed of superelastic Nitinol and curved outer sheath 385 is constructed of stainless steel.

Another articulating angled drill guide 390 is shown in FIGS. 47-49. Articulating angled drill guide 390 comprises a curved inner sheath 395 for receiving a flexible drill bit (not shown), and a curved outer sheath 400 for overlying most of curved inner sheath 395. In this form of the invention, rotating curved inner sheath 395 and curved outer sheath 400 relative to one another causes the curves to either (i) counteract one another, whereby to straighten the assembly (see FIG. 48), or (ii) to reinforce one another, whereby to curve the assembly (FIG. 49), or (iii) provide some disposition therebetween (FIG. 49A). Curved inner sheath 395 and curved outer sheath 400 are constructed out of biocompatible metal, and preferably of superelastic Nitinol. In order for the curved inner sheath 395 and curved outer sheath 400 to counteract one another (whereby to straighten the assembly), their bending stiffnesses should be similar. However, since the curved outer sheath 400 has a larger diameter, a difference in wall thickness and/or material properties is required in order to achieve a similar bending stiffness. In one example, where both curved inner sheath 395 and curved outer sheath 400 are the same material (e.g., superelastic Nitinol), the curved outer sheath 400 needs to have a thinner wall to achieve a similar bending stiffness to the curved inner sheath 395.

Figure 50:
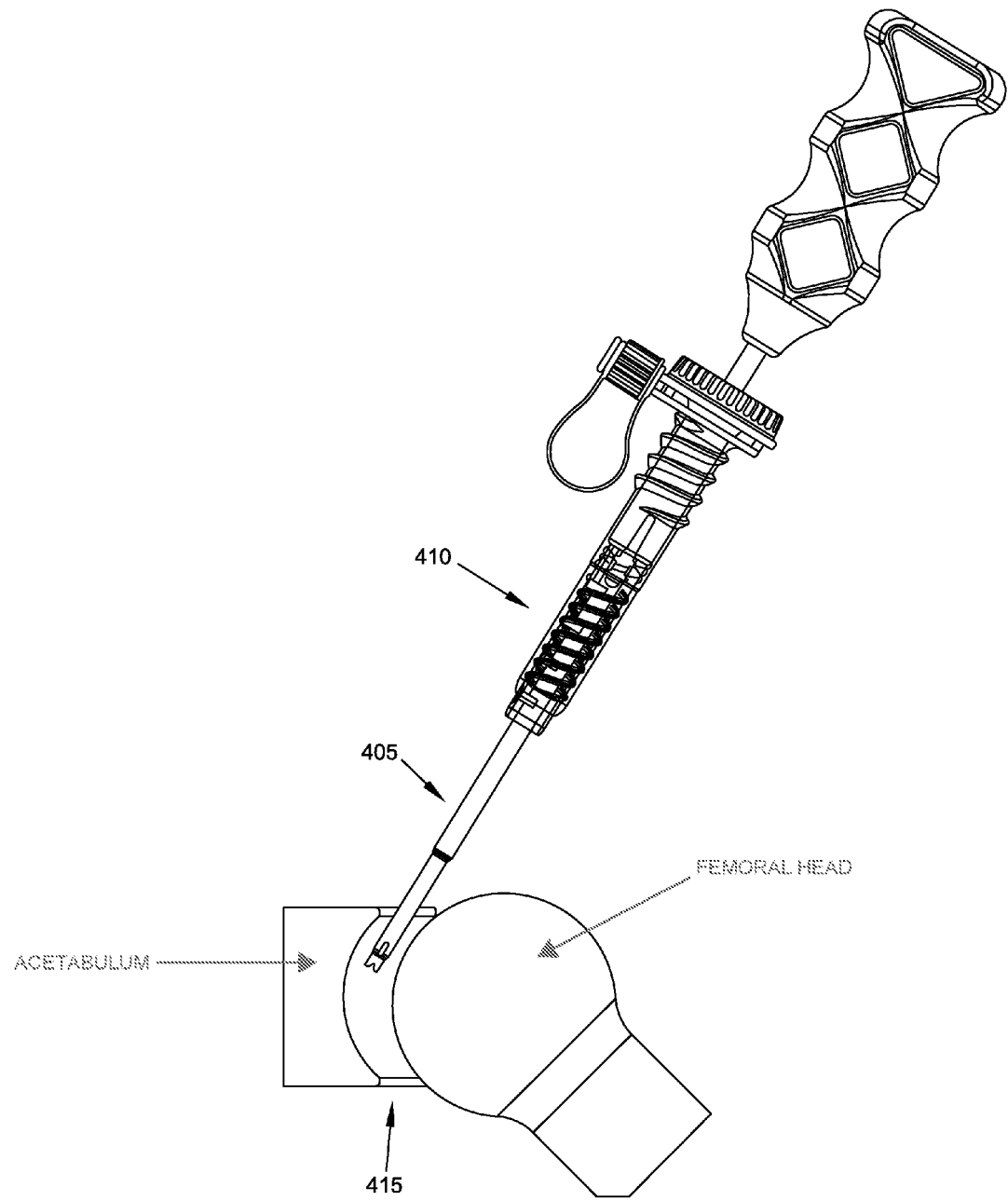
FIGS. 50-57 are schematic views showing how an articulating angled drill guide and flexible drill bit may be used to drill a hole in a surface of a joint.
Figure 51:
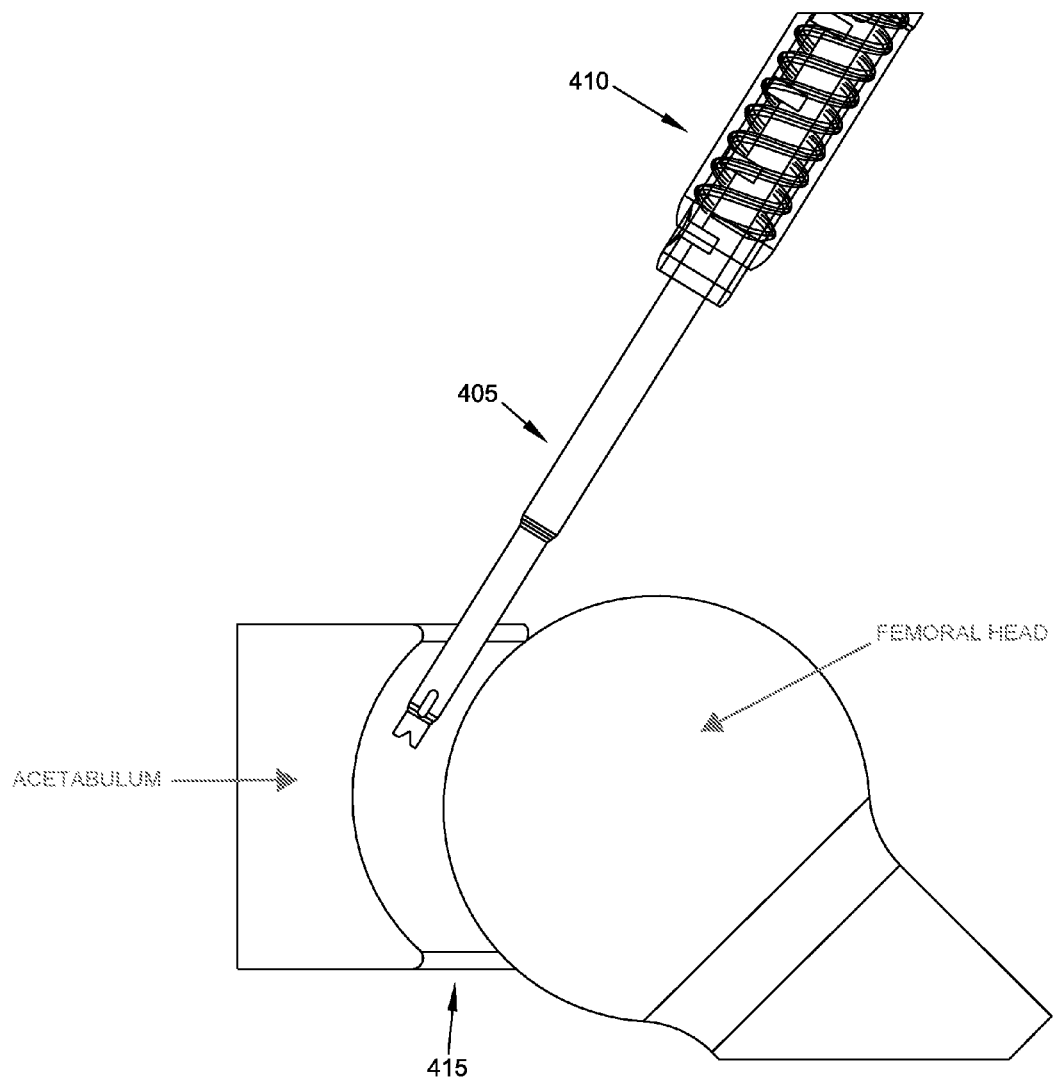
Figure 52:
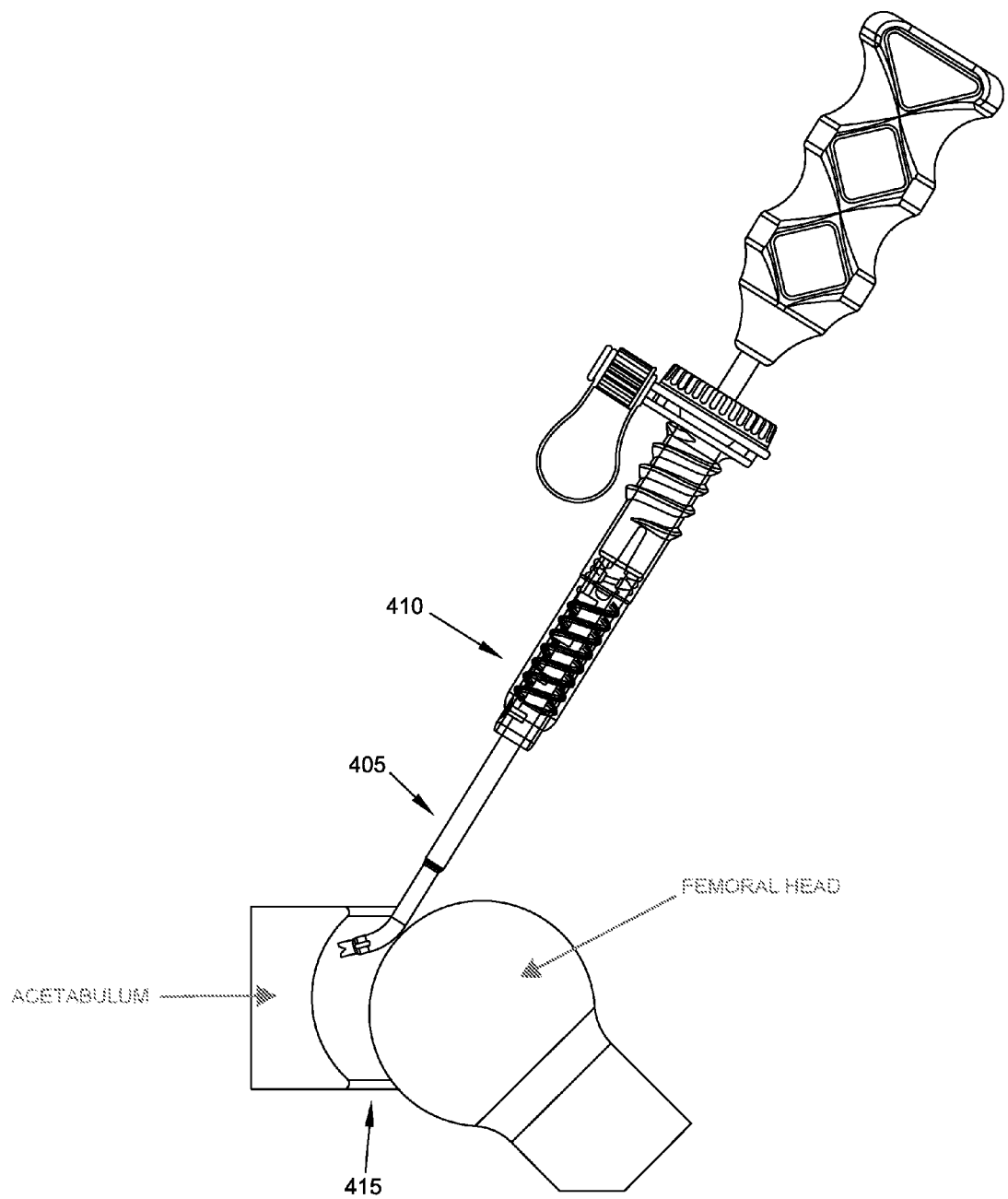
Figure 53:
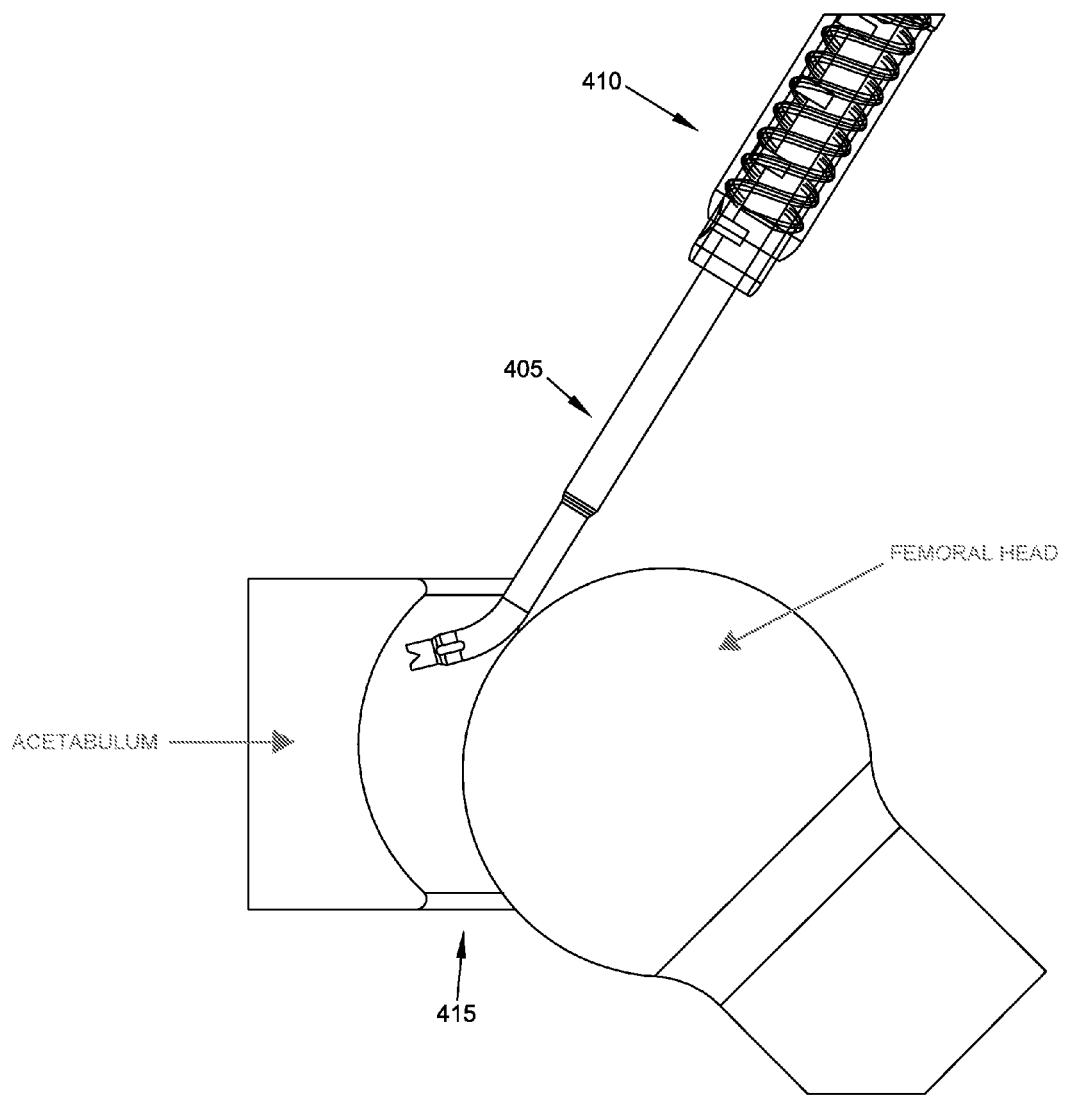
Figure 54:
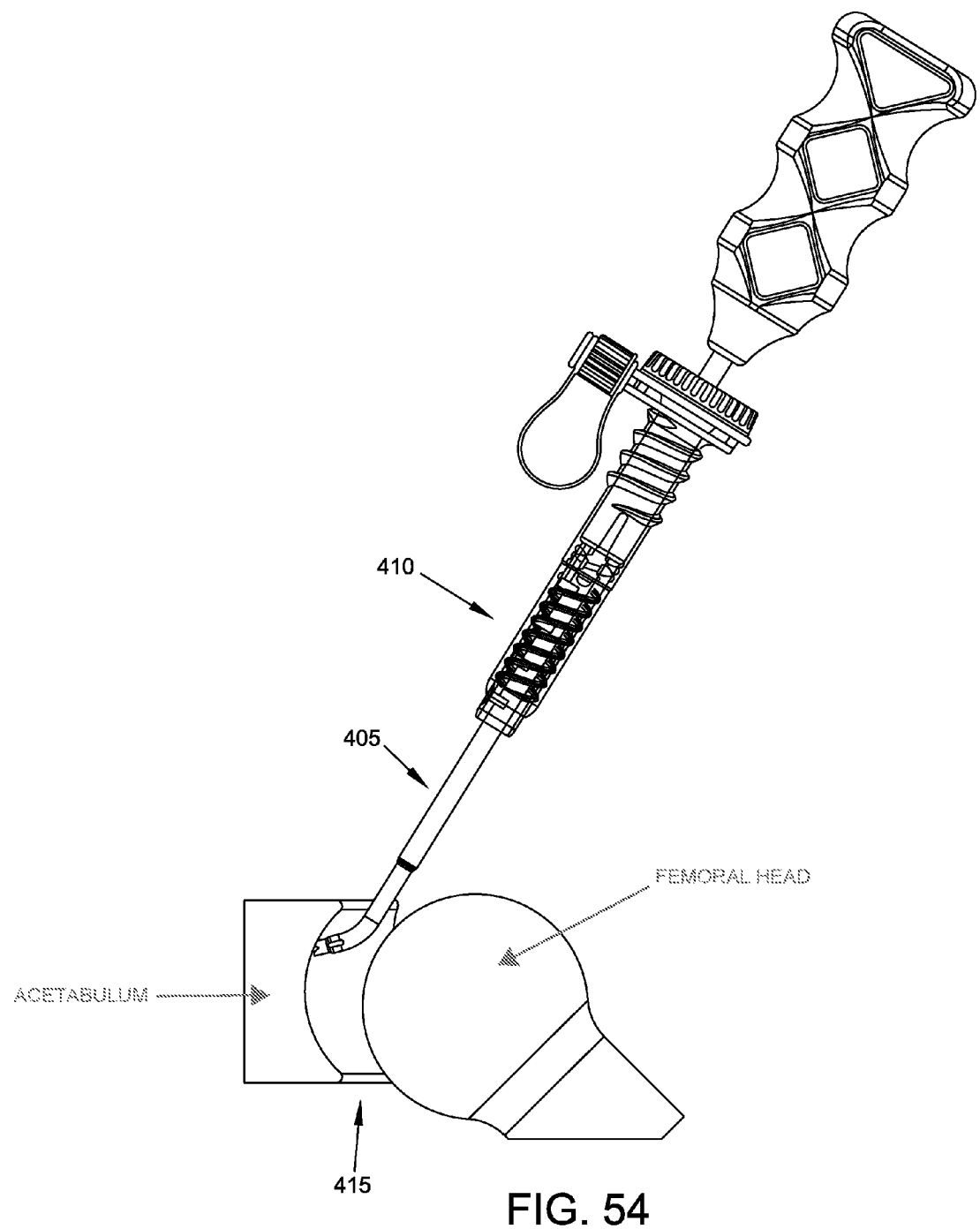
Figure 55:
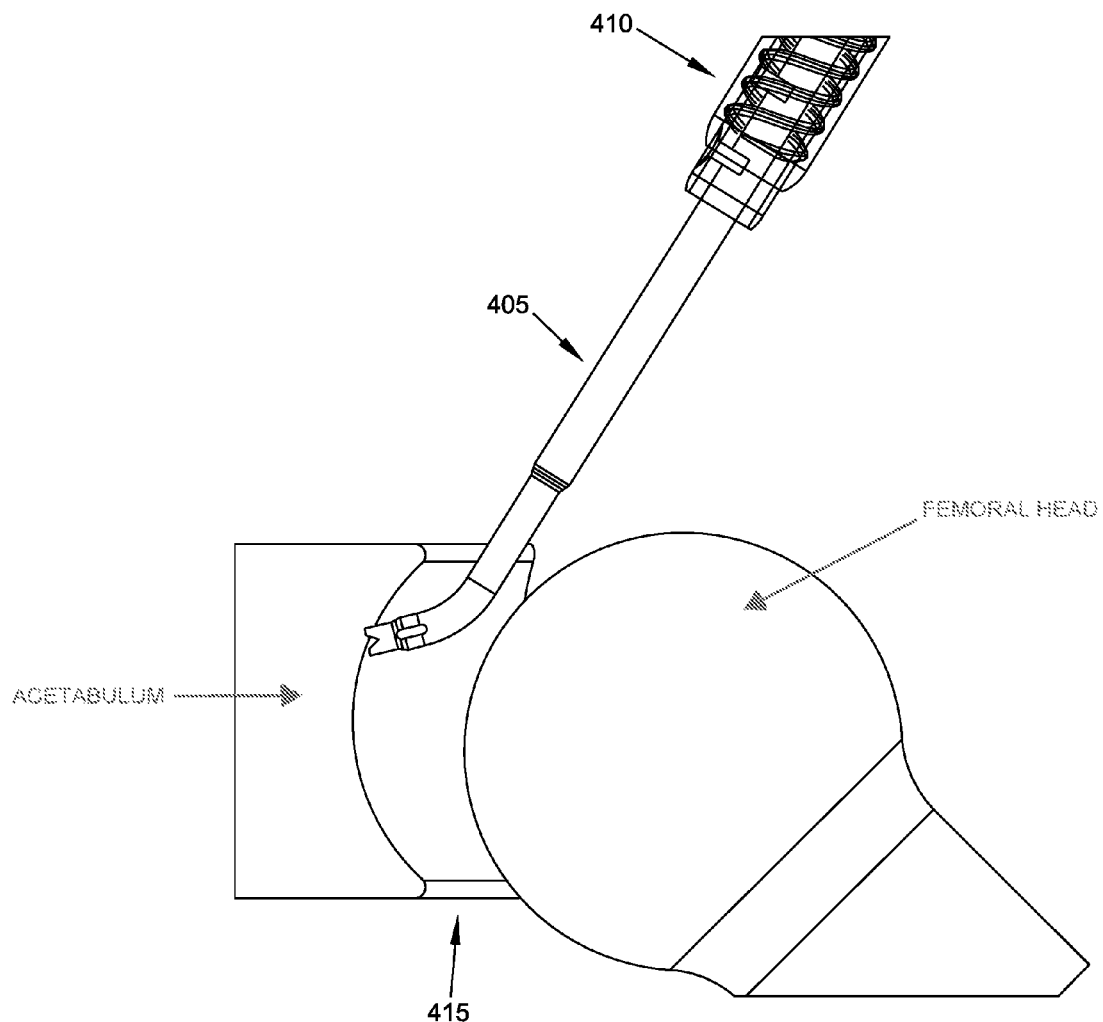
Figure 56:
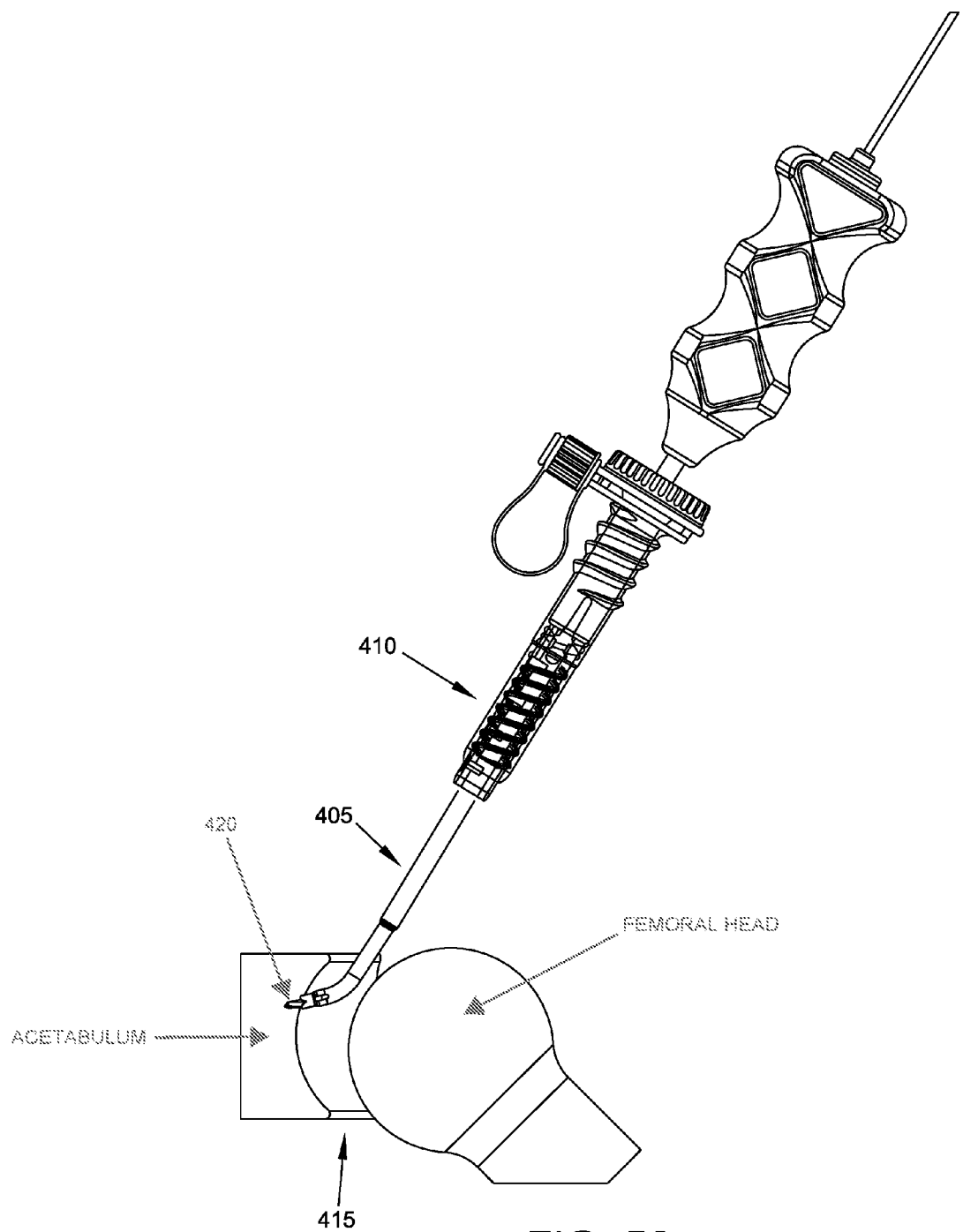
Figure 57:
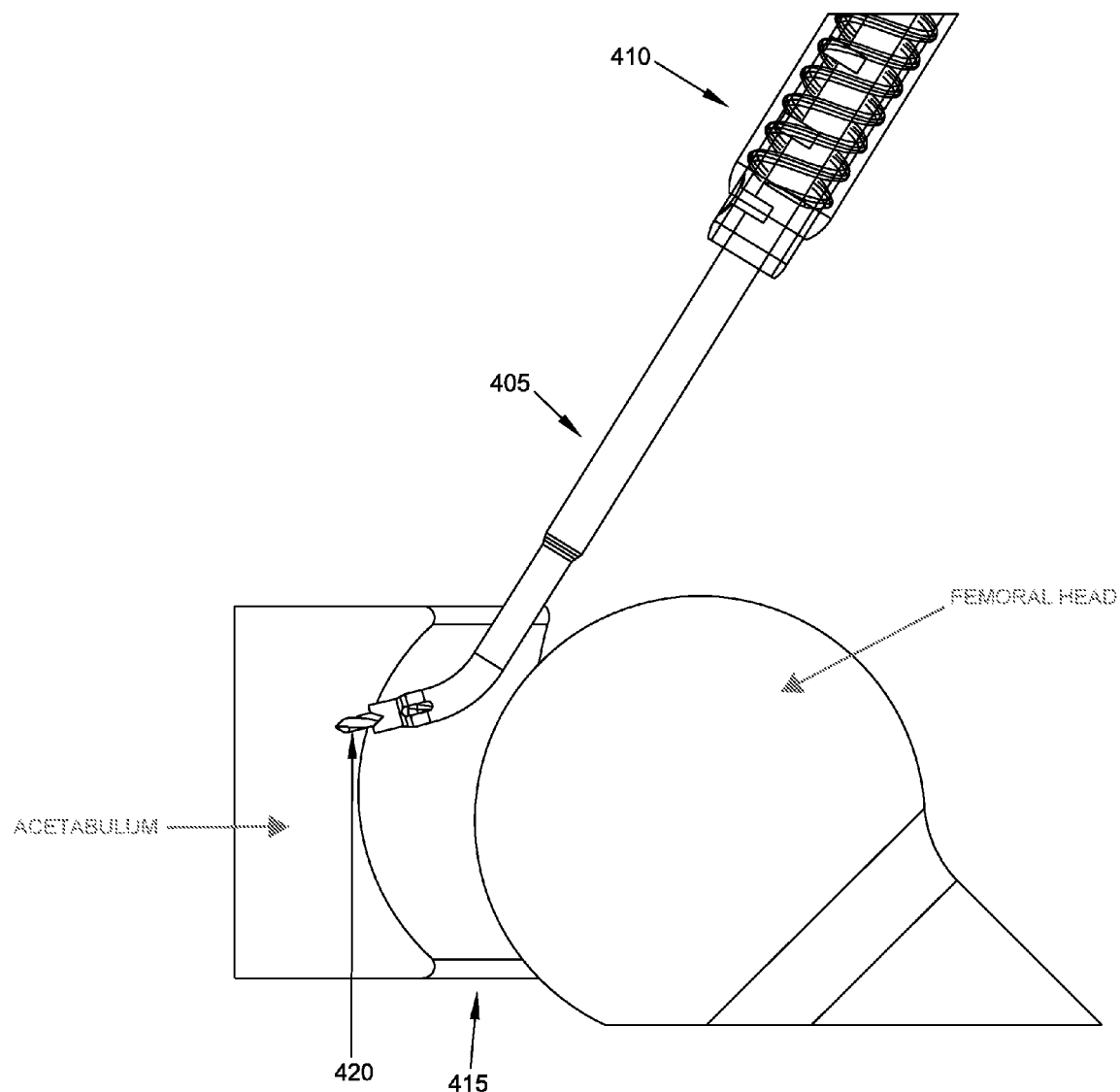

The provision of an articulating angled drill guide and flexible drill bit can be highly advantageous in numerous clinical situations, e.g., when drilling within the interior of a joint. Thus, for example, and looking now at FIGS. 50-57, there is shown an articulating angled drill guide 405 extending through an access cannula 410, with the distal end of articulating angled drill guide being disposed within the interior of a joint 415. More particularly, in this form of the invention, articulating angled drill guide 405 may be advanced into the interior of the joint with the articulating angled drill guide in a substantially straight configuration (FIGS. 50 and 51). This straight configuration may be helpful in providing a smaller profile by which to pass through the access cannula 410; it may also be helpful in entering a "tight" joint such as the hip joint where the space between the acetabular cup and femoral head is limited. Thereafter, the distal tip of articulating angled drill guide 405 is articulated into a curve so as to address a surface of the joint (FIGS. 52 and 53). Next, the distal end of articulating angled drill guide 405 is advanced so that the distal end of the articulating angled drill guide engages the surface which is to be drilled (FIGS. 54 and 55). Finally, a flexible drill bit 420 may be advanced through articulating angled drill guide 405 and drilled into the surface of the bone (FIGS. 56 and 57).

Friction-Reducing Flexible Drill Bit

In some situations the curvature of the flexible drill bit within an angled drill guide may be substantial, so that significant friction occurs between the flexible drill bit and the angled drill guide. When operated, the friction between the outer surface of the rotating flexible drill bit and the inner surface of the angled drill guide creates heat which will transfer to the flexible drill bit; a flexible drill bit operating at a higher temperature can have a reduced life. By way of example but not limitation, this can be important where a Nitinol flexible drill bit is operating in a highly stressed condition, so that the life of the Nitinol flexible drill bit is limited and is at or below the intended life of the drill bit to perform its function.

Figure 58:
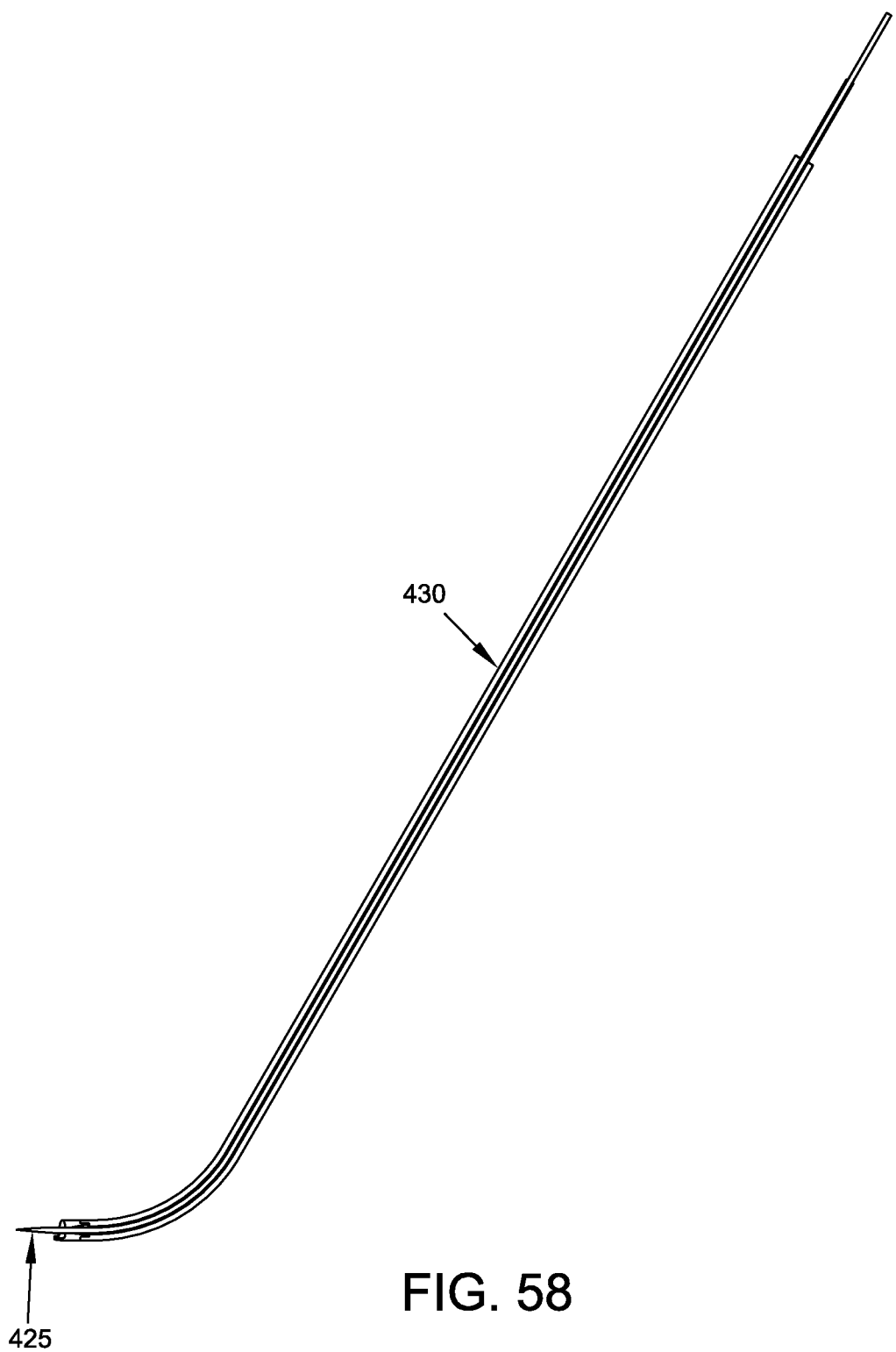
FIGS. 58-60 are schematic views showing a novel friction-reducing flexible drill bit formed in accordance with the present invention.
Figures 59, 60:
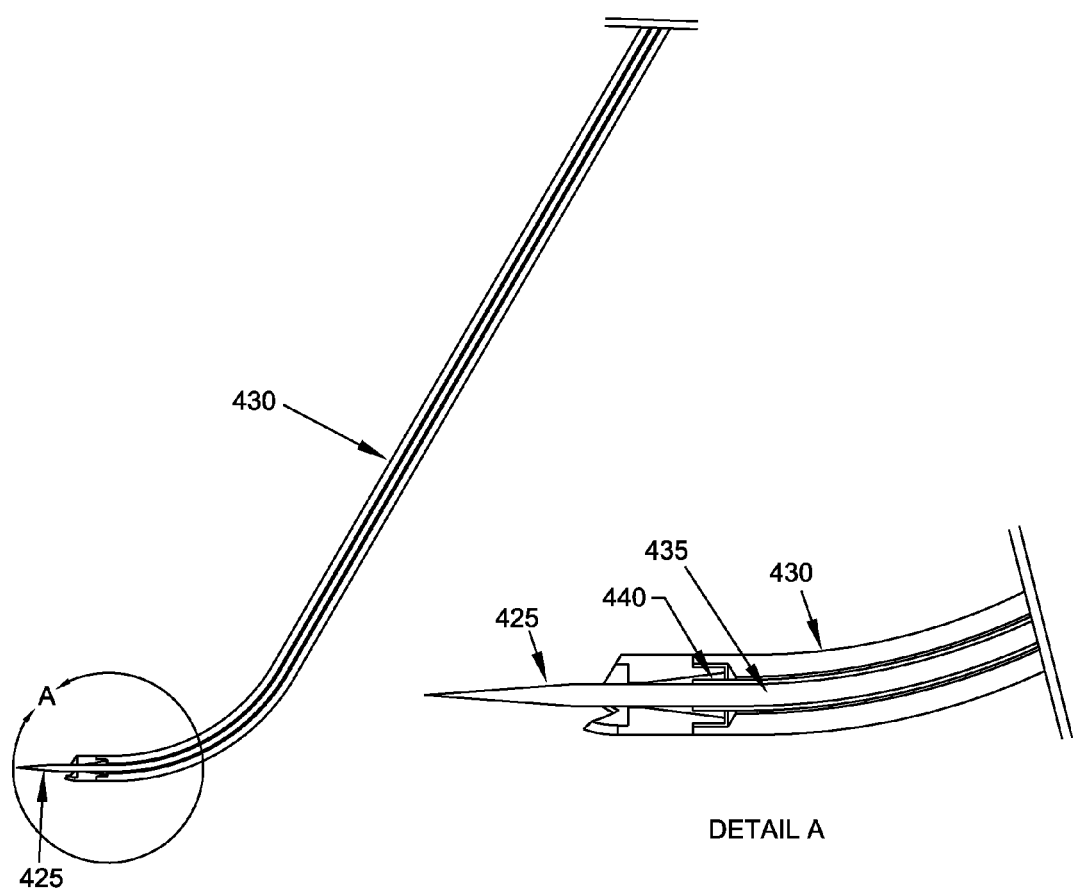
Figure 60C:
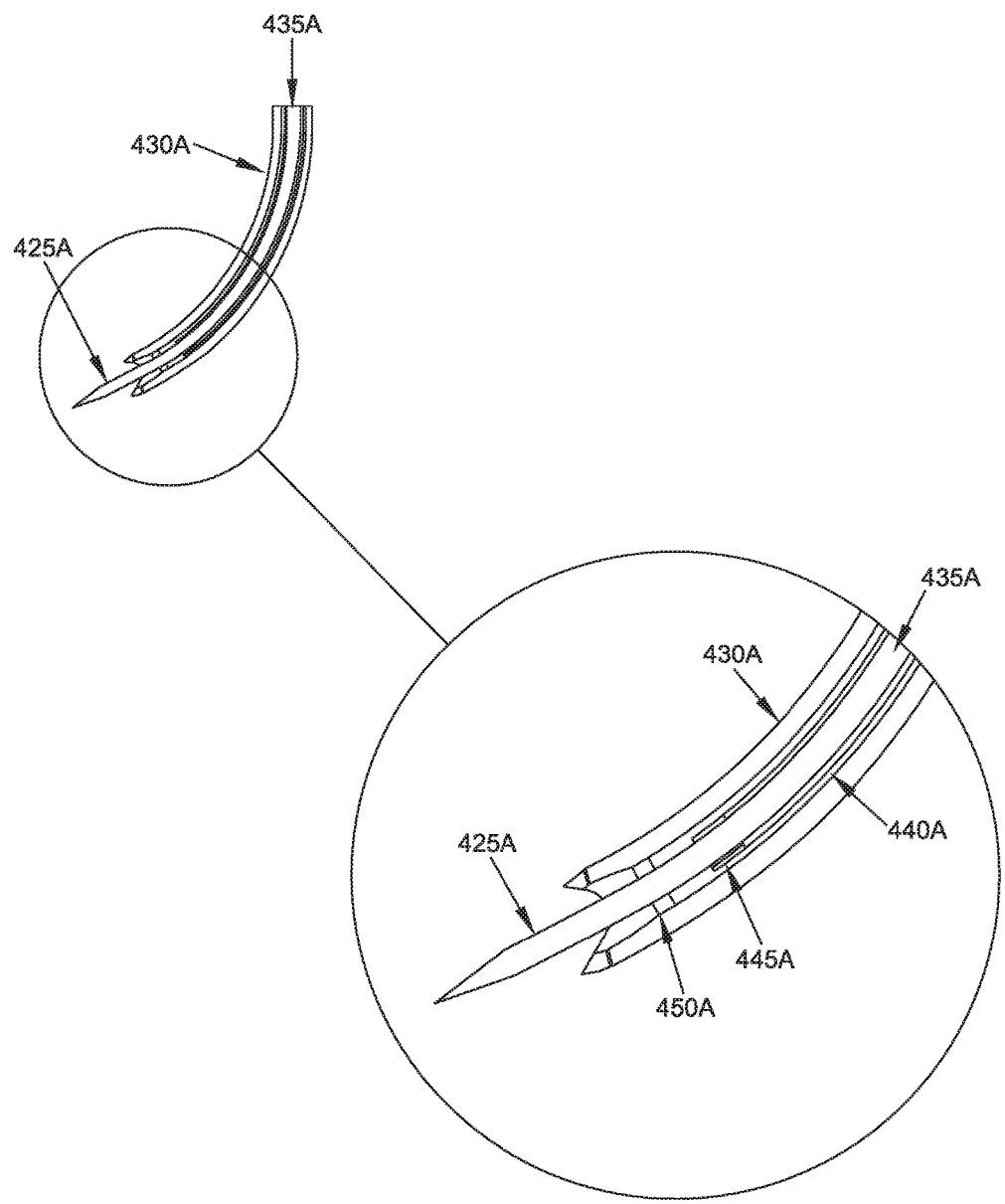

To this end, and looking now at FIGS. 58-60, a novel flexible drill bit 425 may be provided for use with an angled drill guide 430. Flexible drill bit 425 comprises a Nitinol (or other superelastic material) drill bit 435 having a low-friction coating 440 on its outer surface. In one preferred form of the invention, low-friction coating 440 comprises a polymer (e.g., PTFE) which is heat shrunk onto the outer diameter of Nitinol drill bit 435.

By way of example but not limitation, an angled drill guide was constructed with a distal end having a curve of approximately 60 degrees through an arc of approximately 1 inch radius. A Nitinol drill bit with a diameter of 0.0345 inch was constructed. The Nitinol drill bit was placed into the angled drill guide and operated. After approximately 4 minutes, the drill bit fractured. A second Nitinol drill bit was constructed with a diameter of 0.0345 inch, and a PTFE tube of approximately 0.008 inch thickness was heat shrunk onto the outer diameter of the Nitinol drill bit. The Nitinol drill bit with PTFE coating was placed into the angled drill guide and operated until it fractured, which occurred after approximately 8 minutes. It was found that the Nitinol drill bit with PTFE coating had a significantly longer life than the un-coated Nitinol drill bit in identical test conditions. This was attributed to the fact that the PTFE coating reduced friction between the inner diameter of the angled drill guide and outer diameter of the Nitinol drill bit; this enabled the construction to operate "cooler", which significantly extended the life of a Nitinol drill bit operating in a stressed condition.

In another form of the invention, and looking now at FIGS. 60A-60E, a novel flexible drill bit 425A may be provided for use with a novel angled drill guide 430A. Flexible drill bit 425A comprises a Nitinol (or other super-elastic material) drill bit 435A having a low-friction coating 440A on its outer surface. In one preferred form of the invention, low-friction coating 440A comprises a polymer which is heat shrunk onto the outer diameter of Nitinol drill bit 435A. This polymer is preferably FEP (fluorinated ethylene propylene), but it may also be PTFE, Nylon or another low-friction material compatible with the present invention. Low-friction coating 440A reduces the friction generated between flexible drill bit 425A and drill guide 430A, thus reducing the temperature of flexible drill bit 425A; a lower temperature will result in an increased fatigue life (i.e., the lifetime at which it will fail such as by fracturing). Additionally, flexible drill bit 425A may be cooled by the fluid which is typically circulated within the joint space during an arthroscopic procedure. This fluid cooling will act to further extend the life of flexible drill bit 425A.

Flexible drill bit 425A may also comprise a distal stop 445A. Distal stop 445A is formed integral with, or fixed onto, flexible drill bit 425A distal to low-friction coating 440A but proximal to a reduced inner diameter section 450A of angled drill guide 430A. Distal stop 445A has a profile larger than reduced inner diameter section 450A of the angled drill guide 430A. As a result of this construction, in the event that flexible drill bit 425A might fracture at any location proximal to distal stop 445A, distal stop 445A prevents the fractured portion of flexible drill bit 425A from exiting angled drill guide 430A (since distal stop 445A is too large to fit through reduced inner diameter section 450A of angled drill guide 430A), which would be undesirable inasmuch as there would then be a loose component in the joint space which can be difficult to remove.

Flexible drill bit 425A preferably also has a stop 455A which limits the distance which flexible drill bit 425A can extend out of the distal end of angled drill guide 430A. This provides a consistent, controlled drill depth into the bone. Stop 455A is preferably fixed to the proximal portion of the shaft of flexible drill bit 425A (as shown in FIGS. 60A and 60B) so as to provide a consistent drill depth hole. However, stop 455A may, alternatively, be movable and/or adjustable along the length of the shaft of flexible drill bit 425A, whereby to allow for a user-adjustable depth to the drill hole. In another aspect of the invention, one or more spacers (e.g., a disc-like spacer, a cylindrical spacer, etc., not shown) can selectively be attached to the distal end of stop 455A, thus reducing the distance flexible drill bit 425A can move distally relative to the angled drill guide 430A, and thus reducing the drill hole depth.

Figure 60D:
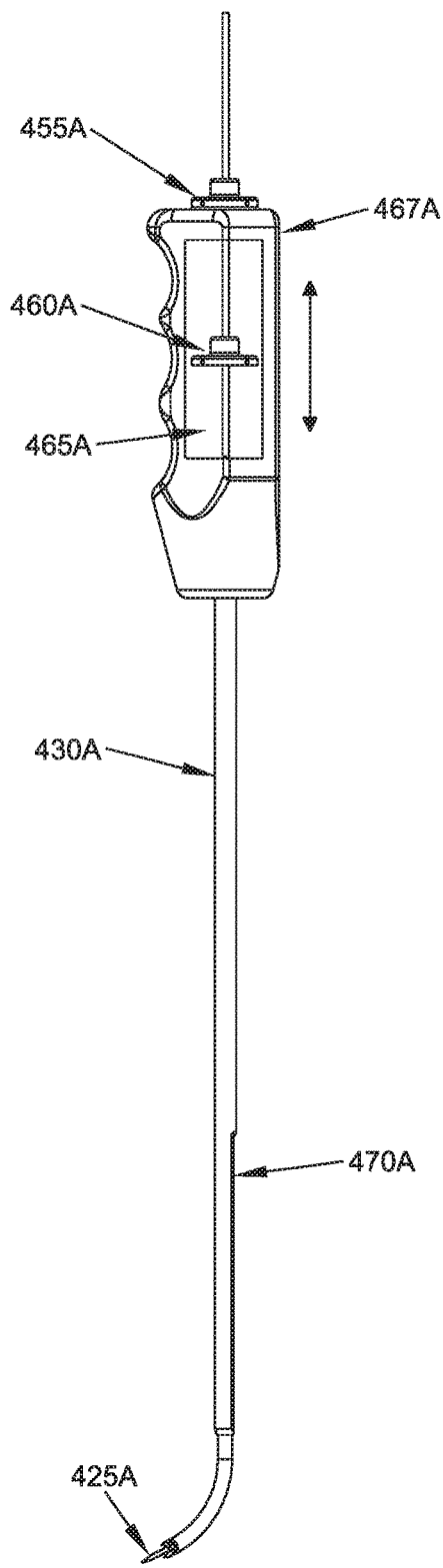

In one aspect of the present invention, and looking now at FIG. 60D, stop 460A is preferably disposed in a cavity 465A formed in the handle 467A of angled drill guide 430A so as to limit travel of the flexible drill bit 425A in the proximal direction, i.e., by engagement of stop 460A with the proximal end of cavity 465A. If desired, with this form of the invention, stop 455A may be omitted and multiple stops 460A may be set on the shaft of flexible drill bit 425A within cavity 465A, with one stop 460A being used to set the limit of distal movement of flexible drill bit 425A and the other stop 460A being used to set the limit of proximal movement of flexible drill bit 425A. Alternatively, a single stop 460A in cavity 465A may be used to set both the distal and proximal limits for flexible drill bit 425A. Note that cavity 465A may be open to the user (e.g., for user adjustment of the position of stop(s) 460A along the shaft of flexible drill bit 425A) or may be closed to the user (in which case the position of stop(s) 460A along the shaft of flexible drill bit 425A is set at the time of assembly).

In one preferred form of the invention, flexible drill bit 425A has a diameter of approximately 0.0345 inch and angled drill guide 430A has a bend radius of approximately 0.825 inch. It has been discovered that this combination of the diameter of flexible drill bit 425A and the radius of curvature of angled drill guide 430A provides the best access into the hip joint while maintaining sufficient fatigue life and torque strength to perform microfracture of an articular defect in the hip (i.e., by forming repeated drill holes into the acetabulum and/or femoral head). The diameter of drill bit 435A can be greater than 0.0345 inch; however, because strains and stresses are greater in a larger diameter drill bit 425A (assuming all other conditions are kept constant), the bend radius of angled drill guide 430A would then need to be larger than 0.825 inch in order to maintain sufficient fatigue life of flexible drill bit 425A. Alternatively, the diameter of flexible drill bit 435A can be smaller than 0.0345 inch; however, a smaller hole may not be a clinically desirable or efficacious and torque strengths may be limited with such a construction.

In a preferred form of the invention, flexible drill bit 435A comprises superelastic Nitinol comprising an oxide layer on its outer surface. Preferably the oxide layer is provided on an intermediate portion of the flexible drill bit, since it has been found that this oxide surface layer provides a surface which has superior fatigue resistance than, for example, a surface that has been mechanically polished, machined or ground to remove the oxide layer. It is believed that these mechanical polishing, machining or grinding processes may leave surface scratches and stress risers (stress concentrations) from which fractures can propagate. However, it is also preferred that the distal end of the flexible drill bit (i.e., at least the portion of the flexible drill bit which extends into the bone) be free of the oxide surface layer, since wear of the oxide surface layer may release undesirable particulates.

Angled drill guide 430A preferably has a cutaway 470A (FIGS. 60A, 60B and 60D) on the side of the shaft of angled drill guide 430A which is on the "outside" of the curved distal portion of angled drill guide 430A. This cutaway 470A reduces the profile of the shaft of angled drill guide 430A on the side of the shaft of angled drill guide 430A which typically faces the femoral head during arthroscopic hip surgery (see, for example, FIGS. 52-57). This feature provides for more clearance between the femoral head and angled drill guide 430A, thus reducing the chances that angled drill guide 430A will contact and damage the articular surface of the femoral head.

Figure 60E:
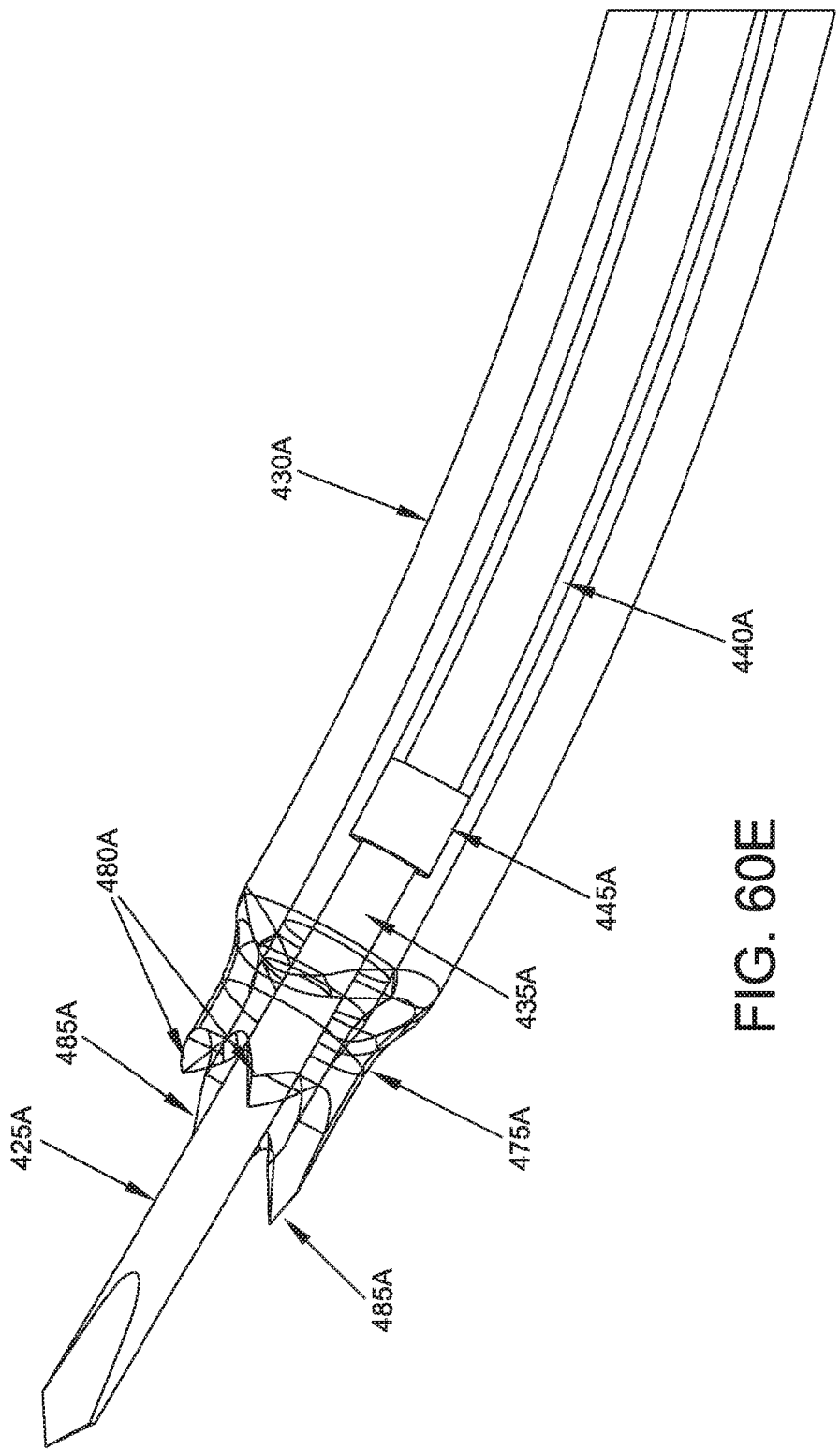

In one form of the present invention, angled drill guide 430A preferably also has a reduced diameter 475A at its distal tip (see FIG. 60E). This allows for better visualization of the target bone site inasmuch as there is less visual obstruction. Reduced diameter 475A also can be a result of forming the reduced inner section 450A in the shaft of angled drill guide 430A (e.g., such as when reduced inner section 450A is produced by crimping angled drill guide 430A inwardly). The distal tip of angled drill guide 430A preferably comprises at least one inner tooth 480A and at least one outer tooth 485A to engage the target bone. Outer tooth 485A preferably extends further distally than inner tooth 480A. This enables both inner tooth 480A and outer tooth 485A to completely engage the target bone when angled drill guide 430A addresses the target site at an angle. This feature will reduce the chances that the tip of angled drill guide 430A will slip on the target bone while flexible drill bit 425A penetrates the bone. In one preferred embodiment, and as shown in FIGS. 60A-E, the outer tooth 485A is located on the "outside" of the curved distal portion of angled drill guide 430A, while the inner tooth 480A is located on the "inside" of the curved distal portion of angled drill guide 430A.

By way of example but not limitation, an angled drill guide 430A has been constructed with a distal end having a curve of approximately 60 degrees through an arc of approximately 1 inch radius. A Nitinol drill bit 425A with a diameter of 0.0345 inch was constructed. The Nitinol drill bit 425A was placed into the angled drill guide 430A and operated. After approximately 4 minutes of use, the drill bit fractured. A second Nitinol drill bit was constructed with a diameter of 0.0345 inch, and a PTFE tube 440A of approximately 0.008 inch thickness was heat-shrunk onto the outer diameter of the Nitinol drill bit 425A. The Nitinol drill bit 425A with PTFE coating 440A was placed into the angled drill guide and operated until it fractured, which occurred after approximately 8 minutes of use. It was found that the Nitinol drill bit 425A with PTFE coating 440A had a significantly longer life than the "un-coated" Nitinol drill bit in identical test conditions. This was attributed to the fact that the PTFE coating 440A reduced friction between the inner diameter of the angled drill guide 430A and outer diameter of the Nitinol drill bit 425A; this enabled the construction to operate "cooler", which significantly extended the life of a Nitinol drill bit operating in a stressed condition.

Additional Subject Matter

Looking next at FIGS. 61-66, there is shown another angled drill guide which may be used with a flexible drill bit.

Figure 61:
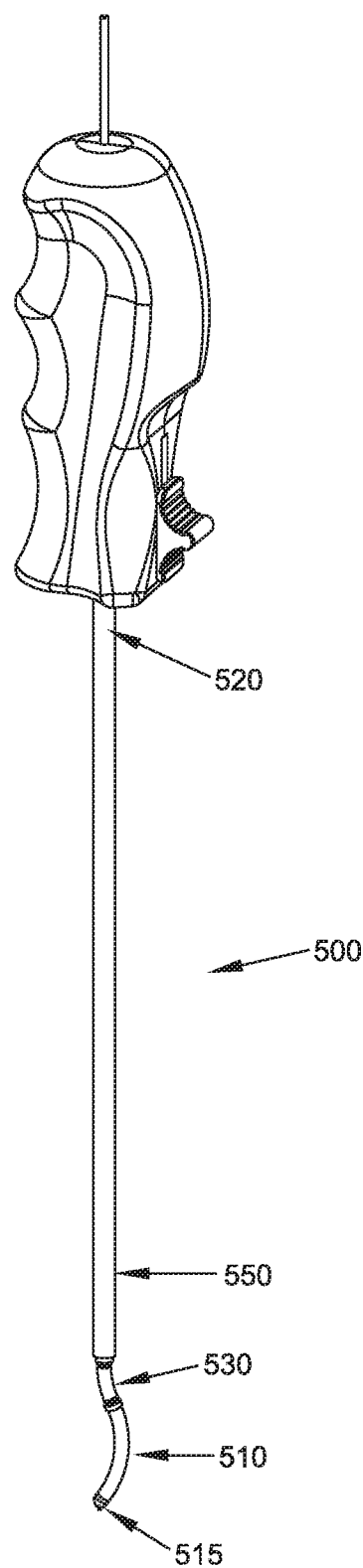
FIGS. 61-66 are schematic views showing another novel angled drill guide which may be used with a flexible drill bit.
Figure 62:
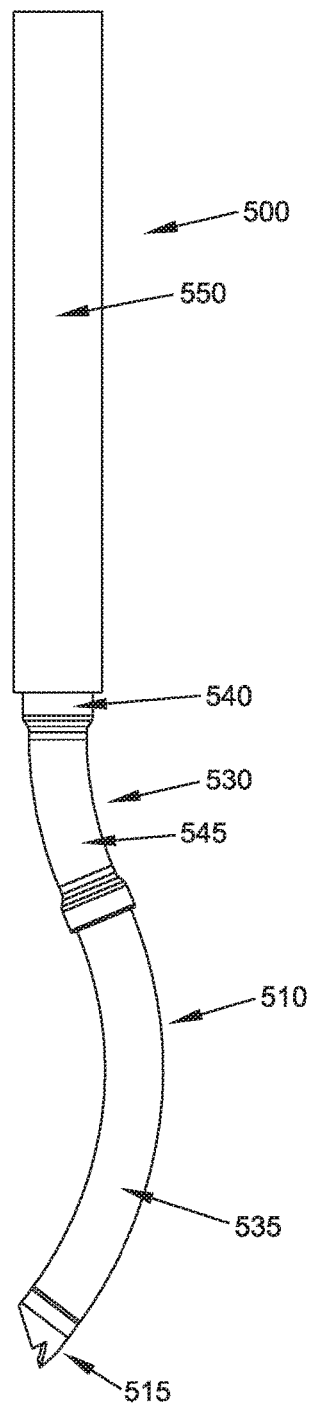
Figure 63:
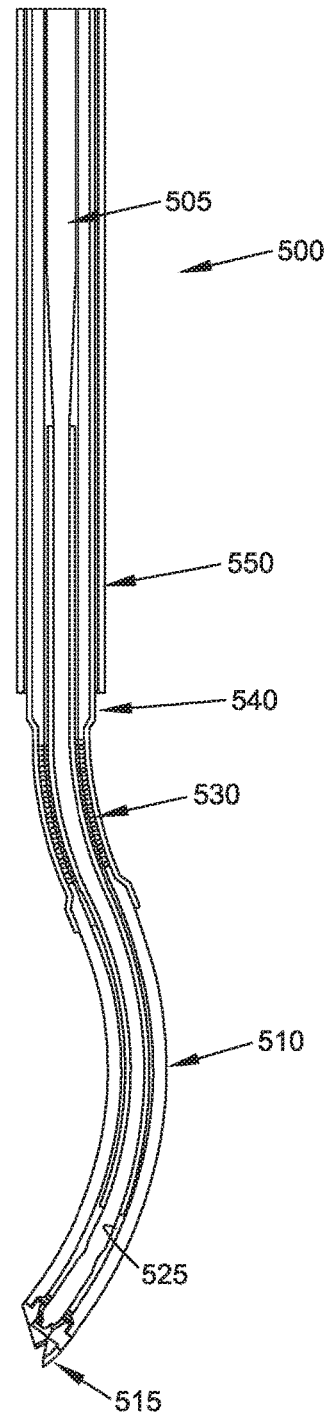
Figure 64:
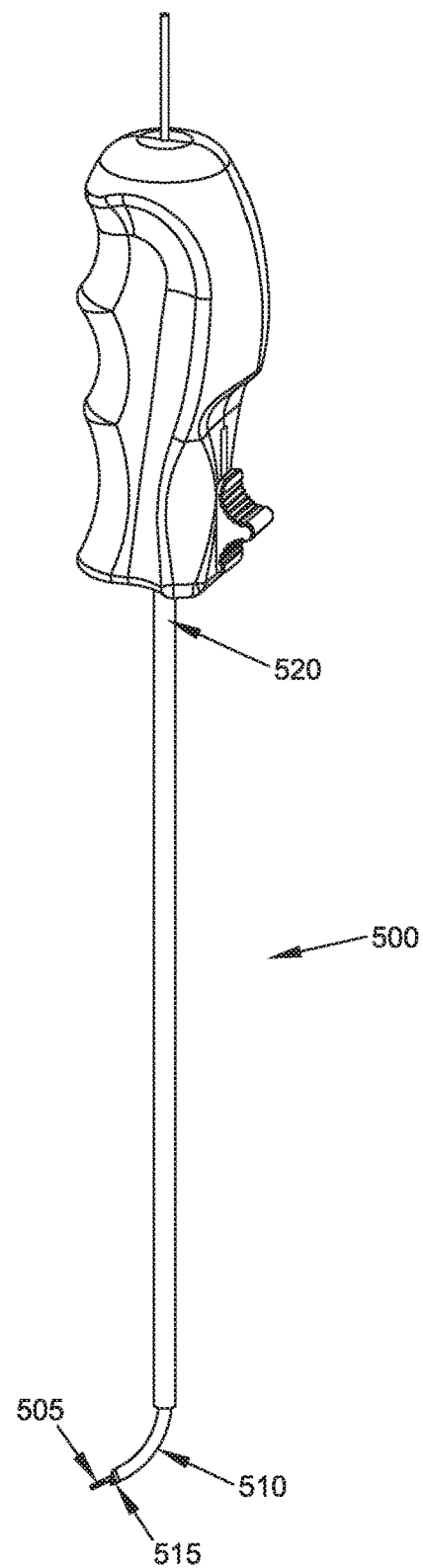
Figures 65, 66:
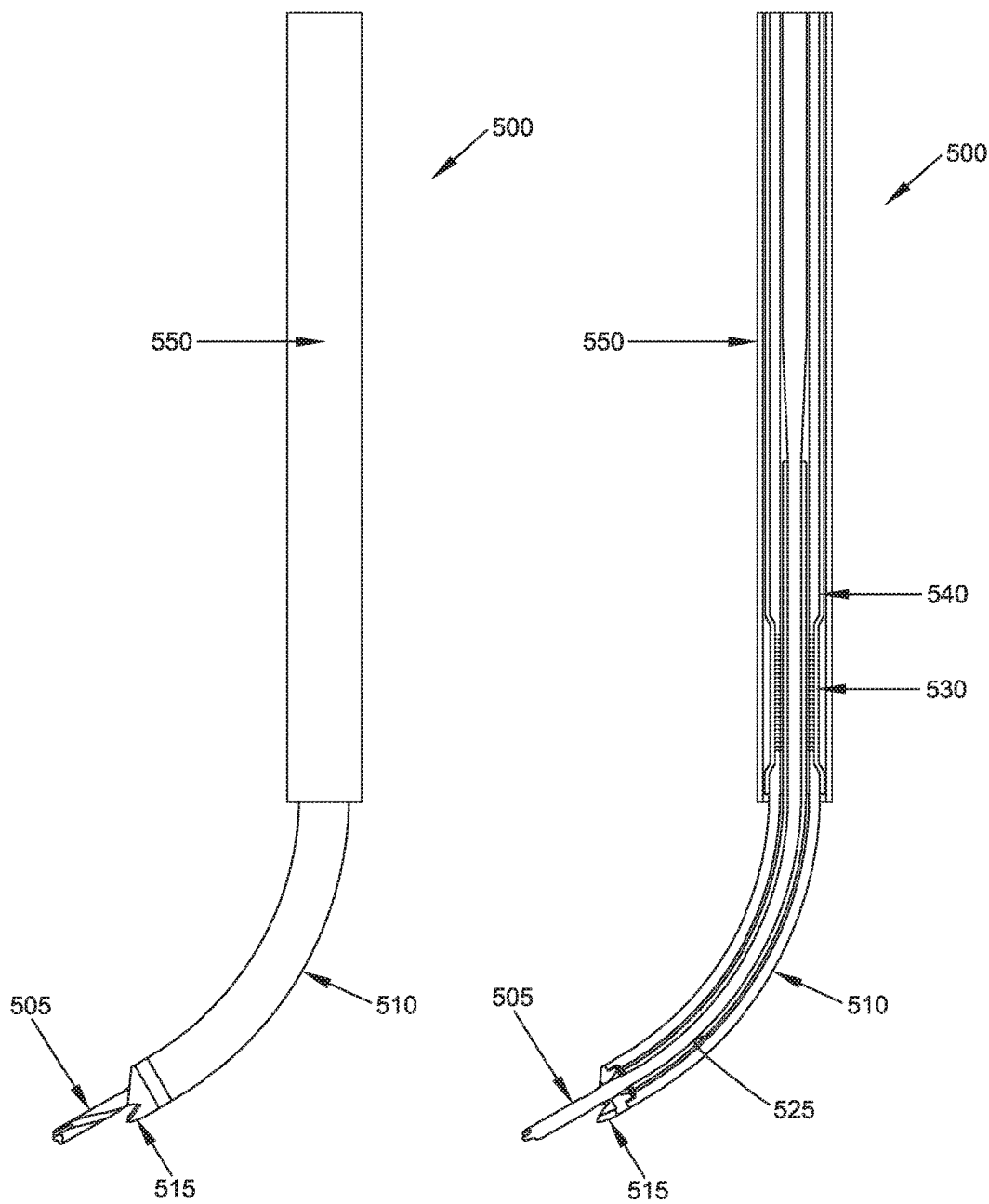

More particularly, in this form of the invention, and looking now at FIGS. 61-63, there is provided a novel angled drill guide 500 which may be used to support a flexible drill bit 505. Novel angled drill guide 500 generally comprises an elongated tube 510 having a distal end 515, a proximal end 520 and a lumen 525 extending therebetween. Near its distal end, elongated tube 510 includes a flexible region 530. Flexible region 530 essentially separates elongated tube 510 into a tip portion 535 and a body portion 540. Flexible region 530 is preferably formed by (i) reducing the outer diameter of the side wall of elongated tube 510, or (ii) laser cutting slits in the side wall of elongated tube 510, or (iii) both reducing the outer diameter of the side wall of the elongated tube and laser cutting slits in the side wall of the elongated tube (such as is shown in the figures). An FEP sleeve 545 is preferably heat-shrunk over flexible region 530 so as to provide flexible region 530 with a smooth outer profile without interfering with its flexibility.

A telescoping outer tube 550 is positioned coaxially over elongated tube 510. Telescoping outer tube 550 is selectively advanceable over flexible region 530 of elongated tube 510 so as to selectively stabilize distal portion 535 of elongated tube 510 relative to body portion 540 of elongated tube 510.

Flexible drill bit 505 is preferably pre-loaded into novel angled drill guide 500 prior to use, with flexible drill bit 505 positioned so that the leading tip of the flexible drill bit resides just inside lumen 525 of elongated tube 510 (see FIG. 63). Such pre-loading of flexible drill bit 505 into angled drill guide 500 may be effected in the operating room or at the time of manufacture or assembly.

In use, telescoping outer tube 550 is initially retracted to the position shown in FIGS. 61-63 so that tip portion 535 of elongated tube 510 is able to flex relative to body portion 540 of elongated tube 510. This allows angled drill guide 500 to pass down the surgical corridor leading to the arthroscopic site (e.g., through a straight access cannula). Then telescoping outer tube 550 is advanced forward, extending over flexible region 530 of elongate tube 510, whereby to stabilize tip portion 535 of elongated tube 510 relative to body portion 540 of elongated tube 510 (FIGS. 64-66), with tip portion 535 extending at an angle to the longitudinal axis of body portion 540. With tip portion 535 of elongated tube 510 so stabilized, flexible drill bit 505 is advanced out the distal end of the angled drill guide, whereby to form a hole in a target bone. Then, when the desired hole has been formed, flexible drill bit 505 may be withdrawn and angled drill guide 500 may be used for other purposes, e.g., to deliver a bone anchor into the hole formed in the target bone. When angled drill guide 500 is to be withdrawn, telescoping outer tube 550 is pulled back, thereby restoring flexibility to flexible region 530 of elongated tube 510, and then elongated tube 510 is retracted back along the surgical corridor to the surface of the skin.

Nitinol Flexible Drill Bit

In the foregoing sections there are disclosed various flexible drill bits which may be used in conjunction with angled drill guides to traverse a non-linear space and drill a hole in bone. And in the foregoing sections it is disclosed that the various flexible drill bits may comprise Nitinol.

Nitinol is a shape memory alloy which can exhibit a so-called "shape memory effect" and/or a so-called "superelasticity effect" (sometimes also called "pseudoelasticity"). The shape memory alloy Nitinol can exist in various states, e.g., an austenitic state and a martensitic state. Nitinol may exhibit different material properties when it is in its different states, e.g., Nitinol may have one set of material properties when it is in its austenitic state (e.g., a stiffer quality) and another set of material properties when it is in its martensitic state (e.g., a softer, more pliable quality). It should also be appreciated that as the Nitinol changes temperature, it can change states, i.e., when Nitinol is fully austenitic and is cooled, it will start to transition to its martensitic state at one temperature (Ms) and finish transitioning to its martensitic state at another temperature (Mf), with Mf<Ms; and when the Nitinol is fully martensitic and is heated, it will start to transition to its austenitic state at one temperature (As) and finish transitioning to its austenitic state at another temperature (Af), with As<Af. In general, Mf<Ms<As<Af. And it should be appreciated that it is possible to modify, to some extent, the As, Af, Ms and Mf temperatures of the Nitinol during fabrication of the Nitinol and/or during fabrication of an article formed out of the Nitinol.

It has been observed that when a flexible drill bit is disposed within an angled drill guide and is thereafter used to drill a hole in bone, a significant amount of heat can be generated due to the friction between the flexible drill bit and the angled drill guide (e.g., where the rotating flexible drill bit contacts the inner wall of the lumen of the angled drill guide). It has also been observed that, where the flexible drill bit is formed out of Nitinol, this heat may cause the temperature of the Nitinol flexible drill bit to rise above its Af temperature, in which case the Nitinol flexible drill bit will become fully austenitic, exhibit full superelasticity and effectively become "stiffer" within the angled drill guide. This stiffening of the Nitinol flexible drill bit reduces the ability of the Nitinol flexible drill bit to turn easily within the angled drill guide and can thereby inhibit drilling. Excessive heat build-up and hence stiffening of the Nitinol flexible drill bit can also cause excess wear on the Nitinol flexible drill bit and/or angled drill guide, and can make it difficult to withdraw the Nitinol flexible drill bit from the angled drill guide.

It should also be noted that simply inserting the flexible drill bit into the body of a patient can cause the temperature of the flexible drill bit to rise significantly, e.g., from room temperature (typically 22 degrees C., and an operating room is typically cooler than that) to body temperature (typically 37 degrees C.). Of course, the heat generated during drilling is typically significantly higher than body temperature.

In accordance with the present invention, the distal end of the Nitinol flexible drill bit (i.e., the portion of the Nitinol flexible drill bit that passes through the curved portion of the angled drill guide) is preferably formed so that it has an elevated Af temperature, i.e., an Af temperature which is greater than the temperature to which the Nitinol flexible drill bit will rise due to insertion into the body and, more significantly, due to friction between the Nitinol flexible drill bit and the angled drill guide during rotation of the flexible drill bit. In this way, the flexible drill bit will remain in a substantially martensitic state (in which it is relatively soft and pliable) and will not transition to a substantially austenitic state (in which it is relatively stiff). In other words, in accordance with the present invention, the flexible drill bit is formed out of Nitinol which has an Af temperature greater than the temperature to which the drill bit will rise during drilling. As a result, when the temperature of the Nitinol flexible drill bit rises during drilling (e.g., due to friction between the Nitinol flexible drill bit and the angled drill guide), the temperature of the Nitinol flexible drill bit will still remain below the Af temperature of the Nitinol flexible drill bit. Accordingly, the Nitinol flexible drill bit will not become fully austenitic during use and will not exhibit full superelasticity during use, and hence the drill bit will not become "stiffer" within the angled drill guide as the Nitinol flexible drill bit heats up.

Figure 67:
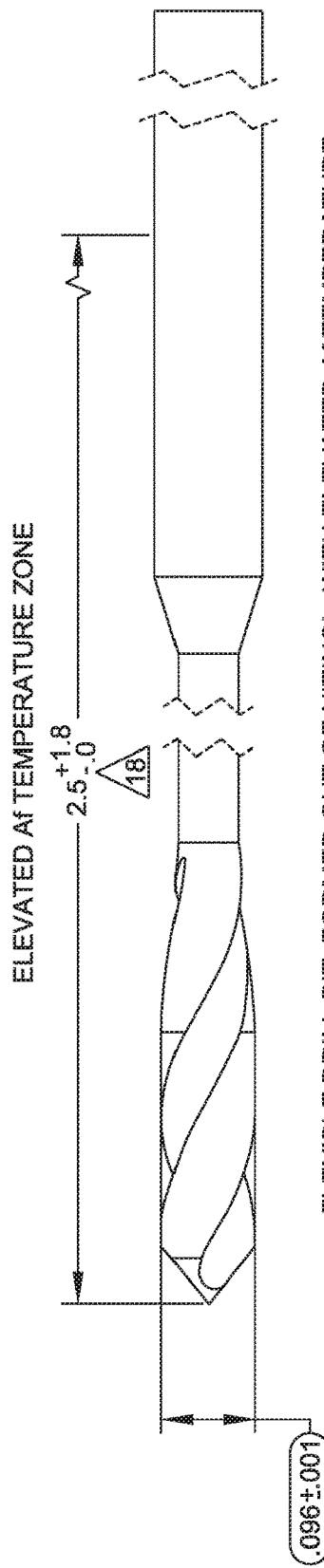
FIG. 67 is a schematic view showing how a Nitinol flexible drill bit may have its Af temperature elevated (e.g., by heat treating the Nitinol) so as to prevent the drill bit from becoming fully austenitic during use.

More particularly, in one preferred embodiment of the present invention, the Nitinol flexible drill bit is preferably manufactured out of a "standard" Nitinol wire workpiece having a composition of approximately 56 wt % nickel with most of the remaining wt % being provided by titanium, a diameter of 0.110 inch and an Af range of approximately 5-18 degrees C. In one preferred form of the invention, the "standard" Nitinol wire workpiece is formed out of Nitinol meeting the ASTM F2063 standard (nickel 55.8 wt %, oxygen 0.05 wt % or less, carbon 0.02 wt % or less, and titanium making up the remaining wt %, with the inclusion area fraction being 2.8% or less). The distal portion of the Nitinol flexible drill bit is then heat treated so as to raise its Af range from the "standard" Nitinol Af range of approximately 5-18 degrees C. to an elevated Af temperature range of approximately 42-54 degrees C. See FIG. 67. In one preferred form of the invention, the heat treatment consists of inserting the Nitinol flexible drill bit into an oven at ambient temperature; increasing the temperature to 300 degrees C. (plus or minus 10 degrees C.) over 30 minutes (plus or minus 10%) and holding it there for one hour (plus or minus 10%); increasing the temperature to 425 degrees C. (plus or minus 10 degrees C.) over 15 minutes (plus or minus 10%) and holding it there for 2 hours (plus or minus 10%); dropping the temperature to 350 degrees C. (plus or minus 10 degrees C.) over 15 minutes (plus or minus 10%) and holding it there for one hour (plus or minus 10%); and then removing the Nitinol flexible drill bit from the oven and air cooling.

Essentially, the goal of heat treating the distal portion of the Nitinol flexible drill bit is to raise its Af temperature as high as possible so that the Nitinol flexible drill bit will not reach the Af temperature during drilling. As a result, the Nitinol flexible drill bit will not become fully austenitic and will not exhibit full superelasticity and will not become "stiffer" as the Nitinol flexible drill bit heats up during drilling. Thus, by forming the Nitinol flexible drill bit with an elevated Af temperature which is above the highest temperature reached by the Nitinol flexible drill bit during drilling, the Nitinol flexible drill bit will continue to turn easily in the angled drill guide even as the Nitinol flexible drill bit heats up during drilling, will not wear the Nitinol flexible drill bit and/or the angled drill guide excessively during drilling, and the Nitinol flexible drill bit will be easy to insert into, and withdraw from, the angled drill guide.

By way of example but not limitation, in one preferred form of the invention, the novel Nitinol flexible drill bit comprises a distal drill tip having a diameter of 0.096 inch, an intermediate shaft portion having a diameter of 0.061 inch, a proximal shaft portion having a diameter of 0.110 inch, an Af of approximately 42-54 degrees C., and its associated drill guide has a 20 degree bend angle with a 1.5" radius (midline).

Modifications

While the present invention has been described in terms of certain exemplary preferred embodiments, it will be readily understood and appreciated by those skilled in the art that it is not so limited, and that many additions, deletions and modifications may be made to the preferred embodiments discussed herein without departing from the scope of the invention.

What is claimed is:

1. A method for forming a Nitinol flexible drill bit, the method comprising:
   providing a Nitinol wire workpiece comprising a distal end and a proximal end, the Nitinol wire workpiece having an initial Af range of approximately 5-18 degrees C.;
   machining a cutting tip on the distal end of the Nitinol wire workpiece to form a Nitinol flexible drill bit; and
   heat treating the distal end of the Nitinol wire workpiece so as to raise the Af range of only the distal end of the Nitinol wire workpiece to an elevated Af range of approximately 42-54 degrees C.

2. A method according to claim 1 wherein heat treating the distal end of the Nitinol wire workpiece comprises:
   inserting the distal end of the Nitinol wire workpiece into an oven at ambient temperature;
   increasing the temperature to 300 degrees C. (plus or minus degrees C.) over 30 minutes (plus or minus 10%) and holding the temperature there for one hour (plus or minus 10%);
   increasing the temperature to 425 degrees C. (plus or minus degrees C.) over 15 minutes (plus or minus 10%) and holding the temperature there for 2 hours (plus or minus 10%);
   dropping the temperature to 350 degrees C. (plus or minus degrees C.) over 15 minutes (plus or minus 10%) and holding the temperature there for one hour (plus or minus 10%); and
   removing the distal end of the Nitinol wire workpiece from the oven and air cooling.

3. A method according to claim 1 wherein the Nitinol flexible drill bit comprises:
   a proximal shaft portion for connecting to a source of turning;
   a distal cutting tip portion for boring into a material; and
   an intermediate shaft portion extending between the proximal shaft portion and the distal cutting tip portion, the intermediate shaft portion being characterized by (i) sufficient longitudinal flexibility so as to permit the Nitinol flexible drill bit to be passed along a curve, and (ii) sufficient torsional strength to permit the Nitinol flexible drill bit to bore into the material.

4. A method according to claim 3 wherein the distal cutting tip portion of the Nitinol flexible drill bit and the intermediate shaft portion of the Nitinol flexible drill bit are configured to be disposed within a lumen of an angled drill guide.

5. A method according to claim 4 wherein the angled drill guide comprises:
   a curved distal section;
   a less curved proximal section; and
   a lumen extending between the curved distal section and the less curved proximal section.

6. A method according to claim 3 wherein the intermediate shaft portion has sufficient longitudinal flexibility to permit the Nitinol flexible drill bit to be passed along a radius of curvature of approximately 1.5 inches.

7. A method according to claim 3 wherein the intermediate shaft portion has sufficient torsional strength to transmit at least two inch-pounds of torque.

8. A method according to claim 3 wherein the outer diameter of the intermediate shaft portion is at least 15% smaller than the outer diameter of the distal cutting tip portion.

9. A method according to claim 3 wherein the outer diameter of the intermediate shaft portion is at least 25% smaller than the outer diameter of the proximal shaft portion.

10. A method according to claim 3 wherein the outer diameter of the intermediate shaft portion is approximately 36% smaller than the outer diameter of the proximal shaft portion.

11. A method according to claim 3 wherein the proximal shaft portion, the intermediate shaft portion and the distal cutting tip portion are formed integral with one another.

12. A method according to claim 3 wherein heat treating the distal end of the Nitinol wire workpiece comprises heat treating the distal cutting tip portion and the intermediate shaft portion.

13. A method for forming a Nitinol flexible drill bit, the method comprising:
   providing a Nitinol wire workpiece comprising a distal end and a proximal end;
   machining a cutting tip on the distal end of the Nitinol wire workpiece to form a Nitinol flexible drill bit; and
   heat treating the distal end of the Nitinol wire workpiece so that only the distal end of the Nitinol wire workpiece has an Af temperature which is greater than the highest temperature that the Nitinol flexible drill bit will reach during drilling.

14. A method according to claim 13 wherein the distal end of the Nitinol wire workpiece comprises a distal cutting tip portion and a reduced-diameter intermediate shaft portion extending between the distal cutting tip portion and the proximal end of the Nitinol wire workpiece.

15. A method according to claim 14 wherein the outer diameter of the intermediate shaft portion is at least 15% smaller than the outer diameter of the distal cutting tip portion.

16. A method according to claim 13 wherein the Af temperature is 42-54 degrees C.

17. A method according to claim 13 wherein the Nitinol flexible drill bit comprises:
   a proximal shaft portion for connecting to a source of turning;
   a distal cutting tip portion for boring into a material; and
   an intermediate shaft portion extending between the proximal shaft portion and the distal cutting tip portion, the intermediate shaft portion being characterized by (i) sufficient longitudinal flexibility so as to permit the Nitinol flexible drill bit to be passed along a curve, and (ii) sufficient torsional strength to permit the Nitinol flexible drill bit to bore into the material.

18. A method according to claim 17 wherein the distal cutting tip portion of the Nitinol flexible drill bit and the intermediate shaft portion of the Nitinol flexible drill bit are configured to be disposed within a lumen of an angled drill guide.

19. A method according to claim 18 wherein the angled drill guide comprises:
   a curved distal section;
   a less curved proximal section; and
   a lumen extending between the curved distal section and the less curved proximal section.

20. A method according to claim 17 wherein the intermediate shaft portion has sufficient longitudinal flexibility to permit the Nitinol flexible drill bit to be passed along a radius of curvature of approximately 1.5 inches.

21. A method according to claim 17 wherein the intermediate shaft portion has sufficient torsional strength to transmit at least two inch-pounds of torque.

22. A method according to claim 17 wherein the outer diameter of the intermediate shaft portion is at least 15% smaller than the outer diameter of the distal cutting tip portion.

23. A method according to claim 17 wherein the outer diameter of the intermediate shaft portion is at least 25% smaller than the outer diameter of the proximal shaft portion.

24. A method according to claim 17 wherein the outer diameter of the intermediate shaft portion is approximately 36% smaller than the outer diameter of the proximal shaft portion.

25. A method according to claim 17 wherein the proximal shaft portion, the intermediate shaft portion and the distal cutting tip portion are formed integral with one another.

26. A method according to claim 17 wherein heat treating the distal end of the Nitinol wire workpiece comprises heat treating the distal cutting tip portion and the intermediate shaft portion.

\* \* \* \* \*